(12) United States Patent
Cheng et al.

(10) Patent No.: US 6,929,928 B2
(45) Date of Patent: Aug. 16, 2005

(54) GENES ENCODING CAROTENOID COMPOUNDS

(75) Inventors: Qiong Cheng, Wilmington, DE (US); Natalia Sedkova, Cherry Hill, NJ (US); Luan Tao, Claymont, DE (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 10/808,807

(22) Filed: Mar. 24, 2004

(65) Prior Publication Data

US 2004/0253663 A1 Dec. 16, 2004

Related U.S. Application Data

(60) Provisional application No. 60/477,874, filed on Jun. 12, 2003, and provisional application No. 60/527,083, filed on Dec. 3, 2003.

(51) Int. Cl.[7] .............................. C12P 5/00; C12P 5/02; C12N 9/00; C12N 1/20; C12N 1/14
(52) U.S. Cl. .................. 435/67; 435/252.3; 435/254.2; 435/254.11; 435/257.2; 435/183; 435/419; 435/254.21; 435/252.22; 435/254.6; 435/252.31; 435/254.23; 435/252.2; 435/252.32; 435/252.33; 435/252.34; 435/252.35; 435/320.1; 435/254.3; 536/23.2
(58) Field of Search .............................. 435/67, 252.3, 435/254.2, 254.11, 257.2, 183, 254.21, 252.22, 254.6, 252.31, 254.23, 419, 252.2, 320.1, 254.1

(56) References Cited

U.S. PATENT DOCUMENTS 5,429,939 A  7/1995  Misawa et al.
5,530,188 A  6/1996  Ausich et al.
5,530,189 A  6/1996  Ausich et al.
5,545,816 A  8/1996  Ausich et al.
5,658,472 A  8/1997  Bartha et al.
2004/0209365 A1 * 10/2004 Rouviere et al. ........... 435/456
2004/0219629 A1 * 11/2004 Cheng et al. .................. 435/67

FOREIGN PATENT DOCUMENTS

WO    WO 02/079395    10/2002

OTHER PUBLICATIONS

Kamiunten et. al. Isolation and characterization of carotenoid biosynthetic genes from *Pantoea agglomerans* with sequence accession No. AB076662.*

(Continued)

*Primary Examiner*—Rebecca E. Prouty
*Assistant Examiner*—Kagnew Gebreyesus

(57) ABSTRACT

A unique carotenogenic biosynthetic gene cluster has been isolated from *Pantoea agglomerans* strain DC404, wherein the genetic organization of the cluster is crtE-idi-crtY-crtI-crtB-crtZ. The genes contained within this cluster encode geranylgeranyl pyrophosphate (GGPP) synthetase (CrtE), isopentenyl pyrophosphate isomerase (Idi), lycopene cyclase (CrtY), phytoene desaturase (CrtI), phytoene synthase (CrtB), and β-carotene hydroxylase (CrtZ). The gene cluster, genes and their products are useful for the conversion of farnesyl pyrophosphate to carotenoids. Vectors containing those DNA segments, host cells containing the vectors and methods for producing those enzymes by recombinant DNA technology in transformed host organisms are disclosed.

11 Claims, 6 Drawing Sheets

OTHER PUBLICATIONS

Nells and Leenheer, Microbial sources of carotenoid pigments used in foods and feeds, Journal Appl. Bacteriol. 70: pp. 181–191, 1991.

Misawa and Shimada, Metabolic engineering for the production of carotenoids in non–carotenogenic bacteria and yeasts, J. Biotech. vol. 59:pp. 169–181, 1998.

Hauben et al., Phylogenetic Position of Phbytopathogens within the Enterobacteriaceae, Syst. Appl. Microbiol. 21(3): pp. 384–397, Aug. 1998.

G. Armstrong, Eubacteria Show Their True Colors: Genetics of Carotyenoid Pigment biosynthesis from Microbes to Plants, J. Bact. 178: 4795–4802, 1994.

Armstrong et al., Genetics of Eubacterial Carotenoid Biosynthesis: A Colorful Tale, Annu. Rev. Microbiol. 51: pp. 629–659, 1997.

GenBank Accession No. M87280, *Pantoea agglomerans*, Apr. 11, 2001.

GenBank AccessionNo. D90087, *Pantoea stewartii*, Dec. 18, 2002.

GenBank Accession No. AY166713, *Pantoea ananatis*, Aug. 24, 2002.

GenBank Accession No. AB076662, *Pantoea agglomerans* pv. *Milletlae*, Dec. 26, 2001.

* cited by examiner

GENES ENCODING CAROTENOID COMPOUNDS

This application claims the benefit of U.S. Provisional Application No. 60/477,874 filed Jun. 12, 2003 and U.S. Provisional Application No. 60/527,083 filed Dec. 3, 2003.

FIELD OF THE INVENTION

The invention relates to the field of molecular biology and microbiology. More specifically, this invention pertains to nucleic acid fragments isolated from *Pantoea agglomerans* encoding enzymes useful for microbial production of carotenoid compounds (e.g., lycopene, β-carotene, and zeaxanthin).

BACKGROUND OF THE INVENTION

Carotenoids represent one of the most widely distributed and structurally diverse classes of natural pigments, producing pigment colors of light yellow to orange to deep red color. Eye-catching examples of carotenogenic tissues include carrots, tomatoes, red peppers, and the petals of daffodils and marigolds. Carotenoids are synthesized by all photosynthetic organisms, as well as some bacteria and fungi. These pigments have important functions in photosynthesis, nutrition, and protection against photooxidative damage. For example, animals do not have the ability to synthesize carotenoids but must obtain these nutritionally important compounds through their dietary sources.

Industrially, only a few carotenoids are used for food colors, animal feeds, pharmaceuticals, and cosmetics, despite the existence of more than 600 different carotenoids identified in nature. This is largely due to difficulties in production. Presently, most of the carotenoids used for industrial purposes are produced by chemical synthesis; however, these compounds are very difficult to make chemically (Nelis and Leenheer, Journal of Appl Bacteriol. 70:181–191 (1991)). Natural carotenoids can either be obtained by extraction of plant material or by microbial synthesis; but, only a few plants are widely used for commercial carotenoid production and the productivity of carotenoid synthesis in these plants is relatively low. As a result, carotenoids produced from these plants are very expensive. One way to increase the productive capacity of biosynthesis would be to apply recombinant DNA technology (reviewed in Misawa and Shimada, *J. Biotech.* 59:169–181 (1998)). Thus, it would be desirable to produce carotenoids in non-carotenogenic bacteria and yeasts, thereby permitting control over quality, quantity and selection of the most suitable and efficient producer organisms. The latter is especially important for commercial production economics (and therefore availability) to consumers.

Structurally, the most common carotenoids are 40-carbon ($C_{40}$) terpenoids; however, carotenoids with only 30 carbon atoms ($C_{30}$; diapocarotenoids) are detected in some species. Biosynthesis of each of these types of carotenoids are derived from the isoprene biosynthetic pathway and its five-carbon universal isoprene building block, isopentenyl pyrophosphate (IPP). This biosynthetic pathway can be divided into two portions: 1) the upper isoprene pathway, which leads to the formation of farnesyl pyrophosphate (FPP); and 2) the lower carotenoid biosynthetic pathway, comprising various crt genes which convert FPP into long $C_{30}$ and $C_{40}$ carotenogenic compounds. Both portions of this pathway are shown in FIG. 1.

Typically, the formation of phytoene represents the first step unique to biosynthesis of $C_{40}$ carotenoids (FIGS. 1 and 2). Phytoene itself is a colorless carotenoid and occurs via isomerization of IPP to dimethylallyl pyrophosphate (DMAPP) by isopentenyl pyrophosphate isomerase (encoded by the gene idi). The reaction is followed by a sequence of 3 prenyltransferase reactions in which geranyl pyrophosphate (GPP), farnesyl pyrophosphate (FPP), and geranylgeranyl pyrophosphate (GGPP) are formed. The gene crtE, encoding GGPP synthetase, is responsible for this latter reaction. Finally, two molecules of GGPP condense to form phytoene (PPPP). This reaction is catalyzed by phytoene synthase (encoded by the gene crtB).

Lycopene is a "colored" carotenoid produced from phytoene. Lycopene imparts the characteristic red color of ripe tomatoes and has great utility as a food colorant. It is also an intermediate in the biosynthesis of other carotenoids in some bacteria, fungi and green plants. Lycopene is prepared biosynthetically from phytoene through four sequential dehydrogenation reactions by the removal of eight atoms of hydrogen, catalyzed by the gene crtI (encoding phytoene desaturase). Imtermediaries in this reaction are phytofluene, ζ-carotene, and neurosporene.

Lycopene cyclase (CrtY) converts lycopene to β-carotene. β-carotene is a typical carotene with a color spectrum ranging from yellow to orange. Its utility is as a colorant for margarine and butter, as a source for vitamin A production, and recently as a compound with potential preventative effects against certain kinds of cancers.

β-carotene is converted to zeaxanthin via a hydroxylation reaction resulting from the activity of β-carotene hydroxylase (encoded by the crtZ gene). For example, it is the yellow pigment which is present in the seeds of maize. Zeaxanthin is contained in feeds for hen or colored carp and is an important pigment source for their coloration.

In addition to the carotenoid biosynthetic genes and enzymes responsible for creation of phytoene, lycopene, β-carotene, and zeaxanthin, various other crt genes are known which enable the intramolecular conversion of $C_{40}$ compounds to produce numerous other functionalized carotenoid compounds by: (i) hydrogenation, (ii) dehydrogenation, (iii) cyclization, (iv) oxidation, (v) esterification/glycosylation, or any combination of these processes.

Many of the bacteria within the family Enterobacteriaceae are naturally pigmented, thus indicating the ability of these organisms to produce carotenoids. Furthermore, $C_{40}$ carotenoid biosynthesis has been particularly well-studied within the genus *Pantoea*, a small group of organisms previously classified within a broad group of bacteria all formerly known within the genus *Erwinia* [see Hauben et al., *Syst. Appl. Microbiol.* 21(3):384–397 (August 1998), for details concerning the reclassification of the large former genus *Erwinia* into four phylogenetic groups comprised of *Erwinia*, *Pectobacterium*, *Brenneria* gen. nov., and *Pantoea*]. For example, several reviews discuss the genetics of carotenoid pigment biosynthesis, such as those of G. Armstrong (*J. Bact.* 176: 4795–4802 (1994); *Annu. Rev. Microbiol.* 51:629–659 (1997)). Gene sequences encoding crtEXYIBZ are available for *Pantoea agglomerans* (formerly known as *E. herbicola* EHO-10 (ATCC #39368)), *P. ananatis* (formerly known as *E. uredovora* 20D3 (ATCC #19321)), *P. stewartii* (formerly known as *E. stewartii* (ATCC #8200)), and *P. agglomerans* pv. *milletiae* (U.S. Pat. No. 5,656,472; U.S. Pat. No. 5,545,816; U.S. Pat. No. 5,530,189; U.S. Pat. No. 5,530,188; U.S. Pat. No. 5,429,939; WO 02/079395 A2; see also GenBank® Accession Nos. M87280, D90087, AY166713, AB076662; respectively).

However, the existing literature provides limited information concerning gene sequences encoding crtEXYIBZ and the genetic organization of these sequences in organisms that are more distantly related to these well-characterized *Pantoea* species.

The problem to be solved, therefore, is to identify nucleic acid sequences encoding all or a portion of the carotenoid biosynthetic enzymes from organisms that are more distantly related to *Pantoea agglomerans* (ATCC #39368), *P. ananatis* ((ATCC #19321), *P. stewartii* ((ATCC #8200), and *P. agglomerans* pv. *milletiae* to facilitate studies to better understand carotenoid biosynthetic pathways, provide genetic tools for the manipulation of those pathways, and provide a means to synthesize carotenoids in large amounts by introducing and expressing the appropriate gene(s) in an appropriate host. This will lead to carotenoid production superior to synthetic methods.

Applicants have solved the stated problem by isolating six unique open reading frames (ORFs) in the carotenoid biosynthetic pathway encoding CrtE, Idi, CrtY, CrtI, CrtB and CrtZ enzymes from a yellow-pigmented bacterium designated as *Pantoea agglomerans* strain DC404. The genetic organization of these sequences is also novel.

SUMMARY OF THE INVENTION

The invention provides six genes, isolated from strain DC404 that have been demonstrated to be involved in the synthesis of various carotenoids including lycopene, β-carotene, and zeaxanthin. The genes are clustered on the same operon and include the crtE, idi, crtY, crtI, crtB and crtZ genes. The DNA sequences of the crtE, idi, crtY, crtI, crtB and crtZ coding sequences correspond to ORFs 1–6 and SEQ ID NOs:1, 3, 5, 7, 9 and 11, respectively.

Accordingly, the invention provides an isolated nucleic acid molecule encoding carotenoid biosynthetic pathway enzymes, wherein the genetic organization of the molecule is crtE-idi-crtY-crtI-crtB-crtZ, wherein the crtE, idi, crtY, crtI, crtB, and crtZ genes are clustered in the order stated and wherein the transcription of the crtZ occurs in opposite orientation to that of crtE, idi, crtY, crtI, and crtB.

In a preferred embodiment, at least one of the carotenoid biosynthetic pathway enzymes of the crtE-idi-crtY-crtI-crtB-crtZ gene cluster are encoded by the amino acid sequence selected from the group consisting of SEQ ID NOs:2, 4, 6, 8, 10, and 12. And, in a further preferred embodiment, the isolated acid molecule comprises a polynucleotide having the sequence as set forth in SEQ ID NO:18.

Similarly the invention provides an isolated nucleic acid molecule as set forth in SEQ ID NO:18, comprising the crtE-idi-crtY-crtI-crtB-crtZ, genes or an isolated nucleic acid molecule having at least 95% identity to SEQ ID NO:18, wherein the isolated nucleic acid molecule encodes all of the polypeptides crtE, idi, crtY, crtI, crtB, and crtZ.

Additionally, the invention provides an isolated nucleic acid molecule encoding a carotenoid biosynthetic pathway enzyme, selected from the group consisting of:
(a) an isolated nucleic acid molecule encoding the amino acid sequence selected from the group consisting of SEQ ID NOs:2, 4, 6, 8, 10, and 12;
(b) an isolated nucleic acid molecule that hybridizes with (a) under the following hybridization conditions: 0.1× SSC, 0.1% SDS, 65° C. and washed with 2×SSC, 0.1% SDS followed by 0.1×SSC, 0.1% SDS; and
(c) an isolated nucleic acid molecule that is complementary to (a) or (b).

The invention additionally provides polypeptides encoded by the instant genes and genetic chimera comprising suitable regulatory regions for genetic expression of the genes in bacteria, yeast, filamentous fungi, algae, and plants, as well as transformed hosts comprising the same.

The invention provides a method of obtaining a nucleic acid molecule encoding a carotenoid biosynthetic pathway enzyme comprising:
(a) probing a genomic library with the present nucleic acid molecules;
(b) identifying a DNA clone that hybridizes with the present nucleic acid molecules; and
(c) sequencing the genomic fragment that comprises the clone identified in step (b), wherein the sequenced genomic fragment encodes a carotenoid biosynthetic enzyme.

Similarly the invention provides a method of obtaining a nucleic acid molecule encoding a carotenoid biosynthetic pathway enzyme comprising:
(a) synthesizing at least one oligonucleotide primer corresponding to a portion of the present nucleic acid sequences; and
(b) amplifying an insert present in a cloning vector using the oligonucleotide primer of step (a);

wherein the amplified insert encodes a portion of an amino acid sequence encoding a carotenoid biosynthetic pathway enzyme.

In a preferred embodiment, the present invention provides a method for the production of carotenoid compounds comprising:
(a) providing a transformed host cell comprising:
  (i) suitable levels of farnesyl pyrophosphate; and
  (ii) a nucleic acid molecule encoding carotenoid biosynthetic pathway enzymes under the control of suitable regulatory sequences, wherein the genetic organization of the molecule is: crtE-idi-crtY-crtI-crtB-crtZ, wherein the crtE, idi, crtY, crtI, crtB, and crtZ genes are clustered in the order stated and wherein the transcription of the crtZ occurs in opposite orientation to that of crtE, idi, crtY, crtI, and crtB; and
(b) contacting the host cell of step (a) under suitable growth conditions with an effective amount of a fermentable carbon substrate whereby a carotenoid compound is produced.

Similarly, the invention additionally provides a set of nucleic acid molecules encoding the present carotenoid enzymes and genetic chimera comprising suitable regulatory regions for use in the production of carotenoid compounds.

In a specific preferred embodiment the invention provides a method for the production of carotenoid compounds in a C1 metabolizing host, for example a high growth methanotrophic bacterial strain such as *Methylomonas* 16a (ATCC designation PTA 2402), where the C1 metabolizing host:
(a) grows on a C1 carbon substrate selected from the group consisting of methane and methanol; and
(b) comprises a functional Embden-Meyerhof carbon pathway, said pathway comprising a gene encoding a pyrophosphate-dependent phosphofructokinase enzyme.

Additionally the invention provides a method of regulating carotenoid biosynthesis in an organism comprising overexpressing at least one carotenoid gene selected from the group consisting of SEQ ID NOs:1, 3, 5, 7, 9, and 11 in an organism such that the carotenoid biosynthesis is altered in the organism.

In an alternate embodiment the invention provides a mutated gene encoding a carotenoid biosynthetic pathway enzyme having an altered biological activity produced by a method comprising the steps of:
- (i) digesting a mixture of nucleotide sequences with restriction endonucleases wherein said mixture comprises:
  - a) an isolated nucleic acid molecule encoding a carotenoid biosynthetic pathway enzyme selected from the group consisting of SEQ ID NOs:1, 3, 5, 7, 9, and 11;
  - b) a first population of nucleotide fragments which will hybridize to said isolated nucleic acid molecules of step (a);
  - c) a second population of nucleotide fragments which will not hybridize to said isolated nucleic acid molecules of step (a);

wherein a mixture of restriction fragments are produced;
- (ii) denaturing said mixture of restriction fragments;
- (iii) incubating the denatured said mixture of restriction fragments of step (ii) with a polymerase;
- (iv) repeating steps (ii) and (iii) wherein a mutated carotenoid gene is produced encoding a protein having an altered biological activity.

In another embodiment the invention provides a *Pantoea agglomerans* strain DC404 comprising the 16s rDNA sequence as set forth in SEQ ID NO:16.

BRIEF DESCRIPTION OF THE DRAWINGS, SEQUENCE DESCRIPTIONS AND BIOLOGICAL DEPOSITS

Figure 3:
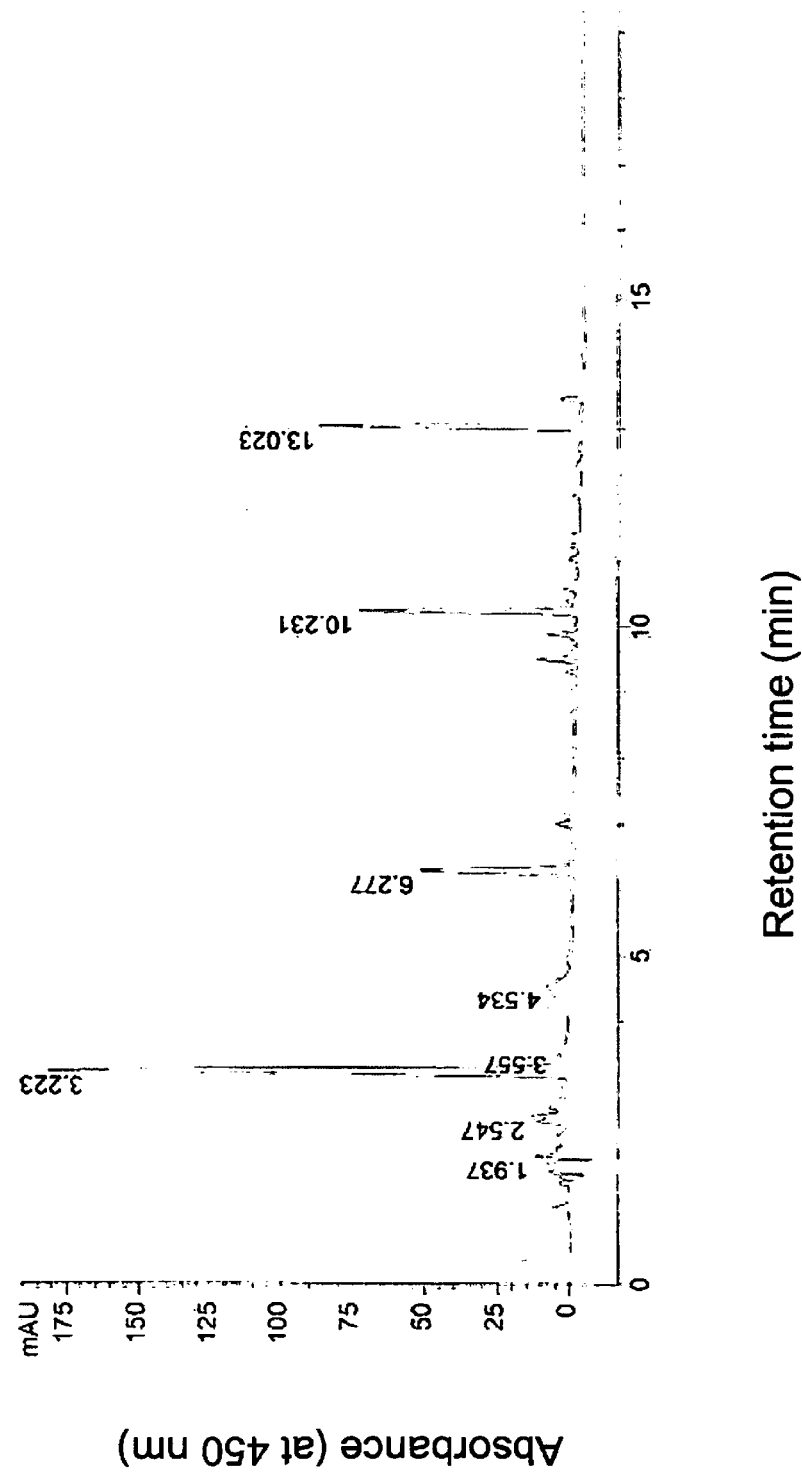

FIG. 3 presents results of an HPLC analysis of the carotenoids contained within *Pantoea agglomerans* strain DC404.

Figure 4:
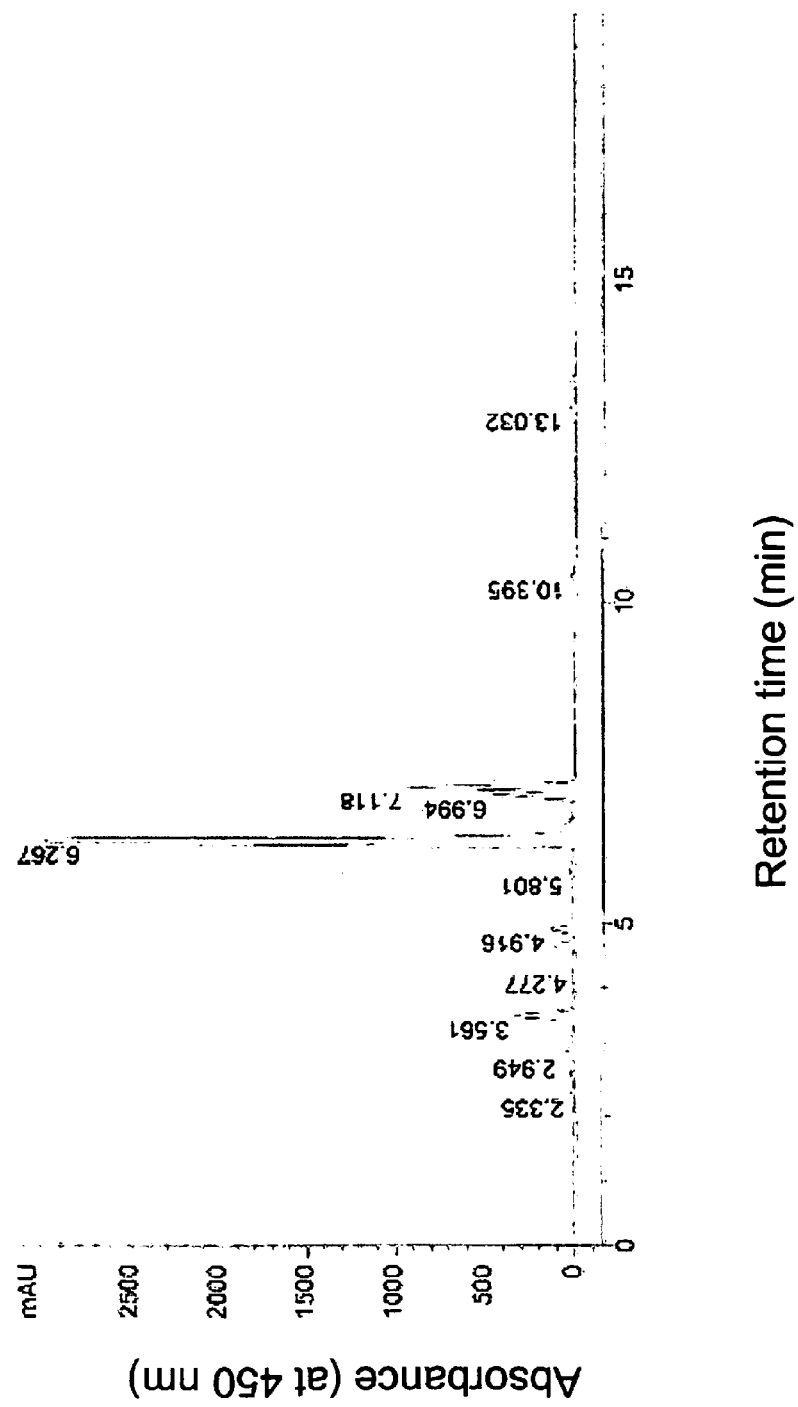

FIG. 4 presents results of an HPLC analysis of the carotenoids contained within transformant *E. coli* comprising cosmid pWEB-404.

Figure 5:
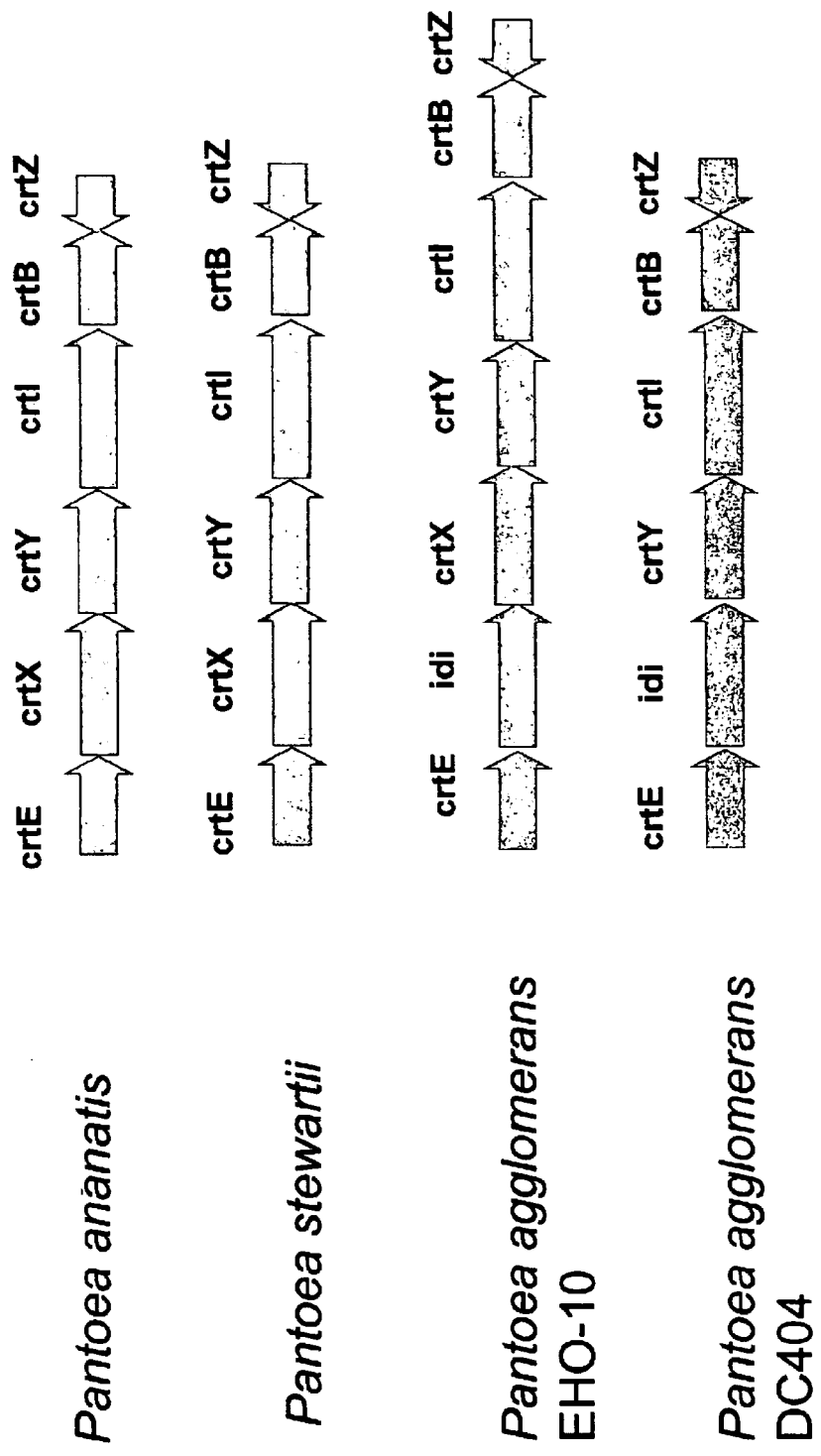

FIG. 5 shows a comparison of the organization of the carotenoid gene clusters of *Pantoea ananatis* (GenBank® Accession No. D90087), *Pantoea stewartii* (GenBank® Accession No. AY166713), *Pantoea agglomerans* EHO-10 (GenBank® Accession No. M87280), and *Pantoea agglomerans* DC404.

Figure 6:
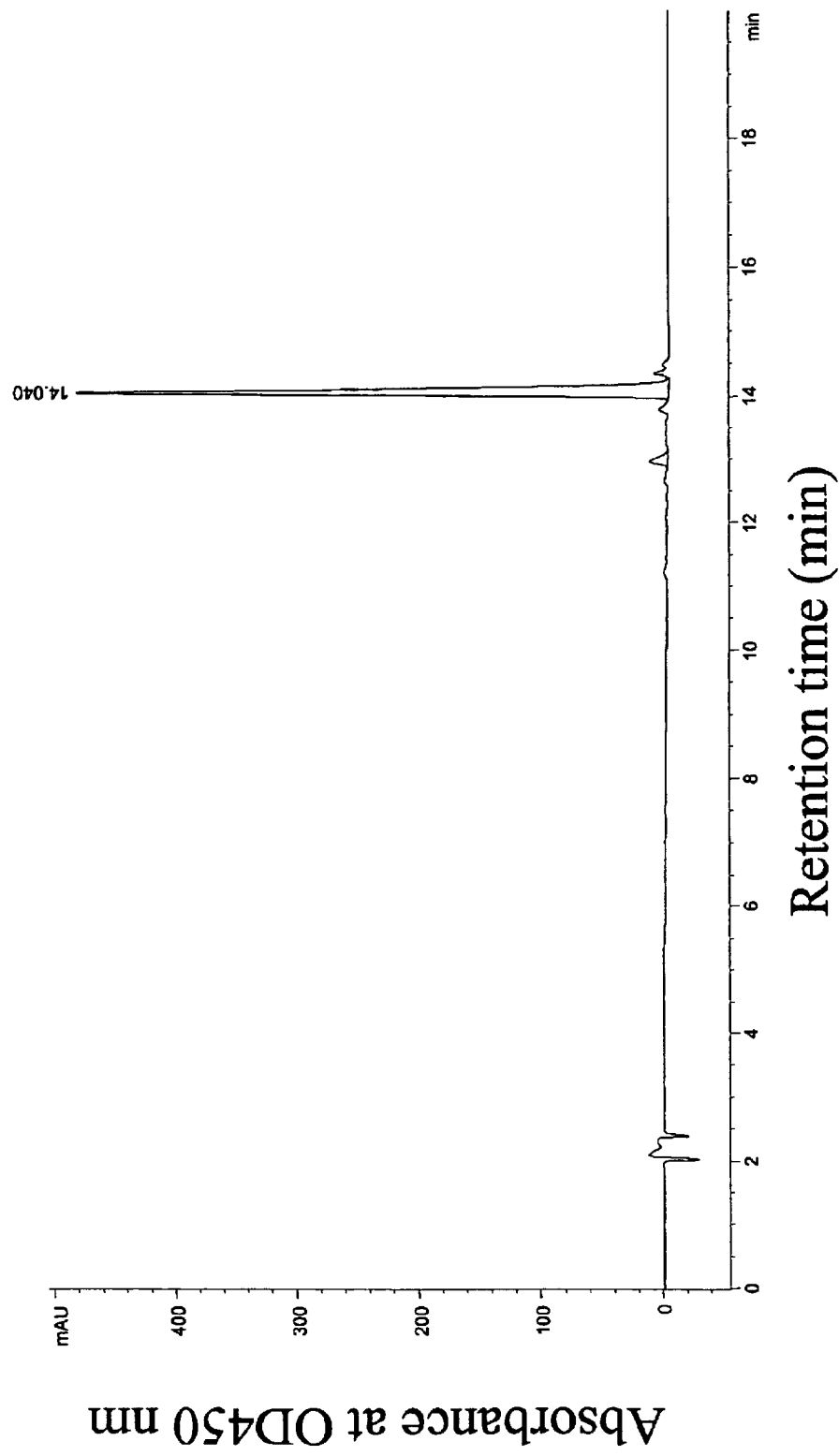

FIG. 6 shows the HPLC analysis of the carotenoids from *Methylomonas* 16a CrtN1⁻ strain containing pDCQ330.

The invention can be more fully understood from the following detailed description and the accompanying sequence descriptions which form a part of this application.

The following sequences conform with 37 C.F.R. 1.821–1.825 ("Requirements for Patent Applications Containing Nucleotide Sequences and/or Amino Acid Sequence Disclosures—the Sequence Rules") and consistent with World Intellectual Property Organization (WIPO) Standard ST.25 (1998) and the sequence listing requirements of the EPO and PCT (Rules 5.2 and 49.5(a-bis), and Section 208 and Annex C of the Administrative Instructions). The symbols and format used for nucleotide and amino acid sequence data comply with the rules set forth in 37 C.F.R. §1.822.

SEQ ID NOs:1–12 are full length genes or proteins as identified in Table 1.

TABLE 1

Summary of *Pantoea agglomerans* strain DC404 Gene and Protein SEQ ID Numbers

| Description | ORF No. | Nucleic acid SEQ ID NO. | Peptide SEQ ID NO. |
|---|---|---|---|
| crtE | 1 | 1 | 2 |
| idi | 2 | 3 | 4 |
| crtY | 3 | 5 | 6 |
| crtI | 4 | 7 | 8 |
| crtB | 5 | 9 | 10 |
| crtZ | 6 | 11 | 12 |

SEQ ID NOs:13–15, and 17 are the nucleotide sequences encoding primers HK12, JCR14, JCR15, and TET-1FP-1, respectively.

SEQ ID NO:16 provides the 16S rRNA gene sequence of strain DC404.

SEQ ID NO:18 is the nucleotide sequence of a 8,814 bp fragment of DNA from strain DC404 encoding the crtE, idi, crtY, crtI, crtB and crtZ genes.

SEQ ID NO:19 is the nucleotide sequence of primer pWEB404F.

SEQ ID NO:20 is the nucleotide sequence of primer pWEB404R.

Applicants made the following biological deposit under the terms of the Budapest Treaty on the International Recognition of the Deposit of Micro-organisms for the Purposes of Patent Procedure:

| Depositor Identification Reference | International Depository Designation | Date of Deposit |
|---|---|---|
| *Methylomonas* 16a | ATCC PTA 2402 | Aug. 22, 2000 |

As used herein, "ATCC" refers to the American Type Culture Collection International Depository Authority located at ATCC, 10801 University Blvd., Manassas, Va. 20110-2209, U.S.A. The "International Depository Designation" is the accession number to the culture on deposit with ATCC.

The listed deposit will be maintained in the indicated international depository for at least thirty (30) years and will be made available to the public upon the grant of a patent disclosing it. The availability of a deposit does not constitute a license to practice the subject invention in derogation of patent rights granted by government action.

DETAILED DESCRIPTION OF THE INVENTION

The genes of this invention and their expression products are useful for the creation of recombinant organisms that have the ability to produce various carotenoid compounds. Nucleic acid fragments encoding CrtE, Idi, CrtY, CrtI, CrtB, and CrtZ have been isolated from *Pantoea agglomerans* strain DC404 and identified by comparison to public databases containing nucleotide and protein sequences using the BLAST and FASTA algorithms well known to those skilled in the art. The genes and gene products of the present invention may be used in a variety of ways for the enhancement or manipulation of carotenoid compounds. Further advantages may be incurred as a result of the unique genetic organization of the gene cluster comprising these genes.

There is a general practical utility for microbial production of carotenoid compounds as these compounds are very difficult to make chemically (Nelis and Leenheer, supra). Most carotenoids have strong color and can be viewed as natural pigments or colorants. Furthermore, many carotenoids have potent antioxidant properties and thus inclusion of these compounds in the diet is thought to be healthful. Well-known examples are β-carotene, canthaxanthin, and astaxanthin. Additionally, carotenoids are required elements of aquaculture. Salmon and shrimp aquacultures are particularly useful applications for this invention as carotenoid pigmentation is critically important for the value of these organisms (Shahidi, F., and Brown, J. A., *Critical reviews in Food Science* 38(1): 1–67 (1998)). Finally, carotenoids have utility as intermediates in the synthesis of steroids, flavors and fragrances and compounds with potential electro-optic applications.

The disclosure below provides a detailed description of the isolation of carotenoid synthesis genes from *Pantoea agglomerans* strain DC404, modification of these genes by genetic engineering, and their insertion into compatible plasmids suitable for cloning and expression in *E. coli*, bacteria, yeasts, fungi and higher plants.

Definitions

In this disclosure, a number of terms and abbreviations are used.

The following definitions are provided.

"Open reading frame" is abbreviated ORF.

"Polymerase chain reaction" is abbreviated PCR.

"High Performance Liquid Chromatography" is abbreviated HPLC.

The term "isoprenoid compound" refers to compounds formally derived from isoprene (2-methylbuta-1,3-diene; $CH_2=C(CH_3)CH=CH_2$), the skeleton of which can generally be discerned in repeated occurrence in the molecule. These compounds are produced biosynthetically via the isoprenoid pathway beginning with isopentenyl pyrophosphate (IPP) and formed by the head-to-tail condensation of isoprene units, leading to molecules which may be—for example—of 5, 10, 15, 20, 30, or 40 carbons in length.

Figure 1:
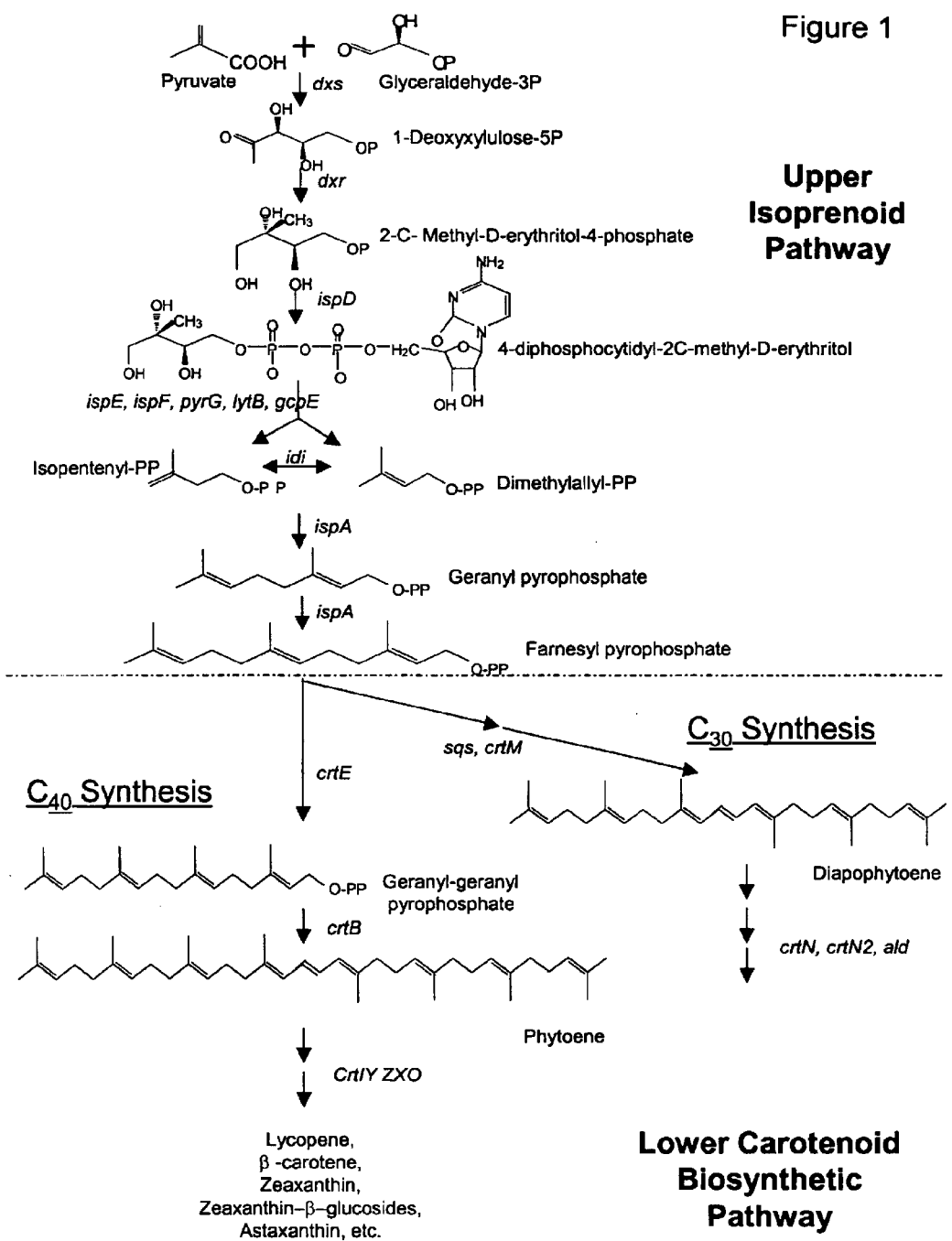
FIG. 1 shows the upper isoprenoid and lower carotenoid biosynthetic pathways.

The term "carotenoid biosynthetic pathway" refers to those genes comprising members of the upper isoprenoid pathway and/or lower carotenoid biosynthetic pathway of the present invention, as illustrated in FIG. 1.

The terms "upper isoprenoid pathway" and "upper pathway" will be use interchangeably and will refer to enzymes involved in converting pyruvate and glyceraldehyde-3-phosphate to farnesyl pyrophosphate (FPP). These enzymes include, but are not limited to: the "dxs"gene (encoding 1-deoxyxylulose-5-phosphate synthase); the "dxr" gene (encoding 1-deoxyxylulose-5-phosphate reductoisomerase); the "ispD" gene (encoding a 2C-methyl-D-erythritol cytidyltransferase enzyme; also known as ygbP); the "ispE" gene (encoding 4-diphosphocytidyl-2-C-methylerythritol kinase; also known as ychB); the "ispF" gene (encoding a 2C-methyl-D-erythritol 2,4-cyclodiphosphate synthase; also known as ygbB); the "pyrG" gene (encoding a CTP synthase); the "lytB" gene involved in the formation of dimethylallyl diphosphate; the "gcpE" gene involved in the synthesis of 2-C-methyl-D-erythritol 4-phosphate; the "idi" gene (responsible for the intramolecular conversion of IPP to dimethylallyl pyrophosphate); and the "ispA" gene (encoding geranyltransferase or farnesyl diphosphate synthase) in the isoprenoid pathway.

The term "Idi" refers to an isopentenyl diphosphate isomerase enzyme (E.C. 5.3.3.2) encoded by the idi gene. A representative idi gene is provided as SEQ ID NO:3.

The terms "lower carotenoid biosynthetic pathway" and "lower pathway" will be used interchangeably and refer to those enzymes which convert FPP to a suite of carotenoids. These include those genes and gene products that are involved in the immediate synthesis of either diapophytoene (whose synthesis represents the first step unique to biosynthesis of $C_{30}$ carotenoids) or phytoene (whose synthesis represents the first step unique to biosynthesis of $C_{40}$ carotenoids). All subsequent reactions leading to the production of various $C_{30}$–$C_{40}$ carotenoids are included within the lower carotenoid biosynthetic pathway. These genes and gene products comprise all of the "crt" genes including, but not limited to: crtM, crtN, crtN2, crtE, crtX, crtY, crtI, crtB, crtZ, crtW, crtO, crtA, crtC, crtD, crtF, and crtU. Finally, the term "lower carotenoid biosynthetic enzyme" is an inclusive term referring to any and all of the enzymes in the present lower pathway including, but not limited to: CrtM, CrtN, CrtN2, CrtE, CrtX, CrtY, CrtI, CrtB, CrtZ, CrtW, CrtO, CrtA, CrtC, CrtD, CrtF, and CrtU.

For the present application, the term "carotenoid compound" is defined as a class of hydrocarbons having a conjugated polyene carbon skeleton formally derived from isoprene. This class of molecules is composed of triterpenes ($C_{30}$ diapocarotenoids) and tetraterpenes ($C_{40}$ carotenoids) and their oxygenated derivatives; and, these molecules typically have strong light absorbing properties and may range in length in excess of $C_{200}$. Other "carotenoid compounds" are known which are $C_{35}$, $C_{50}$, $C_{60}$, $C_{70}$, and $C_{80}$ in length, for example.

"$C_{30}$ diapocarotenoids" consist of six isoprenoid units joined in such a manner that the arrangement of isoprenoid units is reversed at the center of the molecule so that the two central methyl groups are in a 1,6-positional relationship and the remaining nonterminal methyl groups are in a 1,5-positional relationship. All $C_{30}$ carotenoids may be formally derived from the acyclic $C_{30}H_{42}$ structure, having a long central chain of conjugated double bonds, by: (i) hydrogenation (ii) dehydrogenation, (iii) cyclization, (iv) oxidation, (v) esterification/glycosylation, or any combination of these processes.

"Tetraterpenes" or "$C_{40}$ carotenoids" consist of eight isoprenoid units joined in such a manner that the arrangement of isoprenoid units is reversed at the center of the molecule so that the two central methyl groups are in a 1,6-positional relationship and the remaining nonterminal methyl groups are in a 1,5-positional relationship. All $C_{40}$ carotenoids may be formally derived from the acyclic $C_{40}H_{56}$ structure (Formula I below), having a long central chain of conjugated double bonds, by (i) hydrogenation, (ii) dehydrogenation, (iii) cyclization, (iv) oxidation, (v) esterification/glycosylation, or any combination of these processes. This class also includes certain compounds that arise from rearrangements of the carbon skeleton (Formula I), or by the (formal) removal of part of this structure.

Formula I

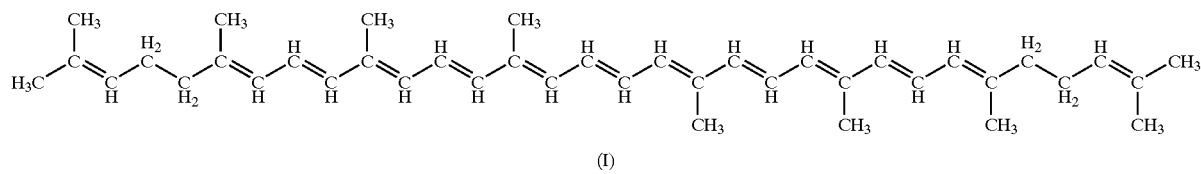

(I)

For convenience, carotenoid formulae are often written in a shorthand form as (Formula IA below):

Formula IA

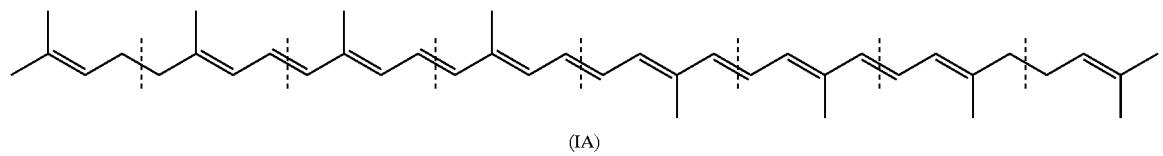

(IA)

where the broken lines indicate formal division into isoprenoid units.

The term "functionalized" or "functionalization" refers to the (i) hydrogenation, (ii) dehydrogenation, (iii) cyclization, (iv) oxidation, or (v) esterification/glycosylation of any portion of the carotenoid backbone. This backbone is defined as the long central chain of conjugated double bonds. Functionalization may also occur by any combination of the above processes.

The term "CrtE" refers to a geranylgeranyl pyrophosphate synthase enzyme encoded by the crtE gene and which converts trans-trans-farnesyl diphosphate and isopentenyl diphosphate to pyrophosphate and geranylgeranyl diphosphate. A representative crtE gene is provided as SEQ ID NO:1.

The term "CrtY" refers to a lycopene cyclase enzyme encoded by the crtY gene which converts lycopene to β-carotene. A representative crtY gene is provided as SEQ ID NO:5.

The term "CrtI" refers to a phytoene desaturase enzyme encoded by the crtI gene. CrtI converts phytoene into lycopene via the intermediaries of phytofluene, ζ-carotene and neurosporene by the introduction of 4 double bonds. A representative crtI gene is provided as SEQ ID NO:7.

The term "CrtB" refers to a phytoene synthase enzyme encoded by the crtB gene which catalyzes the reaction from prephytoene diphosphate to phytoene. A representative crtB gene is provided as SEQ ID NO:9.

The term "CrtZ" refers to a β-carotene hydroxylase enzyme encoded by the crtZ gene which catalyzes a hydroxylation reaction from β-carotene to zeaxanthin. A representative crtZ gene is provided as SEQ ID NO:11.

The term "CrtX" refers to a zeaxanthin glucosyl transferase enzyme encoded by the crtX gene and which converts zeaxanthin to zeaxanthin-β-diglucoside.

The term "genetic organization" refers to the order and the orientation in which ORFs are organized on a single nucleic acid fragment. In the present application, the genetic organization of 3 different clusters of DNA are described, each of which is defined below:

1. The term "crtE-idi-crtY-crtI-crtB-crtZ" or "crtE-idi-crtYIBZ" refers to a molecule having the following genetic organization: the crtE, idi, crtY, crtI, crtB, and crtZ genes are clustered in the order stated and the transcription of the crtZ occurs in opposite orientation to that of crtE, idi, crtY, crtI, and crtB.

2. The term "crtE-crtX-crtY-crtI-crtB-crtZ" or "crtEXYIBZ" refers to a molecule having the following genetic organization: the crtE, crtX, crtY, crtI, crtB, and crtZ genes are clustered in the order stated and the transcription of the crtZ occurs in opposite orientation to that of crtE, crtX, crtY, crtI, and crtB.

3. The term "crtE-idi-crtX-crtY-crtI-crtB-crtZ" or "cdE-idi-crtXYIBZ" refers to a molecule having the following genetic organization: the crtE, idi, crtX, crtY, crtI, crtB, and crtZ genes are clustered in the order stated and the transcription of the crtZ occurs in opposite orientation to that of crtE, idi, crtX, crtY, crtI, and crtB.

The term "Embden-Meyerhof pathway" refers to the series of biochemical reactions for conversion of hexoses such as glucose and fructose to important cellular 3-carbon intermediates such as glyceraldehyde 3-phosphate, dihydroxyacetone phosphate, phosphoenol pyruvate and pyruvate. These reactions typically proceed with net yield of biochemically useful energy in the form of ATP. The key enzymes unique to the Embden-Meyerof pathway are the phosphofructokinase and fructose 1,6 bisphosphate aldolase.

The term "Entner-Douderoff pathway" refers to a series of biochemical reactions for conversion of hexoses such as glucose or fructose to the important 3-carbon cellular intermediates pyruvate and glyceraldehyde 3-phosphate without any net production of biochemically useful energy. The key enzymes unique to the Entner-Douderoff pathway are 6-phosphogluconate dehydratase and a ketodeoxyphosphogluconate aldolase.

The term "$C_1$ carbon substrate" or "single carbon substrate" refers to any carbon-containing molecule that lacks a carbon-carbon bond. Examples are methane, methanol, formaldehyde, formic acid, formate, methylated amines (e.g., mono-, di-, and tri-methyl amine), methylated thiols, and carbon dioxide.

The term "$C_1$ metabolizer" refers to a microorganism that has the ability to use a single carbon substrate as its sole source of energy and biomass. $C_1$ metabolizers will typically be methylotrophs and/or methanotrophs.

The term "methylotroph" means an organism capable of oxidizing organic compounds that do not contain carbon-carbon bonds. Where the methylotroph is able to oxidize $CH_4$, the methylotroph is also a methanotroph.

The term "methanotroph" or "methanotrophic bacteria" means a prokaryote capable of utilizing methane as its primary source of carbon and energy. Complete oxidation of methane to carbon dioxide occurs by aerobic degradation pathways. Typical examples of methanotrophs useful in the present invention include (but are not limited to) the genera *Methylomonas, Methylobacter, Methylococcus,* and *Methylosinus.*

The term "high growth methanotrophic bacterial strain" refers to a bacterium capable of growth with methane or methanol as the sole carbon and energy source and which possesses a functional Embden-Meyerof carbon flux pathway resulting in a high rate of growth and yield of cell mass per gram of $C_1$ substrate metabolized. The specific "high growth methanotrophic bacterial strain" described herein is referred to as "*Methylomonas* 16a", "16a" or "*Methylomonas* sp. 16a", which terms are used interchangeably and which refer to the *Methylomonas* sp. 16a (ATCC PTA-2402) strain (U.S. Pat. No. 6,689,601).

The term "crt gene cluster" in *Methylomonas* refers to an open reading frame comprising crtN1, ald, and crtN2, that is active in the native carotenoid biosynthetic pathway of *Methylomonas* sp. 16a.

The term "CrtN1" refers to an enzyme encoded by the crtN1 gene, active in the native carotenoid biosynthetic pathway of *Methylomonas* sp. 16a. This gene is the first gene located on the crt gene cluster in *Methylomonas.*

The term "ALD" refers to an enzyme encoded by the ald gene, active in the native carotenoid biosynthetic pathway of *Methylomonas* sp. 16a. This gene is the second gene located on the crt gene cluster in *Methylomonas.* The term "CrtN2" refers to an enzyme encoded by the crtN2 gene, active in the native carotenoid biosynthetic pathway of *Methylomonas* sp. 16a. This gene is the third gene located on the crt gene cluster in *Methylomonas.*

The term "CrtN3" refers to an enzyme encoded by the crtN3 gene, which affects the native carotenoid biosynthesis in *Methylomonas* sp. 16a. This gene is not located within the crt gene cluster; instead this gene is present in a different locus within the *Methylomonas* genome (WO 02/18617).

The term "pigmentless" or "white mutant" or "non-pigmented strain" refers to a *Methylomonas* sp. 16a bacterium wherein the native pink pigment (e.g., a $C_{30}$ carotenoid) is not produced. Thus, the bacterial cells appear white in color, as opposed to pink. *Methylomonas* sp. 16a white mutants have been engineered by deleting all or a portion of the native $C_{30}$ carotenoid genes. For example, disruption of either the ald/crtN1 genes or the promoter driving the native crt gene cluster in *Methylomonas* sp. 16a creates a non-pigmented ("white") mutant better suited for $C_{40}$ carotenoid production (WO 02/18617).

The term "*Methylomonas* sp. 16a MWM1000" or "MWM1000" refers to a non-pigmented methanotropic bacterial strain created by deleting a portion of the ald and crtN1 genes native to *Methylomonas* sp. 16a (WO 02/18617). The deletion disrupted $C_{30}$ carotenoid production in MWM1100. The ald/crtN1 deletion is denoted as "Δald/crtN1".

As used herein, an "isolated nucleic acid fragment" is a polymer of RNA or DNA that is single- or double-stranded, optionally containing synthetic, non-natural or altered nucleotide bases. An isolated nucleic acid fragment in the form of a polymer of DNA may be comprised of one or more segments of cDNA, genomic DNA or synthetic DNA.

A nucleic acid molecule is "hybridizable" to another nucleic acid molecule, such as a cDNA, genomic DNA, or RNA molecule, when a single-stranded form of the nucleic acid molecule can anneal to the other nucleic acid molecule under the appropriate conditions of temperature and solution ionic strength. Hybridization and washing conditions are well known and exemplified in Sambrook, J., Fritsch, E. F. and Maniatis, T. *Molecular Cloning: A Laboratory Manual,* $2^{nd}$ ed., Cold Spring Harbor Laboratory: Cold Spring Harbor, N.Y. (1989), particularly Chapter 11 and Table 11.1 therein (hereinafter "Maniatis"). The conditions of temperature and ionic strength determine the "stringency" of the hybridization. Stringency conditions can be adjusted to screen for moderately similar fragments (such as homologous sequences from distantly related organisms), to highly similar fragments (such as genes that duplicate functional enzymes from closely related organisms). Post-hybridization washes determine stringency conditions. One set of preferred conditions uses a series of washes starting with 6×SSC, 0.5% SDS at room temperature for 15 min, then repeated with 2×SSC, 0.5% SDS at 45° C. for 30 min, and then repeated twice with 0.2×SSC, 0.5% SDS at 50° C. for 30 min. A more preferred set of stringent conditions uses higher temperatures in which the washes are identical to those above except for the temperature of the final two 30 min washes in 0.2×SSC, 0.5% SDS was increased to 60° C. Another preferred set of highly stringent conditions uses two final washes in 0.1×SSC, 0.1% SDS at 65° C. An additional set of stringent conditions include hybridization at 0.1×SSC, 0.1% SDS, 65° C. and washed with 2×SSC, 0.1% SDS followed by 0.1×SSC, 0.1% SDS, for example.

Hybridization requires that the two nucleic acids contain complementary sequences, although depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the greater the value of Tm for hybrids of nucleic acids having those sequences. The relative stability (corresponding to higher Tm) of nucleic acid hybridizations decreases in the following order: RNA:RNA, DNA:RNA, DNA:DNA. For hybrids of greater than 100 nucleotides in length, equations for calculating Tm have been derived (see Sambrook et al., supra, 9.50–9.51). For hybridizations with shorter nucleic acids, i.e., oligonucleotides, the position of mismatches becomes more important, and the length of the oligonucleotide determines its specificity (see Sambrook et al., supra, 11.7–11.8). In one embodiment, the length for a hybridizable nucleic acid is at least about 10 nucleotides. Preferably a minimum length for a hybridizable nucleic acid is at least about 15 nucleotides; more preferably at least about 20 nucleotides; and most preferably the length is at least about 30 nucleotides. Furthermore, the skilled artisan will recognize that the temperature and wash solution salt concentration may be adjusted as necessary according to factors such as length of the probe.

A "substantial portion" of an amino acid or nucleotide sequence is that portion comprising enough of the amino acid sequence of a polypeptide or the nucleotide sequence of a gene to putatively identify that polypeptide or gene, either by manual evaluation of the sequence by one skilled in the art, or by computer-automated sequence comparison and identification using algorithms such as BLAST (Basic Local Alignment Search Tool; Altschul, S. F., et al., *J. Mol. Biol.* 215:403–410 (1993)). In general, a sequence of ten or more contiguous amino acids or thirty or more nucleotides is necessary in order to putatively identify a polypeptide or nucleic acid sequence as homologous to a known protein or gene. Moreover, with respect to nucleotide sequences, gene specific oligonucleotide probes comprising 20–30 contiguous nucleotides may be used in sequence-dependent methods of gene identification (e.g., Southern hybridization) and isolation (e.g., in situ hybridization of bacterial colonies or bacteriophage plaques). In addition, short oligonucleotides of 12–15 bases may be used as amplification primers in PCR in order to obtain a particular nucleic acid fragment comprising the primers. Accordingly, a "substantial portion" of a nucleotide sequence comprises enough of the sequence to specifically identify and/or isolate a nucleic acid fragment comprising the sequence. The instant specification teaches partial or complete amino acid and nucleotide sequences encoding one or more particular microbial proteins. The skilled artisan, having the benefit of the sequences as reported herein, may now use all or a substantial portion of the disclosed sequences for purposes known to those skilled in this art. Accordingly, the instant invention comprises the complete sequences as reported in the accompanying Sequence Listing, as well as substantial portions of those sequences as defined above.

The term "complementary" is used to describe the relationship between nucleotide bases that are capable of hybridizing to one another. For example, with respect to DNA, adenosine is complementary to thymine and cytosine is complementary to guanine. Accordingly, the instant invention also includes isolated nucleic acid fragments that are complementary to the complete sequences as reported in the accompanying Sequence Listing, as well as those substantially similar nucleic acid sequences.

The term "percent identity", as known in the art, is a relationship between two or more polypeptide sequences or two or more polynucleotide sequences, as determined by comparing the sequences. In the art, "identity" also means the degree of sequence relatedness between polypeptide or polynucleotide sequences, as the case may be, as determined by the match between strings of such sequences. "Identity" and "similarity" can be readily calculated by known methods, including but not limited to those described in: 1.) *Computational Molecular Biology* (Lesk, A. M., Ed.) Oxford University: NY (1988); 2.) *Biocomputing: Informatics and Genome Projects* (Smith, D. W., Ed.) Academic: NY (1993); 3.) *Computer Analysis of Sequence Data, Part I* (Griffin, A. M., and Griffin, H. G., Eds.) Humana: NJ (1994); 4.) *Sequence Analysis in Molecular Biology* (von Heinje, G., Ed.) Academic (1987); and 5.) *Sequence Analysis Primer* (Gribskov, M. and Devereux, J., Eds.) Stockton: NY (1991). Preferred methods to determine identity are designed to give the best match between the sequences tested. Methods to determine identity and similarity are codified in publicly available computer programs. Sequence alignments and percent identity calculations may be performed using the Megalign program of the LASERGENE bioinformatics computing suite (DNASTAR Inc., Madison, Wis.). Multiple alignment of the sequences is performed using the Clustal method of alignment (Higgins and Sharp, *CABIOS.* 5:151–153 (1989)) with default parameters (GAP PENALTY=10, GAP LENGTH PENALTY=10). Default parameters for pairwise alignments using the Clustal method are: KTUPLE 1, GAP PENALTY=3, WINDOW=5 and DIAGONALS SAVED=5.

Suitable nucleic acid fragments (isolated polynucleotides of the present invention) encode polypeptides that are at least about 70% identical, preferably at least about 75% identical, and more preferably at least about 80% identical to the amino acid sequences reported herein. Preferred nucleic acid fragments encode amino acid sequences that are about 85% identical to the amino acid sequences reported herein. More preferred nucleic acid fragments encode amino acid sequences that are at least about 90% identical to the amino acid sequences reported herein. Most preferred are nucleic acid fragments that encode amino acid sequences that are at least about 95% identical to the amino acid sequences reported herein. Suitable nucleic acid fragments not only have the above homologies but typically encode a polypeptide having at least 50 amino acids, preferably at least 100 amino acids, more preferably at least 150 amino acids, still more preferably at least 200 amino acids, and most preferably at least 250 amino acids.

"Codon degeneracy" refers to the nature in the genetic code permitting variation of the nucleotide sequence without effecting the amino acid sequence of an encoded polypeptide. Accordingly, the instant invention relates to any nucleic acid fragment that encodes all or a substantial portion of the amino acid sequence encoding the instant microbial polypeptides as set forth in SEQ ID NOs:2, 4, 6, 8, 10, and 12. The skilled artisan is well aware of the "codon-bias" exhibited by a specific host cell in usage of nucleotide codons to specify a given amino acid. Therefore, when synthesizing a gene for improved expression in a host cell, it is desirable to design the gene such that its frequency of codon usage approaches the frequency of preferred codon usage of the host cell.

"Synthetic genes" can be assembled from oligonucleotide building blocks that are chemically synthesized using procedures known to those skilled in the art. These building blocks are ligated and annealed to form gene segments which are then enzymatically assembled to construct the entire gene. "Chemically synthesized", as related to a sequence of DNA, means that the component nucleotides were assembled in vitro. Manual chemical synthesis of DNA may be accomplished using well-established procedures, or automated chemical synthesis can be performed using one of a number of commercially available machines. Accordingly, the genes can be tailored for optimal gene expression based on optimization of nucleotide sequence to reflect the codon bias of the host cell. The skilled artisan appreciates the likelihood of successful gene expression if codon usage is biased towards those codons favored by the host. Determination of preferred codons can be based on a survey of genes derived from the host cell where sequence information is available.

"Gene" refers to a nucleic acid fragment that expresses a specific protein, including regulatory sequences preceding (5' non-coding sequences) and following (3' non-coding sequences) the coding sequence. "Native gene" refers to a gene as found in nature with its own regulatory sequences. "Chimeric gene" refers to any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign" gene refers to a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure.

"Coding sequence" refers to a DNA sequence that codes for a specific amino acid sequence. "Suitable regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, polyadenylation recognition sequences, RNA processing sites, effector binding sites and stem-loop structures.

"Promoter" refers to a DNA sequence capable of controlling the expression of a coding sequence or functional RNA. In general, a coding sequence is located 3' to a promoter sequence. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental or physiological conditions. Promoters that cause a gene to be expressed in most cell types at most times are commonly referred to as "constitutive promoters". It is further recognized that since in most cases the exact boundaries of regulatory sequences have not been completely defined, DNA fragments of different lengths may have identical promoter activity.

The "3' non-coding sequences" refer to DNA sequences located downstream of a coding sequence and include polyadenylation recognition sequences (normally limited to eukaryotes) and other sequences encoding regulatory signals capable of affecting mRNA processing or gene expression. The polyadenylation signal is usually characterized by affecting the addition of polyadenylic acid tracts to the 3' end of the mRNA precursor.

"RNA transcript" refers to the product resulting from RNA polymerase-catalyzed transcription of a DNA sequence. When the RNA transcript is a perfect complementary copy of the DNA sequence, it is referred to as the primary transcript or it may be a RNA sequence derived from post-transcriptional processing of the primary transcript and is referred to as the mature RNA. "Messenger RNA" or "mRNA" refers to the RNA that is without introns and that can be translated into protein by the cell. "cDNA" refers to a double-stranded DNA that is complementary to and derived from mRNA. "Sense" RNA refers to RNA transcript that includes the mRNA and so can be translated into protein by the cell. "Antisense RNA" refers to a RNA transcript that is complementary to all or part of a target primary transcript or mRNA and that blocks the expression of a target gene (U.S. Pat. No. 5,107,065; WO 99/28508). The complementarity of an antisense RNA may be with any part of the specific gene transcript, i.e., at the 5' non-coding sequence, 3' non-coding sequence, or the coding sequence. "Functional RNA" refers to antisense RNA, ribozyme RNA, or other RNA that is not translated yet has an effect on cellular processes.

The term "operably linked" refers to the association of nucleic acid sequences on a single nucleic acid fragment so that the function of one is affected by the other. For example, a promoter is operably linked with a coding sequence when it is capable of affecting the expression of that coding sequence (i.e., the coding sequence is under the transcriptional control of the promoter). Coding sequences can be operably linked to regulatory sequences in sense or antisense orientation.

The term "expression", as used herein, refers to the transcription and stable accumulation of sense (mRNA) or antisense RNA derived from the nucleic acid fragment of the invention. Expression may also refer to translation of mRNA into a polypeptide.

"Mature" protein refers to a post-translationally processed polypeptide; i.e., one from which any pre- or propeptides present in the primary translation product have been removed. "Precursor" protein refers to the primary product of translation of mRNA; i.e., with pre- and propeptides still present. Pre- and propeptides may be (but are not limited to) intracellular localization signals.

The term "signal peptide" refers to an amino terminal polypeptide preceding the secreted mature protein. The signal peptide is cleaved from, and is therefore not present in, the mature protein. Signal peptides have the function of directing and translocating secreted proteins across cell membranes. A signal peptide is also referred to as a signal protein.

"Conjugation" refers to a particular type of transformation in which a unidirectional transfer of DNA (e.g., from a bacterial plasmid) occurs from one bacterium cell (i.e., the "donor") to another (i.e., the "recipient"). The process involves direct cell-to-cell contact. Sometimes another bacterial cell (i.e., the "helper") is present to facilitate the conjugation.

"Transformation" refers to the transfer of a nucleic acid fragment into the genome of a host organism, resulting in genetically stable inheritance. Host organisms containing the transformed nucleic acid fragments are referred to as "transgenic", "recombinant" or "transformed" organisms.

The terms "plasmid", "vector" and "cassette" refer to an extra chromosomal element often carrying genes which are not part of the central metabolism of the cell, and usually in the form of circular double-stranded DNA fragments. Such elements may be autonomously replicating sequences, genome integrating sequences, phage or nucleotide sequences, linear or circular, of a single- or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequences into a cell. "Transformation cassette" refers to a specific vector containing a foreign gene and having elements in addition to the foreign gene that facilitate transformation of a particular host cell. "Expression cassette" refers to a specific vector containing a foreign gene and having elements in addition to the foreign gene that allow for enhanced expression of that gene in a foreign host.

The term "altered biological activity" will refer to an activity, associated with a protein encoded by a nucleotide sequence which can be measured by an assay method, where that activity is either greater than or less than the activity associated with the native sequence. "Enhanced biological activity" refers to an altered activity that is greater than that associated with the native sequence. "Diminished biological activity" is an altered activity that is less than that associated with the native sequence.

The term "sequence analysis software" refers to any computer algorithm or software program that is useful for the analysis of nucleotide or amino acid sequences. "Sequence analysis software" may be commercially available or independently developed. Typical sequence analysis software will include, but is not limited to: 1.) the GCG suite of programs (Wisconsin Package Version 9.0, Genetics Computer Group (GCG), Madison, Wis.); 2.) BLASTP, BLASTN, BLASTX (Altschul et al., *J. Mol. Biol.* 215:403–410 (1990)); 3.) DNASTAR (DNASTAR, Inc.

Madison, Wis.); and 4.) the FASTA program incorporating the Smith-Waterman algorithm (W. R. Pearson, *Comput. Methods Genome Res.*, [Proc. Int. Symp.] (1994), Meeting Date 1992, 111–20. Editor(s): Suhai, Sandor. Plenum: New York, N.Y.). 5.) the Vector NTI programs (InforMax, Inc., Bethesda, Md.). Within the context of this application it will be understood that where sequence analysis software is used for analysis, that the results of the analysis will be based on the "default values" of the program referenced, unless otherwise specified. As used herein "default values" will mean any set of values or parameters (set by the software manufacturer) which originally load with the software when first initialized.

Standard recombinant DNA and molecular cloning techniques used herein are well known in the art and are described by Maniatis (supra); by Silhavy, T. J., Bennan, M. L. and Enquist, L. W., *Experiments with Gene Fusions*, Cold Spring Harbor Laboratory: Cold Spring Harbor, N.Y. (1984); and by Ausubel, F. M. et al., *Current Protocols in Molecular Biology*, published by Greene Publishing Assoc. and Wiley-Interscience (1987).

Genes Involved in Carotenoid Production

The enzyme pathway involved in the biosynthesis of carotenoid compounds can be conveniently viewed in two parts, the upper isoprenoid pathway providing for the conversion of pyruvate and glyceraldehyde-3-phosphate to farnesyl pyrophosphate and the lower carotenoid biosynthetic pathway, which provides for the synthesis of either diapophytoene or phytoene and all subsequently produced carotenoids (FIG. 1). The upper pathway is ubiquitous in many microorganisms and in these cases it may only be necessary to introduce genes that comprise the lower pathway for biosynthesis of the desired carotenoid. The division between the two pathways concerns the synthesis of farnesyl pyrophosphate (FPP). Where FPP is naturally present, only elements of the lower carotenoid biosynthetic pathway will be needed. However, it will be appreciated that for the lower pathway carotenoid genes to be effective in the production of carotenoids, it will be necessary for the host cell to have suitable levels of FPP within the cell. Where FPP synthesis is not provided by the host cell, it will be necessary to introduce the genes necessary for the production of FPP. Each of these pathways will be discussed below in detail.

The Upper Isoprenoid Pathway

Isoprenoid biosynthesis occurs through either of two pathways, generating the common $C_5$ isoprene subunit, isopentenyl pyrophosphate (IPP). First, IPP may be synthesized through the well-known acetate/mevalonate pathway. However, recent studies have demonstrated that the mevalonate-dependent pathway does not operate in all living organisms. An alternate mevalonate-independent pathway for IPP biosynthesis has been characterized in bacteria and in green algae and higher plants (Horbach et al., *FEMS Microbiol. Lett.* 111:135–140 (1993); Rohmer et al., *Biochem.* 295:517–524 (1993); Schwender et al., *Biochem.* 316:73–80 (1996); Eisenreich et al., *Proc. Natl. Acad. Sci. USA* 93:6431–6436 (1996)).

Many steps in the mevalonate-independent isoprenoid pathway are known (FIG. 1). For example, the initial steps of the alternate pathway leading to the production of IPP have been studied in *Mycobacterium tuberculosis* by Cole et al. (*Nature* 393:537–544 (1998)). The first step of the pathway involves the condensation of two 3-carbon molecules (pyruvate and D-glyceraldehyde 3-phosphate) to yield a 5-carbon compound known as D-1-deoxyxylulose-5-phosphate. This reaction occurs by the Dxs enzyme, encoded by the dxs gene. Next, the isomerization and reduction of D-1-deoxyxylulose-5-phosphate yields 2-C-methyl-D-erythritol-4-phosphate. One of the enzymes involved in the isomerization and reduction process is D-1-deoxyxylulose-5-phosphate reductoisomerase (Dxr), encoded by the gene dxr. 2-C-methyl-D-erythritol-4-phosphate is subsequently converted into 4-diphosphocytidyl-2C-methyl-D-erythritol in a CTP-dependent reaction by the enzyme encoded by the non-annotated gene ygbP (Cole et al., supra). Recently, however, the ygbP gene was renamed as ispD as a part of the isp gene cluster (SwissProtein Accession #Q46893).

Next, the $2^{nd}$ position hydroxy group of 4-diphosphocytidyl-2C-methyl-D-erythritol can be phosphorylated in an ATP-dependent reaction by the enzyme encoded by the ychB gene. This product phosphorylates 4-diphosphocytidyl-2C-methyl-D-erythritol, resulting in 4-diphosphocytidyl-2C-methyl-D-erythritol 2-phosphate. The ychB gene was renamed as ispE, also as a part of the isp gene cluster (SwissProtein Accession #P24209). Finally, the product of the ygbB gene converts 4-diphosphocytidyl-2C-methyl-D-erythritol 2-phosphate to 2C-methyl-D-erythritol 2,4-cyclodiphosphate in a CTP-dependent manner. This gene has also been recently renamed, and belongs to the isp gene cluster. Specifically, the new name for the ygbB gene is ispF (SwissProtein Accession #P36663). The product of the pyrG gene is important in these reactions, as a CTP synthase.

The enzymes encoded by the lytB and gcpE genes (and perhaps others) are thought to participate in the reactions leading to formation of isopentenyl pyrophosphate (IPP) and dimethylallyl pyrophosphate (DMAPP). IPP may be isomerized to DMAPP via isopentenyl diphosphate isomerase (or "IPP isomerase"), encoded by the idi gene; however, this enzyme is not essential for survival and may be absent in some bacteria using the 2-C-methyl-D-erythritol 4-phosphate (MEP) pathway. Recent evidence suggests that the MEP pathway branches before IPP and separately produces IPP and DMAPP via the lytB gene product. A lytB knockout mutation is lethal in *E. coli* except in media supplemented with both IPP and DMAPP.

The synthesis of FPP occurs via the isomerization of IPP to dimethylallyl pyrophosphate (DMAPP). This reaction is followed by a sequence of two prenyltransferase reactions catalyzed by ispA, leading to the creation of geranyl pyrophosphate (GPP; a 10-carbon molecule) and farnesyl pyrophosphate (FPP; a 15-carbon molecule), respectively.

The Lower Carotenoid Biosynthetic Pathway

The division between the upper isoprenoid pathway and the lower carotenoid pathway is somewhat subjective. Because FPP synthesis is common in both carotenogenic and non-carotenogenic bacteria, the Applicants consider the first step in the lower carotenoid biosynthetic pathway to begin with the conversion of farnesyl pyrophosphate (FPP) to compounds of two divergent pathways, leading to the formation of either $C_{30}$ diapocarotenoids or $C_{40}$ carotenoids.

Within the $C_{40}$ pathway, the first step in the biosynthetic pathway begins with the prenyltransferase reaction converting farnesyl pyrophosphate (FPP) to a 20-carbon molecule known as geranylgeranyl pyrophosphate (GGPP) by the addition of IPP. The gene crtE (EC 2.5.1.29), encoding GGPP synthetase, is responsible for this prenyltransferase reaction. Then, a condensation reaction of two molecules of GGPP occurs to form phytoene ((7,8,11,12,7',8',11',12'-ω-octahydro-ω, ω-carotene; or PPPP), the first 40-carbon molecule of the lower carotenoid biosynthesis pathway. This enzymatic reaction is catalyzed by CrtB (phytoene synthase; EC 2.5.1.-).

Figure 2:
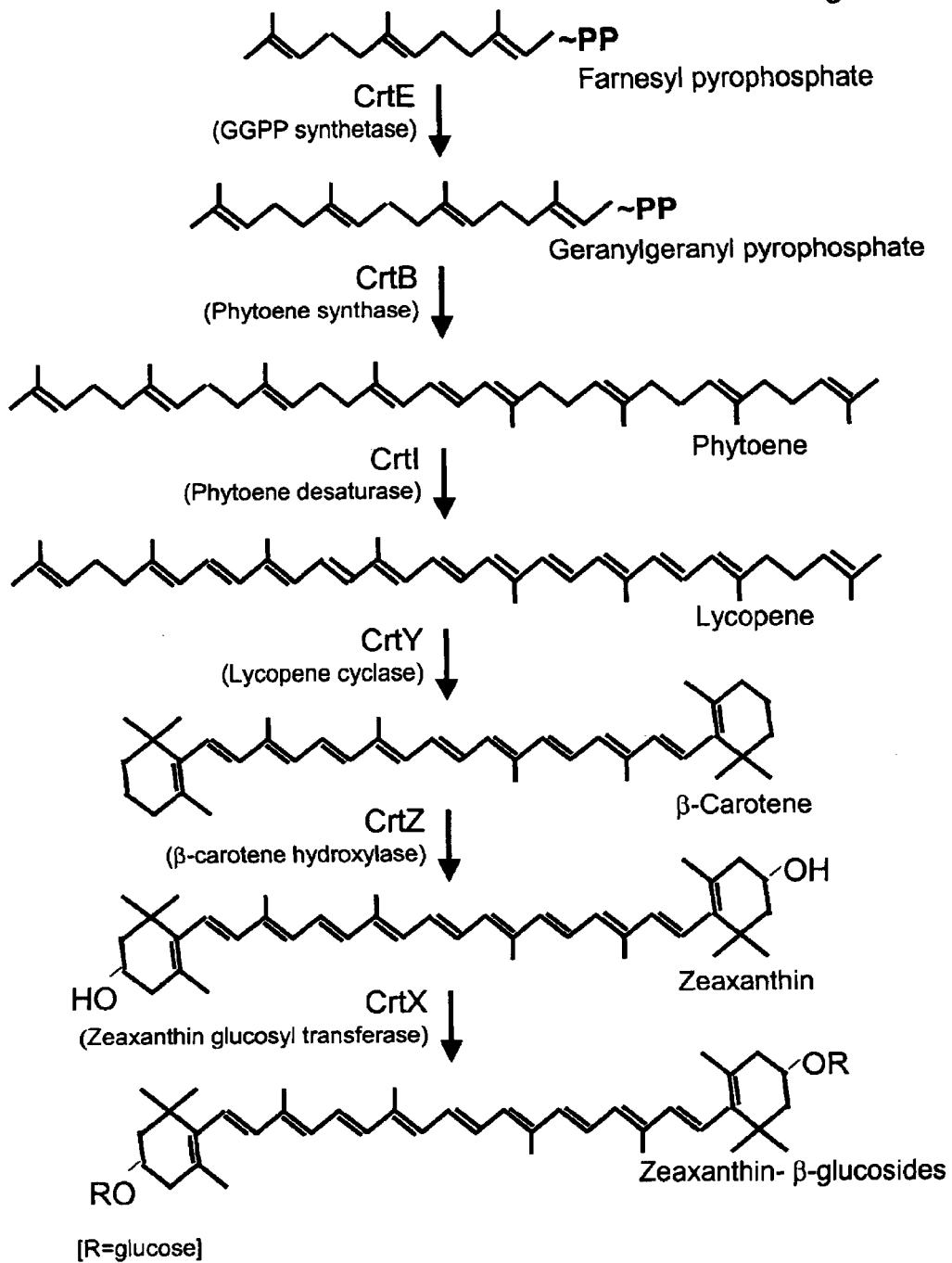
FIG. 2 shows a portion of the lower $C_{40}$ carotenoid biosynthetic pathway, to illustrate the specific chemical conversions catalyzed by CrtE, CrtX, CrtY, CrtI, CrtB, and CrtZ.

From the compound phytoene, a spectrum of $C_{40}$ carotenoids are produced by subsequent hydrogenation, dehydrogenation, cyclization, oxidation, or any combination of these processes. For example, lycopene, which imparts a "red"-colored spectra, is produced from phytoene through four sequential dehydrogenation reactions by the removal of eight atoms of hydrogen, catalyzed by the gene crtI (encoding phytoene desaturase) (see FIG. 2). Lycopene cyclase (CrtY) converts lycopene to β-carotene (β,β-carotene). β-carotene is converted to zeaxanthin ((3R,3'R)-β,β-carotene-3,3'-diol) via a hydroxylation reaction resulting from the activity of β-carotene hydroxylase (encoded by the crtZ gene).

In addition to crtE, crtY, crtI, crtB, and crtZ, which can be utilized in combination to create phytoene, lycopene, β-carotene, and zeaxanthin, various other crt genes are known which enable the intramolecular conversion of linear $C_{40}$ compounds to produce numerous other functionalized carotenoid compounds. One skilled in the art will be able to identify various other crt genes, according to publicly available literature (e.g., GenBank®), the patent literature, and experimental analysis of microorganisms having the ability to produce carotenoids. For example:

Zeaxanthin can be converted to zeaxanthin-β-glucosides by zeaxanthin glucosyl transferases encoded by the crtX gene (EC 2.4.1.-; e.g., GenBank® Accession #s D90087, M87280, M90698).

β-carotene can be converted to canthaxanthin by β-carotene ketolases encoded by crtW (e.g., GenBank® Accession #s AF218415, D45881, D58420, D58422, X86782, Y15112), crtO (e.g., GenBank® Accession #s X86782, Y15112) or bkt. Echinenone in an intermediate in this reaction.

Canthaxanthin can be converted to astaxanthin by β-carotene hydroxylase encoded by the crtZ gene. Adonirubrin is an intermediate in this reaction.

Zeaxanthin can be converted to astaxanthin by β-carotene ketolases encoded by crtW, crtO, or bkt. Adonixanthin is an intermediate in this reaction.

Spheroidene can be converted to spheroidenone by spheroidene monooxygenase encoded by crtA (e.g., GenBank® Accession #s AJ010302, Z11165, X52291).

Neurosporene can be converted to spheroidene and lycopene can be converted to spirilloxanthin by the sequential actions of hydroxyneurosporene synthase, methoxyneurosporene desaturase and hydroxyneurosporene-O-methyltransferase encoded by the crtC (e.g., GenBank® Accession #s AB034704, AF195122, AJ010302, AF287480, U73944, X52291, Z11165, Z21955), crtD (e.g., GenBank® Accession #s AJ010302, X63204, U73944, X52291, Z11165) and crtF (e.g., GenBank® Accession #s AB034704, AF288602, AJ010302, X52291, Z11165) genes, respectively.

β-carotene can be converted to isorenieratene by β-carotene desaturase encoded by crtU (e.g., GenBank® Accession #s AF047490, AF121947, AF139916, AF195507, AF272737, AF372617, AJ133724, AJ224683, D26095, U38550, X89897, Y15115).

These examples are not limiting and many other carotenoid genes and products exist within this $C_{40}$ lower carotenoid biosynthetic pathway. Thus, by using various combinations of the crtE, crtY, crtI, crtB, and crtZ genes presented herein, optionally in addition with any other known crt gene(s) isolated from plant, animal, and/or bacterial sources, innumerable different carotenoids and carotenoid derivatives could be made using the methods of the present invention, provided sufficient sources of FPP are available in the host organism.

It is envisioned that useful products of the present invention will include any carotenoid compound as defined herein including, but not limited to: antheraxanthin, adonirubin, adonixanthin, astaxanthin, canthaxanthin, capsorubrin, β-cryptoxanthin, α-carotene, β-carotene, epsilon-carotene, echinenone, 3-hydroxyechinenone, 3'-hydroxyechinenone, γ-carotene, 4-keto-γ-carotene, ζ-carotene, α-cryptoxanthin, deoxyflexixanthin, diatoxanthin, 7,8-didehydroastaxanthin, fucoxanthin, fucoxanthinol, isorenieratene, lactucaxanthin, lutein, lycopene, myxobactone, neoxanthin, neurosporene, hydroxyneurosporene, peridinin, phytoene, rhodopin, rhodopin glucoside, 4-keto-rubixanthin, siphonaxanthin, spheroidene, spheroidenone, spirilloxanthin, 4-keto-torulene, 3-hydroxy-4-keto-torulene, uriolide, uriolide acetate, violaxanthin, zeaxanthin-β-diglucoside, and zeaxanthin. Additionally, the invention encompasses derivitization of these molecules to create hydroxy-, methoxy-, oxo-, epoxy-, carboxy-, or aldehydic functional groups, glycoside esters, or sulfates.

Interaction between the Upper Isoprenoid Pathway and the Lower Carotenoid Biosynthetic Pathway A variety of studies have attempted to enhance carotenoid production by enhancing overall isoprenoid biosynthesis. The up-regulation of idi, in particular, has been demonstrated to dramatically affect carotenoid production. For example, Kajiwara et al. (*Biochem. J.* 324:421–426 (1997)) first demonstrated that "IPP isomerase forms an influential step in isoprenoid biosynthesis of the prokaryote *E. coli*, with potential for the efficient production of industrially useful isoprenoids by metabolic engineering". Specifically, exogenously expressed IPP isomerases permitted 3.6–4.5 fold greater levels of lycopene production in *E. coli* comprising an *Erwinia* carotenoid biosynthesis gene cluster, as compared to the control; likewise, 1.5–2.7 fold greater levels of β-carotene and 1.7–2.1 fold greater levels of phytoene were produced.

Subsequent work by Wang et al. (*Biotech. Bioengineering* 62(2):235–241 (1999)) resulted in 50 times greater astaxanthin production in an *E. coli* transformed with the *E. coli* idi gene, *Archaeoglobus fulgidus* gps gene, and *Agrobacterium aurantiacum* crtBIYZW gene cluster. It was concluded that the last step in GGPP synthesis is the first rate-controlling step in carotenoid production, while the second rate-controlling step was IPP isomerization. And finally, Albrecht et al. (*Biotech. Letters* 21:791–795 (1999)) discovered that over-expression of the endogenous dxs and dxr genes and an exogenous idi gene (from *Phaffia rhodozyma*) in *E. coli* could stimulate carotenogenesis up to 3.5 fold.

Thus, metabolic engineering methods directed toward maximizing the production of industrially valuable carotenoids in *E. coli* and other bacteria should carefully consider the flux and rate-limiting steps in the upper isoprenoid pathway, as well as expression levels within the lower carotenoid biosynthetic pathway. Over-expression of rate-limiting genes of the upper isoprenoid pathway (e.g., idi) can dramatically increase carotenogenesis.

Sequence Identification of *P. agglomerans* strain DC404 Carotenoid Biosynthetic Genes and Enzymes A variety of nucleotide sequences have been isolated from strain DC404 encoding gene products involved in the $C_{40}$ carotenoid biosynthetic pathway. ORF's 1 and 3–6, for example, encode the crtE, Y, I, B and Z genes in the lower carotenoid biosynthetic pathway (see FIGS. 1 and 2) and their enzymatic products lead to the production of the pigmented carotenoids lycopene, β-carotene, and zeaxanthin. ORF 2 encodes the idi gene in the upper isoprenoid pathway. These 6 ORFs are comprised on a single nucleic acid fragment (SEQ ID NO:18), having the following genetic organization: crtE-idi-crtY-crtI-crtB-crtZ. The crtE-idi-crtY-crtI-crtB genes appear operably linked in an operon, whereas the crtZ gene is transcribed in the opposite orientation.

The entire set of genes (crtE-idi-crtY-crtI-crtB-crtZ) isolated from strain DC404 are disclosed herein in a single sequence (SEQ ID NO:18). This gene cluster has been placed on a vector and expressed in microbial hosts for the production of carotenoid compounds. The skilled person will recognize that minor nucleic acid substitutions, additions and deletions (such as the substitutions of preferred codons for specific host cell expression) may be made to such a gene cluster without affecting its utility provided that all of the encoded polypeptides are expressed and are enzymatically active. Accordingly it is within the scope of the invention to provide an isolated nucleic acid molecule as set forth in SEQ ID NO:18, comprising the crtE-idi-crtY-crtI-crtB-crtZ, genes or an isolated nucleic acid molecule having at least 95% identity to SEQ ID NO:18, wherein the isolated nucleic acid molecule encodes all of the polypeptides crtE, idi, crtY, crtI, crtB, and crtZ.

Comparison of the crtE nucleotide base and deduced amino acid sequences (ORF 1) to public databases reveals that the most similar known sequences are about 65% identical to the amino acid sequence of CrtE reported herein over a length of 301 amino acids using a Smith-Waterman alignment algorithm (W. R. Pearson, *Comput. Methods Genome Res.*, [Proc. Int. Symp.] (1994), Meeting Date 1992, 111–20. Suhai, Sandor, Ed. Plenum: New York, N.Y.). More preferred amino acid fragments are at least about 70%–80% identical to the sequences herein, where those sequences that are 85%–90% identical are particularly suitable and those sequences that are about 95% identical are most preferred. Similarly, preferred crtE encoding nucleic acid sequences corresponding to the instant ORF's are those encoding active proteins and which are at least about 70%–80% identical to the nucleic acid sequences of crtE reported herein, where those sequences that are 85%–90% identical are particularly suitable and those sequences that are about 95% identical are most preferred.

Comparison of the idi nucleotide base and deduced amino acid sequences (ORF 2) to public databases reveals that the most similar known sequences are about 67% identical to the amino acid sequence of Idi reported herein over a length of 349 amino acids using a Smith-Waterman alignment algorithm (W. R. Pearson, supra). More preferred amino acid fragments are at least about 70%–80% identical to the sequences herein, where those sequences that are 85%–90% identical are particularly suitable and those sequences that are about 95% identical are most preferred. Similarly, preferred idi encoding nucleic acid sequences corresponding to the instant ORF's are those encoding active proteins and which are at least about 70%–80% identical to the nucleic acid sequences of idi reported herein, where those sequences that are 85%–90% identical are particularly suitable and those sequences that are about 95% identical are most preferred.

Comparison of the crtY nucleotide base and deduced amino acid sequences (ORF 3) to public databases reveals that the most similar known sequences are about 61% identical to the amino acid sequence of CrtY reported herein over a length of 389 amino acids using a Smith-Waterman alignment algorithm (W. R. Pearson, supra). More preferred amino acid fragments are at least about 70%–80% identical to the sequences herein, where those sequences that are 85%–90% identical are particularly suitable and those sequences that are about 95% identical are most preferred. Similarly, preferred crtY encoding nucleic acid sequences corresponding to the instant ORF's are those encoding active proteins and which are at least about 70%–80% identical to the nucleic acid sequences of crtY reported herein, where those sequences that are 85%–90% identical are particularly suitable and those sequences that are about 95% identical are most preferred.

Comparison of the crtI nucleotide base and deduced amino acid sequences (ORF 4) to public databases reveals that the most similar known sequences are about 82% identical to the amino acid sequence of CrtI reported herein over a length of 492 amino acids using a Smith-Waterman alignment algorithm (W. R. Pearson, supra). Preferred amino acid fragments are at least about 70%–80% identical to the sequences herein, where those sequences that are 85%–90% identical are particularly suitable and those sequences that are about 95% identical are most preferred. Similarly, preferred crtI encoding nucleic acid sequences corresponding to the instant ORF's are those encoding active proteins and which are at least about 70%–80% identical to the nucleic acid sequences of crtI reported herein, where those sequences that are 85%–90% identical are particularly suitable and those sequences that are about 95% identical are most preferred.

Comparison of the crtB nucleotide base and deduced amino acid sequences (ORF 5) to public databases reveals that the most similar known sequences are about 67% identical to the amino acid sequence of CrtB reported herein over a length of 308 amino acids using a Smith-Waterman alignment algorithm (W. R. Pearson, supra). More preferred amino acid fragments are at least about 70%–80% identical to the sequences herein, where those sequences that are 85%–90% identical are particularly suitable and those sequences that are about 95% identical are most preferred. Similarly, preferred crtB encoding nucleic acid sequences corresponding to the instant ORF's are those encoding active proteins and which are at least about 70%–80% identical to the nucleic acid sequences of crtB reported herein, where those sequences that are 85%–90% identical are particularly suitable and those sequences that are about 95% identical are most preferred.

Comparison of the crtZ nucleotide base and deduced amino acid sequences (ORF 6) to public databases reveals that the most similar known sequences are about 73% identical to the amino acid sequence of CrtZ reported herein over a length of 185 amino acids using a Smith-Waterman alignment algorithm (W. R. Pearson, supra). Preferred amino acid fragments are at least about 70%–80% identical to the sequences herein, where those sequences that are 85%–90% identical are particularly suitable and those sequences that are about 95% identical are most preferred. Similarly, preferred crtZ encoding nucleic acid sequences corresponding to the instant ORF's are those encoding active proteins and which are at least about 70%–80% identical to the nucleic acid sequences of crtZ reported herein, where those sequences that are 85%–90% identical are particularly suitable and those sequences that are about 95% identical are most preferred.

Isolation of Homologs

Each of the nucleic acid fragments of the $C_{40}$ carotenoid biosynthetic pathway of the instant invention may be used to isolate genes encoding homologous proteins from the same or other microbial (or plant) species. Isolation of homologous genes using sequence-dependent protocols is well known in the art. Examples of sequence-dependent protocols include, but are not limited to: 1.) methods of nucleic acid hybridization; 2.) methods of DNA and RNA amplification, as exemplified by various uses of nucleic acid amplification technologies [e.g., polymerase chain reaction (PCR), Mullis et al., U.S. Pat. No. 4,683,202; ligase chain reaction (LCR), Tabor, S. et al., *Proc. Natl. Acad. Sci. USA* 82:1074 (1985); or strand displacement amplification (SDA), Walker, et al., *Proc. Natl. Acad. Sci. USA,* 89:392 (1992)]; and 3.) methods of library construction and screening by complementation.

For example, genes encoding similar proteins or polypeptides to those of the $C_{40}$ carotenoid biosynthetic pathway, as described herein, could be isolated directly by using all or a portion of the instant nucleic acid fragments as DNA hybridization probes to screen libraries from any desired bacteria using methodology well known to those skilled in the art (wherein those bacteria producing $C_{40}$ carotenoids would be preferred). Specific oligonucleotide probes based upon the instant nucleic acid sequences can be designed and synthesized by methods known in the art (Maniatis, supra). Moreover, the entire sequences can be used directly to synthesize DNA probes by methods known to the skilled artisan (e.g., random primers DNA labeling, nick translation, or end-labeling techniques), or RNA probes using available in vitro transcription systems. In addition, specific primers can be designed and used to amplify a part of (or full-length of) the instant sequences. The resulting amplification products can be labeled directly during amplification reactions or labeled after amplification reactions, and used as probes to isolate full-length DNA fragments under conditions of appropriate stringency.

Typically, in PCR-type amplification techniques, the primers have different sequences and are not complementary to each other. Depending on the desired test conditions, the sequences of the primers should be designed to provide for both efficient and faithful replication of the target nucleic acid. Methods of PCR primer design are common and well known in the art (Thein and Wallace, "The use of oligonucleotide as specific hybridization probes in the Diagnosis of Genetic Disorders", in *Human Genetic Diseases: A Practical Approach*, K. E. Davis Ed., (1986) pp 33–50, IRL: Herndon, Va.; and Rychlik, W., In *Methods in Molecular Biology*, White, B. A. Ed., (1993) Vol. 15, pp 31–39, PCR Protocols: Current Methods and Applications. Humania: Totowa, N.J.).

Generally two short segments of the instant sequences may be used in polymerase chain reaction protocols to amplify longer nucleic acid fragments encoding homologous genes from DNA or RNA. The polymerase chain reaction may also be performed on a library of cloned nucleic acid fragments wherein the sequence of one primer is derived from the instant nucleic acid fragments, and the sequence of the other primer takes advantage of the presence of the polyadenylic acid tracts to the 3' end of the mRNA precursor encoding microbial genes.

Alternatively, the second primer sequence may be based upon sequences derived from the cloning vector. For example, the skilled artisan can follow the RACE protocol (Frohman et al., *Proc. Natl. Acad. Sci. USA* 85:8998 (1988)) to generate cDNAs by using PCR to amplify copies of the region between a single point in the transcript and the 3' or 5' end. Primers oriented in the 3' and 5' directions can be designed from the instant sequences. Using commercially available 3' RACE or 5' RACE systems (BRL, Gaithersburg, Md.), specific 3' or 5' cDNA fragments can be isolated (Ohara et al., *Proc. Natl. Acad. Sci. USA* 86:5673 (1989); Loh et al., *Science* 243:217 (1989)).

Alternatively, the instant sequences of the $C_{40}$ carotenoid biosynthetic pathway may be employed as hybridization reagents for the identification of homologs. The basic components of a nucleic acid hybridization test include a probe, a sample suspected of containing the gene or gene fragment of interest, and a specific hybridization method. Probes of the present invention are typically single-stranded nucleic acid sequences that are complementary to the nucleic acid sequences to be detected. Probes are "hybridizable" to the nucleic acid sequence to be detected. The probe length can vary from 5 bases to tens of thousands of bases, and will depend upon the specific test to be done. Typically a probe length of about 15 bases to about 30 bases is suitable. Only part of the probe molecule need be complementary to the nucleic acid sequence to be detected. In addition, the complementarity between the probe and the target sequence need not be perfect. Hybridization does occur between imperfectly complementary molecules with the result that a certain fraction of the bases in the hybridized region are not paired with the proper complementary base.

Hybridization methods are well defined. Typically the probe and sample must be mixed under conditions which will permit nucleic acid hybridization. This involves contacting the probe and sample in the presence of an inorganic or organic salt under the proper concentration and temperature conditions. The probe and sample nucleic acids must be in contact for a long enough time that any possible hybridization between the probe and sample nucleic acid may occur. The concentration of probe or target in the mixture will determine the time necessary for hybridization to occur. The higher the probe or target concentration, the shorter the hybridization incubation time needed. Optionally, a chaotropic agent may be added. The chaotropic agent stabilizes nucleic acids by inhibiting nuclease activity. Furthermore, the chaotropic agent allows sensitive and stringent hybridization of short oligonucleotide probes at room temperature (Van Ness and Chen, *Nucl. Acids Res.* 19:5143–5151 (1991)). Suitable chaotropic agents include guanidinium chloride, guanidinium thiocyanate, sodium thiocyanate, lithium tetrachloroacetate, sodium perchlorate, rubidium tetrachloroacetate, potassium iodide, and cesium trifluoroacetate, among others. Typically, the chaotropic agent will be present at a final concentration of about 3 M. If desired, one can add formamide to the hybridization mixture, typically 30–50% (v/v).

Various hybridization solutions can be employed. Typically, these comprise from about 20 to 60% volume, preferably 30%, of a polar organic solvent. A common hybridization solution employs about 30–50% v/v formamide, about 0.15 to 1 M sodium chloride, about 0.05 to 0.1 M buffers (e.g., sodium citrate, Tris-HCl, PIPES or HEPES (pH range about 6–9)), about 0.05 to 0.2% detergent (e.g., sodium dodecylsulfate), or between 0.5–20 mM EDTA, FICOLL (Pharmacia Inc.) (about 300–500 kdal), polyvinylpyrrolidone (about 250–500 kdal), and serum albumin. Also included in the typical hybridization solution will be unlabeled carrier nucleic acids from about 0.1 to 5 mg/mL, fragmented nucleic DNA (e.g., calf thymus or salmon sperm DNA, or yeast RNA), and optionally from about 0.5 to 2% wt/vol glycine. Other additives may also be included, such as volume exclusion agents that include a variety of polar water-soluble or swellable agents (e.g., polyethylene glycol), anionic polymers (e.g., polyacrylate or polymethylacrylate), and anionic saccharidic polymers (e.g., dextran sulfate).

Nucleic acid hybridization is adaptable to a variety of assay formats. One of the most suitable is the sandwich assay format. The sandwich assay is particularly adaptable to hybridization under non-denaturing conditions. A primary component of a sandwich-type assay is a solid support. The solid support has adsorbed to it or covalently coupled to it immobilized nucleic acid probe that is unlabeled and complementary to one portion of the sequence.

Availability of the instant nucleotide and deduced amino acid sequences facilitates immunological screening of DNA expression libraries. Synthetic peptides representing portions of the instant amino acid sequences may be synthesized. These peptides can be used to immunize animals to produce polyclonal or monoclonal antibodies with specificity for peptides or proteins comprising the amino acid sequences. These antibodies can be then be used to screen DNA expression libraries to isolate full-length DNA clones of interest (Lerner, R. A., *Adv. Immunol.* 36:1 (1984); Maniatis, supra).

Genetic Organization

Although a variety of gene sequences are available encoding idi and crtE, crtX, crtY, crtI, crtB, and crtZ from various species within the genera *Pantoea*, the instant nucleic acid fragment disclosed as SEQ ID NO:18 (8814 bp) appears to have a unique genetic organization of crtE-idi-crtY-crtI-crtB-crtZ, wherein:

crtE (SEQ ID NO:1) is located at nucleotides 2400–3305 and translated in a direct orientation;

idi (SEQ ID NO:3) is located at nucleotides 3343–4392 and translated in a direct orientation;

crtY (SEQ ID NO:5) is located at nucleotides 4424–5593 and translated in a direct orientation;

crtI (SEQ ID NO:7) is located at nucleotides 5590–7068 and translated in a direct orientation;

crtB (SEQ ID NO:9) is located at nucleotides 7068–7994 and translated in a direct orientation; and crtZ (SEQ ID NO:11) is located at nucleotides 7909–8466 and translated in an orientation opposite to crtE-idi-crtY-crtI-crtB.

The most "common" genetic organization is that observed in *P. ananatis* (GenBank® Accession No. D90087), *P. stewartii* (GenBank® Accession No. AY166713), and *Pantoea agglomerans* pv. *milletiae* (GenBank® Accession No. AB076662), wherein the carotenogenic cluster comprises crtEXYIBZ (also notated as "crtE-crtX-crtY-crtI-crtB-crtZ") (FIG. 5). *P. agglomerans* EHO-10 (GenBank® Accession No. M87280) is annotated as comprising a carotenogenic cluster of crtE-hypothetical protein-crtX-crtY-crtI-crtB-crtZ; however, bioinformatic analysis of the "hypothetical protein" by the Applicants' herein determined that the true *P. agglomerans* EHO-10 should be considered as comprising crtE-idi-crtX-crtY-crtI-crtB-crtZ.

Likewise, other carotenogenic gene clusters from more distantly related organisms do not contain the unique genetic organization of crtE-idi-crtY-crtI-crtB-crtZ. For example, the canthaxanthin gene cluster of *Bradyrhizobium* ORS278 is crtE-crtY-crtI-crtB-crtW, the astaxanthin gene cluster of *Agrobacterium aurantiacum* is crtW-crtZ-crtY-crtI-crtB; and, the zeaxanthin gene cluster of *Flavobacterium* sp. R1534 is crtZ-crtY-crtI-crtB-crtE (Giraud et al., US2003/0087337 A1).

The genetic organization disclosed herein may convey several unique advantages during metabolic engineering useful for maximizing the production of industrially valuable carotenoids in *E. coli* and other bacteria. First, since idi encoding isopentenyl pyrophosphate isomerase has been demonstrated to dramatically affect carotenoid production (Kajiwara et al., supra; Wang et al., supra; Albrecht et al., supra), and since this gene is directly incorporated into the carotenogenic crtE-idi-crtY-crtI-crtB-crtZ cluster described herein, it is possible that expression of the operon will lead to increased isoprenoid flux into the lower carotenoid biosynthetic pathway, thereby leading to increased carotenoid production and titer. Secondly, advantages may be incurred by the absence of the crtX gene in the present carotenogenic crtE-idi-crtY-crtI-crtB-crtZ cluster. Specifically, the conversion of zeaxanthin to zeaxanthin-$\beta$-glucosides by CrtX is excluded, thus permitting high level accumulation of zeaxanthin as a product of the reaction encoded by the carotenogenic cluster described herein. The absence of crtX in the expression cluster may also be beneficial for synthesis of $\beta$-carotene, since no extra effort will be required to remove the non-needed crtX gene from the cluster.

Accordingly, the present invention provides a method for the production of carotenoid compounds comprising:

(a) providing a transformed host cell comprising:
 (i) suitable levels of farnesyl pyrophosphate; and
 (ii) a nucleic acid molecule encoding carotenoid biosynthetic pathway enzymes under the control of suitable regulatory sequences, wherein the genetic organization of the molecule is crtE-idi-crtY-crtI-crtB-crtZ, wherein the crtE, idi, crtY, crtI, crtB, and crtZ genes are clustered in the order stated and wherein the transcription of the crtZ occurs in opposite orientation to that of crtE, idi, crtY, crtI, and crtB; and (b) growing the transformed host cells of (a) under suitable growth conditions with an effective amount of a fermentable carbon substrate.

Recombinant Expression in Microorganisms

The genes and gene products of the instant sequences may be produced in heterologous host cells, particularly in the cells of microbial hosts. Expression in recombinant microbial hosts may be useful for the expression of various pathway intermediates, and/or for the modulation of pathways already existing in the host for the synthesis of new products heretofore not possible using the host.

Methods for introduction of genes encoding the appropriate upper isoprene pathway genes and various combinations of the lower carotenoid biosynthetic pathway genes of the instant invention (optionally with other crt genes) into a suitable microbial host are common. As will be obvious to one skilled in the art, the particular functionalities required to be introduced into a host organism for production of a particular carotenoid product will depend on the host cell (and its native production of isoprenoid compounds), the availability of substrate, and the desired end product(s).

It will be appreciated that for the present crt genes to be effective in the production of carotenoids, it will be necessary for the host cell to have suitable levels of FPP within the cell. FPP may be supplied exogenously, or may be produced endogenously by the cell, either through native or introduced genetic pathways. It is contemplated, therefore, that where a specific host cell does not have the genetic machinery to produce suitable levels of FPP, it is well within the grasp of the skilled person in the art to obtain any necessary genes of the upper isoprenoid pathway and engineer these genes into the host to produce FPP as the starting material for carotenoid biosynthesis through the lower pathway. As a precursor of FPP, IPP may be synthesized through the well-known acetate/mevalonate pathway. Alternatively, recent studies have demonstrated that the mevalonate-dependent pathway does not operate in all living organisms;

an alternate mevalonate-independent pathway for IPP biosynthesis has been characterized in bacteria and in green algae and higher plants (Horbach et al., *FEMS Microbiol. Lett.* 111:135–140 (1993); Rohmer et al, *Biochem.* 295: 517–524 (1993); Schwender et al., *Biochem.* 316: 73–80 (1996); Eisenreich et al., *Proc. Natl. Acad. Sci. USA* 93: 6431–6436 (1996)).

It is expected, for example, that introduction of chimeric genes encoding one or more of the instant lower $C_{40}$ carotenoid biosynthetic pathway crtEYIBZ sequences will lead to production of carotenoid compounds in the host microbe of choice. With an appropriate genetic transformation system, it should be possible to genetically engineer a variety of non-carotenogenic hosts. This has been shown, for example, using *Erwinia herbicola* crt genes, to produce various carotenoids in the hosts *E. coli, Agrobacterium tumefaciens, Saccharomyces cerevisiae, Pichia pastoris* (yeast), *Aspergillus nidulans* (fungi), *Rhodobacter sphaeroides*, and higher plants (U.S. Pat. No. 5,656,472). Thus, as described previously herein, antheraxanthin, adonirubin, adonixanthin, astaxanthin, canthaxanthin, capsorubrin, β-cryptoxanthin, α-carotene, β-carotene, epsilon-carotene, echinenone, 3-hydroxyechinenone, 3'-hydroxyechinenone, γ-carotene, 4-keto-γ-carotene, ζ-carotene, α-cryptoxanthin, deoxyflexixanthin, diatoxanthin, 7,8-didehydroastaxanthin, fucoxanthin, fucoxanthinol, isorenieratene, lactucaxanthin, lutein, lycopene, myxobactone, neoxanthin, neurosporene, hydroxyneurosporene, peridinin, phytoene, rhodopin, rhodopin glucoside, 4-keto-rubixanthin, siphonaxanthin, spheroidene, spheroidenone, spirilloxanthin, 4-keto-torulene, 3-hydroxy-4-keto-torulene, uriolide, uriolide acetate, violaxanthin, zeaxanthin-β-diglucoside, and zeaxanthin may all be produced in microbial hosts using the teachings herein, by introducing various combinations of the following crt enzyme functionalities (for example): CrtE, CrtX, CrtY, CrtI, CrtB, CrtZ, CrtW, CrtO, CrtA, CrtC, CrtD, CrtF, and CrtU. Thus, formation of phytoene from FPP requires CrtE and CrtB; the carotenoid-specific genes necessary for the synthesis of lycopene from FPP include crtE, crtB and crtI; and genes required for β-carotene production from FPP include crtE, crtB, crtI, and crtY. Given this understanding of the relationship between the crt genes, it will be possible to select appropriate microbial host cells and crt genes for expression of any desired carotenoid product. In a similar manner, expression may be amplified by up-regulation of upper isoprene pathway genes, e.g., idi.

Microbial expression systems and expression vectors containing regulatory sequences that direct high level expression of foreign proteins are well known to those skilled in the art. Any of these could be used to construct chimeric genes for production of any of the gene products of the instant sequences. These chimeric genes could then be introduced into appropriate microorganisms via transformation to provide high level expression of the enzymes.

Vectors or cassettes useful for the transformation of suitable host cells are well known in the art. Typically the vector or cassette contains sequences directing transcription and translation of the relevant gene(s), a selectable marker, and sequences allowing autonomous replication or chromosomal integration. Suitable vectors comprise a region 5' of the gene which harbors transcriptional initiation controls and a region 3' of the DNA fragment which controls transcriptional termination. It is most preferred when both control regions are derived from genes homologous to the transformed host cell, although it is to be understood that such control regions need not be derived from the genes native to the specific species chosen as a production host.

Initiation control regions or promoters which are useful to drive expression of the instant ORFs in the desired host cell are numerous and familiar to those skilled in the art. Virtually any promoter capable of driving these genes is suitable for the present invention including, but not limited to: CYC1, HIS3, GAL1, GAL10, ADH1, PGK, PHO5, GAPDH, ADC1, TRP1, URA3, LEU2, ENO, TPI (e.g., useful for expression in *Saccharomyces*); AOX1 (e.g., useful for expression in *Pichia*); and lac, ara, tet, trp, $IP_L$, $IP_R$, T7, tac, and trc (e.g., useful for expression in *Escherichia coli*) as well as the amy, apr, npr promoters and various phage promoters useful for expression in, e.g., *Bacillus*. Additionally, the deoxy-xylulose phosphate synthase or methanol dehydrogenase operon promoter (Springer et al., *FEMS Microbiol Lett* 160:119–124 (1998)), the promoter for polyhydroxyalkanoic acid synthesis (Foellner et al., *Appl. Microbiol. Biotechnol.* 40:284–291 (1993)), promoters identified from native plasmids in methylotrophs (EP 296484), Plac (Toyama et al., *Microbiology* 143:595–602 (1997); EP 62971), Ptrc (Brosius et al., *Gene* 27:161–172 (1984)), promoters identified from methanotrophs (PCT/US03/33698), and promoters associated with antibiotic resistance [e.g., kanamycin (Springer et al., *FEMS Microbiol Lett* 160:119–124 (1998); Ueda et al., *Appl. Environ. Microbiol.* 57:924–926 (1991)) or tetracycline (U.S. Pat. No. 4,824,786)] are suitable for expression in C1 metabolizers.

It is necessary to include an artificial ribosomal binding site ("RBS") upstream of a gene to be expressed, when the RBS is not provided by the vector. This is frequently required for the second, third, etc. gene(s) of an operon to be expressed, when a single promoter is driving the expression of a first, second, third, etc. group of genes. Methodology to determine the preferred sequence of a RBS in a particular host organism will be familiar to one of skill in the art, as are means for creation of this synthetic site.

Termination control regions may also be derived from various genes native to the preferred hosts. Optionally, a termination site may be unnecessary; however, it is most preferred if included.

Merely inserting a gene into a cloning vector does not ensure that it will be successfully expressed at the level needed. In response to the need for a high expression rate, many specialized expression vectors have been created by manipulating a number of different genetic elements that control aspects of transcription, translation, protein stability, oxygen limitation, and secretion from the host cell. More specifically, the molecular features that have been manipulated to control gene expression include: 1.) the nature of the relevant transcriptional promoter and terminator sequences; 2.) the strength of the ribosome binding site; 3.) the number of copies of the cloned gene and whether the gene is plasmid-borne or integrated into the genome of the host cell; 4.) the final cellular location of the synthesized foreign protein; 5.) the efficiency of translation in the host organism; 6.) the intrinsic stability of the cloned gene protein within the host cell; and 7.) the codon usage within the cloned gene, such that its frequency approaches the frequency of preferred codon usage of the host cell. Each of these types of modifications are encompassed in the present invention, as means to further optimize expression of $C_{40}$ carotenoids.

Finally, to promote accumulation of $C_{40}$ carotenoids, it may be necessary to reduce or eliminate the expression of certain genes in the target pathway or in competing pathways that may serve as sinks for energy or carbon. Alternatively, it may be useful to over-express various genes upstream of desired carotenoid intermediates to enhance production. Methods of manipulating genetic pathways for the purposes described above are common and well known in the art.

For example, once a key genetic pathway has been identified and sequenced, specific genes may be up-regulated to increase the output of the pathway. For example, additional copies of the targeted genes may be introduced into the host cell on multicopy plasmids such as pBR322. Alternatively the target genes may be modified so as to be under the control of non-native promoters. Where it is desired that a pathway operate at a particular point in a cell cycle or during a fermentation run, regulated or inducible promoters may used to replace the native promoter of the target gene. Similarly, in some cases the native or endogenous promoter may be modified to increase gene expression. For example, endogenous promoters can be altered in vivo by mutation, deletion, and/or substitution (see, U.S. Pat. No. 5,565,350; Zarling et al., PCT/US93/03868).

Alternatively, where the sequence of the gene to be disrupted is known, one of the most effective methods for gene down-regulation is targeted gene disruption, where foreign DNA is inserted into a structural gene so as to disrupt transcription. This can be effected by the creation of genetic cassettes comprising the DNA to be inserted (often a genetic marker) flanked by sequences having a high degree of homology to a portion of the gene to be disrupted. Introduction of the cassette into the host cell results in insertion of the foreign DNA into the structural gene via the native DNA replication mechanisms of the cell. (See, for example: Hamilton et al., *J. Bacteriol.* 171:4617–4622 (1989); Balbas et al., *Gene* 136:211–213 (1993); Gueldener et al., *Nucleic Acids Res.* 24:2519–2524 (1996); and Smith et al., *Methods Mol. Cell. Biol.* 5:270–277(1996)).

Antisense technology is another method of down-regulating genes where the sequence of the target gene is known. To accomplish this, a nucleic acid segment from the desired gene is cloned and operably linked to a promoter such that the anti-sense strand of RNA will be transcribed. This construct is then introduced into the host cell and the antisense strand of RNA is produced. Antisense RNA inhibits gene expression by preventing the accumulation of mRNA encoding the protein of interest. The person skilled in the art will know that special considerations are associated with the use of antisense technologies in order to reduce expression of particular genes. For example, the proper level of expression of antisense genes may require the use of different chimeric genes utilizing different regulatory elements known to the skilled artisan.

Although targeted gene disruption and antisense technology offer effective means of down-regulating genes where the sequence is known, other less specific methodologies have been developed that are not sequence-based. For example, cells may be exposed to UV radiation and then screened for the desired phenotype. Mutagenesis with chemical agents is also effective for generating mutants and commonly used substances include chemicals that affect nonreplicating DNA (e.g., $HNO_2$ and $NH_2OH$), as well as agents that affect replicating DNA (e.g., acridine dyes, notable for causing frameshift mutations). Specific methods for creating mutants using radiation or chemical agents are well documented in the art. See, for example: Thomas D. Brock in *Biotechnology: A Textbook of Industrial Microbiology*, $2^{nd}$ ed., (1989) Sinauer Associates: Sunderland, Mass.; or Deshpande, Mukund V., *Appl. Biochem. Biotechnol.*, 36: 227–234 (1992).

Another non-specific method of gene disruption is the use of transposable elements or transposons. Transposons are genetic elements that insert randomly in DNA but can be later retrieved on the basis of sequence to determine where the insertion has occurred. Both in vivo and in vitro transposition methods are known. Both methods involve the use of a transposable element in combination with a transposase enzyme. When the transposable element or transposon is contacted with a nucleic acid fragment in the presence of the transposase, the transposable element will randomly insert into the nucleic acid fragment. The technique is useful for random mutagenesis and for gene isolation, since the disrupted gene may be identified on the basis of the sequence of the transposable element. Kits for in vitro transposition are commercially available (see, for example: The Primer Island Transposition Kit, available from Perkin Elmer Applied Biosystems, Branchburg, N.J., based upon the yeast Ty1 element; The Genome Priming System, available from New England Biolabs, Beverly, Mass., based upon the bacterial transposon Tn7; and the EZ::TN Transposon Insertion Systems, available from Epicentre Technologies, Madison, Wis., based upon the Tn5 bacterial transposable element).

Within the context of the present invention, it may be useful to modulate the expression of the carotenoid biosynthetic pathway by any one of the methods described above. For example, the present invention provides a number of isolated genes encoding enzymes in the carotenoid biosynthetic pathway and methods leading to the production of $C_{40}$ carotenoids. Thus, in addition to over-expressing various combinations of the crtE, idi, crtY, crtI, crtB, and crtZ genes herein to promote increased production of $C_{40}$ carotenoids, it may also be useful to up-regulate the initial condensation of 3-carbon compounds (pyruvate and D-glyceraldehyde 3-phosphate) to increase the yield of the 5-carbon compound D-1-deoxyxylulose-5-phosphate (mediated by the dxs gene). This would increase the flux of carbon entering the lower carotenoid biosynthetic pathway and permit increased production of $C_{40}$ carotenoids. Alternatively (or in addition to), it may be desirable to knockout the crtM/crtN genes leading to the synthesis of $C_{30}$ carotenoids, if the microbial host is capable of synthesizing these types of compounds. Or, in systems having native functional crtE, crtX, crtY, crtI, crtB, and crtZ genes, the accumulation of β-carotene or zeaxanthin may be effected by the disruption of downstream genes (e.g., crtZ or crtX) by any one of the methods described above.

Preferred Microbial Hosts

Preferred heterologous host cells for expression of the instant genes and nucleic acid fragments of the carotenoid biosynthetic pathway are microbial hosts that can be found broadly within the fungal or bacterial families and which grow over a wide range of temperature, pH values, and solvent tolerances. For example, it is contemplated that any bacteria, yeast, and filamentous fungi will be suitable hosts for expression of the present nucleic acid fragments. Because transcription, translation and the protein biosynthetic apparatus are the same irrespective of the cellular feedstock, functional genes are expressed irrespective of carbon feedstock used to generate cellular biomass. Large-scale microbial growth and functional gene expression may utilize a wide range of simple or complex carbohydrates, organic acids and alcohols, and/or saturated hydrocarbons (e.g., methane or carbon dioxide, in the case of photosynthetic or chemoautotrophic hosts). However, the functional genes may be regulated, repressed or depressed by specific growth conditions, which may include the form and amount of nitrogen, phosphorous, sulfur, oxygen, carbon or any trace micronutrient including small inorganic ions. In addition, the regulation of functional genes may be achieved by the presence or absence of specific regulatory molecules that are added to the culture and are not typically considered nutrient or energy sources. Growth rate may also be an important regulatory factor in gene expression.

Examples of suitable host strains include, but are not limited to: *Aspergillus, Trichoderma, Saccharomyces, Pichia, Candida, Hansenula, Yarrowia, Rhodosporidium, Lipomyces, Salmonella, Bacillus, Acinetobacter, Zymomonas, Agrobacterium, Flavobacterium, Rhodobacter, Rhodococcus, Streptomyces, Brevibacterium, Corynebacteria, Mycobacterium, Escherichia, Pantoea, Pseudomonas, Methylomonas, Methylobacter, Methylococcus, Methylosinus, Methylomicrobium, Methylocystis, Alcaligenes, Synechocystis, Synechococcus, Anabaena, Thiobacillus, Methanobacterium, Klebsiella, Methylophilus, Methylobacillus, Methylobacterium, Hyphomicrobium, Xanthobacter, Paracoccus, Nocardia, Arthrobacter, Rhodopseudomonas, Torulopsis, Rhodotorula,* and *Phaffia*.

Methylotrophs and *Methylomonas* sp. 16a as Microbial Hosts

Although a number of carotenoids have been produced from recombinant microbial sources [e.g., *E. coli* and *Candia utilis* for production of lycoene (Farmer, W. R. and Liao, J. C., *Biotechnol. Prog.* 17: 57–61 (2001); Wang et al., *Biotechnol Prog.* 16: 922–926 (2000); Misawa, N. and Shimada, H., *J. Biotechnol.* 59: 169–181 (1998); Shimada et al., *Appl. Environm. Microbiol.* 64:2676–2680 (1998)); *E. coli, Candia utilis* and *Pfaffia rhodozyma* for production of β-carotene (Albrecht et al., *Biotechnol. Lett.* 21: 791–795 (1999); Miura et al., *Appl. Environm. Microbiol.* 64:1226–1229 (1998); U.S. Pat. No. 5,691,190); *E. coli* and *Candia utilis* for production of zeaxanthin (Albrecht et al., supra; Miura et al., supra); *E. coli* and *Pfaffia rhodozyma* for production of astaxanthin (U.S. Pat. No. 5,466,599; U.S. Pat. No. 6,015,684; U.S. Pat. No. 5,182,208; U.S. Pat. No. 5,972,642); see also: U.S. Pat. No. 5,656,472, U.S. Pat. No. 5,545,816, U.S. Pat. No. 5,530,189, U.S. Pat. No. 5,530,188, U.S. Pat. No. 5,429,939, and U.S. Pat. No. 6,124,113), these methods of producing carotenoids using various combinations of different crt genes suffer from low yields and reliance on relatively expensive feedstocks. Thus, it would be desirable to identify a method that produces higher yields of carotenoids in a microbial host from an inexpensive feedstock.

There are a number of microorganisms that utilize single carbon substrates as their sole energy source. Such microorganisms are referred to herein as "C1 metabolizers". These organisms are characterized by the ability to use carbon substrates lacking carbon to carbon bonds as a sole source of energy and biomass. These carbon substrates include, but are not limited to: methane, methanol, formate, formaldehyde, formic acid, methylated amines (e.g., mono-, di- and trimethyl amine), methylated thiols, carbon dioxide, and various other reduced carbon compounds which lack any carbon-carbon bonds.

All C1 metabolizing microorganisms are generally classified as methylotrophs. Methylotrophs may be defined as any organism capable of oxidizing organic compounds that do not contain carbon-carbon bonds. However, facultative methylotrophs, obligate methylotrophs, and obligate methanotrophs are all various subsets of methylotrophs. Specifically:

Facultative methylotrophs have the ability to oxidize organic compounds which do not contain carbon-carbon bonds, but may also use other carbon substrates such as sugars and complex carbohydrates for energy and biomass. Facultative methylotrophic bacteria are found in many environments, but are isolated most commonly from soil, landfill and waste treatment sites. Many facultative methylotrophs are members of the β and γ subgroups of the Proteobacteria (Hanson et al., *Microb. Growth C1 Compounds.*, [Int. Symp.], $7^{th}$ (1993), pp 285–302. Murrell, J. Collin and Don P. Kelly, Eds. Intercept: Andover, UK; Madigan et al., *Brock Biology of Microorganisms*, $8^{th}$ ed., Prentice Hall: UpperSaddle River, N.J. (1997)).

Obligate methylotrophs are those organisms which are limited to the use of organic compounds that do not contain carbon-carbon bonds for the generation of energy.

Obligate methanotrophs are those obligate methylotrophs that have the distinct ability to oxidize methane.

Additionally, the ability to utilize single carbon substrates is not limited to bacteria but extends also to yeasts and fungi. A number of yeast genera are able to use single carbon substrates as energy sources in addition to more complex materials (i.e., the methylotrophic yeasts).

Although a large number of these methylotrophic organisms are known, few of these microbes have been successfully harnessed in industrial processes for the synthesis of materials. And, although single carbon substrates are cost-effective energy sources, difficulty in genetic manipulation of these microorganisms as well as a dearth of information about their genetic machinery has limited their use primarily to the synthesis of native products.

Despite these difficulties, many methanotrophs contain an inherent isoprenoid pathway which enables these organisms to synthesize pigments and provides the potential for one to envision engineering these microorganisms for production of various non-endogenous isoprenoid compounds. Since methanotrophs can use one carbon substrates (i.e., methane or methanol) as an energy source, it could be possible to produce carotenoids at low cost in these organisms. One such example wherein a methanotroph is engineered for production of β-carotene is described in WO 02/18617.

In the present invention, methods are provided for the expression of genes involved in the biosynthesis of carotenoid compounds in microorganisms that are able to use single carbon substrates as a sole energy source. The host microorganism may be any C1 metabolizer that has the ability to synthesize farnesyl pyrophosphate (FPP) as a metabolic precursor for carotenoids. More specifically, facultative methylotrophic bacteria suitable in the present invention include, but are not limited to: *Methylophilus, Methylobacillus, Methylobacterium, Hyphomicrobium, Xanthobacter, Bacillus, Paracoccus, Nocardia, Arthrobacter, Rhodopseudomonas,* and *Pseudomonas*. Specific methylotrophic yeasts useful in the present invention include, but are not limited to: *Candida, Hansenula, Pichia, Torulopsis,* and *Rhodotorula*. And, exemplary methanotrophs are included in, but not limited to, the genera *Methylomonas, Methylobacter, Methylococcus, Methylosinus, Methylocystis, Methylomicrobium,* and *Methanomonas*.

Of particular interest in the present invention are high growth obligate methanotrophs having an energetically favorable carbon flux pathway. For example, Applicants have discovered a specific strain of methanotroph having several pathway features that makes it particularly useful for carbon flux manipulation. This strain is known as *Methylomonas* 16a (ATCC PTA 2402) (U.S. Pat. No. 6,689,601); and, this particular strain and other related methylotrophs are preferred microbial hosts for expression of the gene products of this invention, useful for the production of $C_{40}$ carotenoids (WO 02/18617).

*Methylomonas* sp. 16a naturally produces $C_{30}$ carotenoids. Odom et al. has reported that expression of $C_{40}$ carotenoid genes in *Methylomonas* 16a produced a mixture of $C_{30}$ and $C_{40}$ carotenoids (WO 02/18617). Several of the genes involved in $C_{30}$ carotenoid production in this strain have been identified including (but not limited to) the crtN1, ald, crtN2, and crtN3 genes. Disruption of either the ald gene or the promoter driving expression of the crtN1/ald/crtN2 gene cluster created various non-pigmented mutants ("white mutants") more suitable for $C_{40}$ carotenoid production (U.S. Ser. No. 60/527,083, herby incorporated by reference). For example, non-pigmented *Methylomonas* sp. 16a strain MWM1000, was created by disrupting the ald and crtN1 genes.

The *Methylomonas* sp. 16a strain contains several anomalies in the carbon utilization pathway. For example, based on genome sequence data, the strain is shown to contain genes for two pathways of hexose metabolism. The Entner-Douderoff Pathway (which utilizes the keto-deoxy phosphogluconate aldolase enzyme) is present in the strain. It is generally well accepted that this is the operative pathway in obligate methanotrophs. Also present, however, is the Embden-Meyerhof Pathway (which utilizes the fructose bisphosphate aldolase enzyme). It is well known that this pathway is either not present, or not operative, in obligate methanotrophs. Energetically, the latter pathway is most favorable and allows greater yield of biologically useful energy, ultimately resulting in greater yield production of cell mass and other cell mass-dependent products in *Methylomonas* 16a. The activity of this pathway in the 16a strain has been confirmed through microarray data and biochemical evidence measuring the reduction of ATP. Although the 16a strain has been shown to possess both the Embden-Meyerhof and the Entner-Douderoff pathway enzymes, the data suggests that the Embden-Meyerhof pathway enzymes are more strongly expressed than the Entner-Douderoff pathway enzymes. This result is surprising and counter to existing beliefs concerning the glycolytic metabolism of methanotrophic bacteria. Applicants have discovered other methanotrophic bacteria having this characteristic, including for example, *Methylomonas clara* and *Methylosinus sporium*. It is likely that this activity has remained undiscovered in methanotrophs due to the lack of activity of the enzyme with ATP, the typical phosphoryl donor for the enzyme in most bacterial systems.

A particularly novel and useful feature of the Embden-Meyerhof pathway in strain 16a is that the key phosphofructokinase step is pyrophosphate-dependent instead of ATP-dependent. This feature adds to the energy yield of the pathway by using pyrophosphate instead of ATP.

In methanotrophic bacteria, methane is converted to biomolecules via a cyclic set of reactions known as the ribulose monophosphate pathway or RuMP cycle. This pathway is comprised of three phases, each phase being a series of enzymatic steps. The first step is "fixation" or incorporation of C-1 (formaldehyde) into a pentose to form a hexose or six-carbon sugar. This occurs via a condensation reaction between a 5-carbon sugar (pentose) and formaldehyde and is catalyzed by hexulose monophosphate synthase. The second phase is termed "cleavage" and results in splitting of that hexose into two 3-carbon molecules. One of those 3-carbon molecules is recycled back through the RuMP pathway and the other 3-carbon fragment is utilized for cell growth.

In methanotrophs and methylotrophs the RuMP pathway may occur as one of three variants. However, only two of these variants are commonly found: the FBP/TA (fructose bisphosphotase/transaldolase) pathway or the KDPG/TA (keto deoxy phosphogluconate/transaldolase) pathway (Dijkhuizen, L. and Devries, G. E., "The Physiology and biochemistry of aerobic methanol-utilizing gram negative and gram positive bacteria". In: *Methane and Methanol Utilizers*; Colin Murrell and Howard Dalton, Eds.; Plenum: NY, 1992).

*Methylomonas* sp. 16a is unique in the way it handles the "cleavage" steps where genes were found that carry out this conversion via fructose bisphosphate as a key intermediate. The genes for fructose bisphosphate aldolase and transaldolase were found clustered together on one piece of DNA. Secondly, the genes for the other variant involving the keto deoxy phosphogluconate intermediate were also found clustered together. Available literature teaches that these organisms (obligate methylotrophs and methanotrophs) rely solely on the KDPG pathway and that the FBP-dependent fixation pathway is utilized by facultative methylotrophs (Dijkhuizen et al., supra). Therefore the latter observation is expected, whereas the former is not. The finding of the FBP genes in an obligate methane-utilizing bacterium is both surprising and suggestive of utility. The FBP pathway is energetically favorable to the host microorganism due to the fact that more energy (ATP) is utilized than is utilized in the KDPG pathway. Thus, organisms that utilize the FBP pathway may have an energetic advantage and growth advantage over those that utilize the KDPG pathway. This advantage may also be useful for energy-requiring production pathways in the strain. By using this pathway, a methane-utilizing bacterium may have an advantage over other methane-utilizing organisms as production platforms for either single cell protein or for any other product derived from the flow of carbon through the RuMP pathway (e.g., carotenoids).

Accordingly, the present invention provides a method for the production of a carotenoid compound in a high growth, energetically favorable *Methylomonas* strain which:

(a) grows on a C1 carbon substrate selected from the group consisting of methane and methanol; and (b) comprises a functional Embden-Meyerhof carbon pathway, said pathway comprising a gene encoding a pyrophosphate-dependent phosphofructokinase enzyme.

Transformation of C1 Metabolizing Bacteria

Techniques for the transformation of C1 metabolizing bacteria are not well developed, although general methodology that is utilized for other bacteria, which is well known to those of skill in the art, may be applied. Electroporation has been used successfully for the transformation of: *Methylobacterium extorquens* AM1 (Toyama, H., et al., *FEMS Microbiol. Lett.* 166:1–7 (1998)), *Methylophilus methylotrophus* AS1 (Kim, C. S., and T. K. Wood. *Appl. Microbiol. Biotechnol.* 48:105–108 (1997)), and *Methylobacillus* sp. strain 12S (Yoshida, T., et al., *Biotechnol. Lett.*, 23: 787–791 (2001)). Extrapolation of specific electroporation parameters from one specific C1 metabolizing utilizing organism to another may be difficult, however, as is well to known to those of skill in the art.

Bacterial conjugation, relying on the direct contact of donor and recipient cells, is frequently more readily amenable for the transfer of genes into C1 metabolizing bacteria. Simplistically, this bacterial conjugation process involves mixing together "donor" and "recipient" cells in close contact with one another. Conjugation occurs by formation of cytoplasmic connections between donor and recipient bacteria, with direct transfer of newly synthesized donor DNA into the recipient cells. As is well known in the art, the recipient in a conjugation is defined as any cell that can accept DNA through horizontal transfer from a donor bacterium. The donor in conjugative transfer is a bacterium that contains a conjugative plasmid, conjugative transposon, or mobilizable plasmid. The physical transfer of the donor plasmid can occur in one of two fashions, as described below:

1. In some cases, only a donor and recipient are required for conjugation. This occurs when the plasmid to be transferred is a self-transmissible plasmid that is both conjugative and mobilizable (i.e., carrying both tra-genes and genes encoding the Mob proteins). In general, the process involves the following steps: 1.) Double-strand plasmid DNA is nicked at a specific site in oriT; 2.) A single-strand DNA is released to the recipient through a pore or pilus structure; 3.) A DNA relaxase enzyme cleaves the double-strand DNA at oriT and binds to a release 5' end (forming a relaxosome as the intermediate structure); and 4.) Subsequently, a complex of auxiliary proteins assemble at oriT to facilitate the process of DNA transfer.

2. Alternatively, a "triparental" conjugation is required for transfer of the donor plasmid to the recipient. In this type of conjugation, donor cells, recipient cells, and a "helper" plasmid participate. The donor cells carry a mobilizable plasmid or conjugative transposon. Mobilizable vectors contain an oriT, a gene encoding a nickase, and have genes encoding the Mob proteins; however, the Mob proteins alone are not sufficient to achieve the transfer of the genome. Thus, mobilizable plasmids are not able to promote their own transfer unless an appropriate conjugation system is provided by a helper plasmid (located within the donor or within a "helper" cell). The conjugative plasmid is needed for the formation of the mating pair and DNA transfer, since the plasmid encodes proteins for transfer (Tra) that are involved in the formation of the pore or pilus.

Examples of successful conjugations involving C1 metabolizing bacteria include the work of: Stolyar et al. (*Mikrobiologiya* 64(5): 686–691 (1995)); Motoyama, et al. (*Appl. Micro. Biotech.* 42(1): 67–72 (1994)); Lloyd, et al. (*Archives of Microbiology* 171(6): 364–370 (1999)); and Odom et al. (WO 02/18617).

In vitro Bio-Conversion of Carotenoids

Alternatively, it is possible to carry out the bioconversions of the present application in vitro. Where substrates for CrtE, CrtY, CrtI, CrtB, and CrtZ are not synthesized endogenously by the host cell it will be possible to add the substrate exogenously. In this embodiment the suitable carotenoid substrate may be solubilized with mild detergent (e.g., DMSO) or mixed with phospholipid vesicles. To assist in transport into the cell, the host cell may optionally be permeabilized with a suitable solvent such as toluene. Methods for this type of in-vitro bio-conversion of carotenoid substrates have basis in the art (see for example: Hundle, B. S., et al., *FEBS*, 315:329–334 (1993); and Bramley, P. M., et al., *Phytochemistry*, 26:1935–1939 (1987)).

Industrial Production using Recombinant Microorganisms

Where commercial production of the instant proteins are desired, a variety of culture methodologies may be applied. For example, large-scale production of a specific gene product over-expressed from a recombinant microbial host may be produced by both batch or continuous culture methodologies.

A classical batch culturing method is a closed system where the composition of the media is set at the beginning of the culture and not subject to artificial alterations during the culturing process. Thus, at the beginning of the culturing process the media is inoculated with the desired organism or organisms and growth or metabolic activity is permitted to occur while adding nothing to the system. Typically, however, a "batch" culture is batch with respect to the addition of carbon source and attempts are often made at controlling factors such as pH and oxygen concentration. In batch systems the metabolite and biomass compositions of the system change constantly up to the time the culture is terminated. Within batch cultures cells moderate through a static lag phase to a high growth log phase and finally to a stationary phase where growth rate is diminished or halted. If untreated, cells in the stationary phase will eventually die. Cells in log phase are often responsible for the bulk of production of end product or intermediate in some systems. Stationary or post-exponential phase production can be obtained in other systems.

A variation on the standard batch system is the Fed-Batch system. Fed-Batch culture processes are also suitable in the present invention and comprise a typical batch system with the exception that the substrate is added in increments as the culture progresses. Fed-Batch systems are useful when catabolite repression is apt to inhibit the metabolism of the cells and where it is desirable to have limited amounts of substrate in the media. Measurement of the actual substrate concentration in Fed-Batch systems is difficult and is therefore estimated on the basis of the changes of measurable factors such as pH, dissolved oxygen and the partial pressure of waste gases such as $CO_2$. Batch and Fed-Batch culturing methods are common and well known in the art and examples may be found in Brock (supra) and Deshpande (supra).

Commercial production of the instant proteins may also be accomplished with a continuous culture. Continuous cultures are an open system where a defined culture media is added continuously to a bioreactor and an equal amount of conditioned media is removed simultaneously for processing. Continuous cultures generally maintain the cells at a constant high liquid phase density where cells are primarily in log phase growth. Alternatively continuous culture may be practiced with immobilized cells where carbon and nutrients are continuously added, and valuable products, by-products or waste products are continuously removed from the cell mass. Cell immobilization may be performed using a wide range of solid supports composed of natural and/or synthetic materials.

Continuous or semi-continuous culture allows for the modulation of one factor or any number of factors that affect cell growth or end product concentration. For example, one method will maintain a limiting nutrient such as the carbon source or nitrogen level at a fixed rate and allow all other parameters to moderate. In other systems a number of factors affecting growth can be altered continuously while the cell concentration, measured by media turbidity, is kept constant. Continuous systems strive to maintain steady state growth conditions and thus the cell loss due to media being drawn off must be balanced against the cell growth rate in the culture. Methods of modulating nutrients and growth factors for continuous culture processes, as well as techniques for maximizing the rate of product formation, are well known in the art of industrial microbiology and a variety of methods are detailed by Brock, supra.

Fermentation media in the present invention must contain suitable carbon substrates. Suitable substrates may include, but are not limited to: monosaccharides (e.g., glucose and fructose), disaccharides (e.g., lactose or sucrose), polysaccharides (e.g., starch or cellulose or mixtures thereof) and unpurified mixtures from renewable feedstocks (e.g., cheese whey permeate, cornsteep liquor, sugar beet molasses, and barley malt). Additionally, the carbon substrate may also be one-carbon substrates such as carbon dioxide, methane or methanol for which metabolic conversion into key biochemical intermediates has been demonstrated. In addition to one and two carbon substrates, methylotrophic organisms are also known to utilize a number of other carbon-containing compounds such as methylamine, glucosamine and a variety of amino acids for metabolic activity. For example, methylotrophic yeast are known to utilize the carbon from methylamine to form trehalose or glycerol (Bellion et al., *Microb. Growth C1 Compd.*, [Int. Symp.], 7$^{th}$ (1993), 415–32. Murrell, J. Collin and Kelly, Don P, eds. Intercept: Andover, UK). Similarly, various species of *Candida* will metabolize alanine or oleic acid (Sulter et al., *Arch. Microbiol.* 153:485–489 (1990)). Hence it is contemplated that the source of carbon utilized in the present invention may-encompass a wide variety of carbon-containing substrates and will only be limited by the choice of organism.

Recombinant Production in Plants

Plants and algae are also known to produce carotenoid compounds. The crtE, idi, crtY, crtI, crtB and crtZ nucleic acid fragments of the instant invention may be used to create transgenic plants having the ability to express the microbial protein(s). Preferred plant hosts will be any variety that will support a high production level of the instant proteins. Suitable green plants will include, but are not limited to: soybean, rapeseed (*Brassica napus, B. campestris*), sunflower (*Helianthus annus*), cotton (*Gossypium hirsutum*), corn, tobacco (*Nicotiana tabacum*), alfalfa (*Medicago sativa*), wheat (*Triticum* sp.), barley (*Hordeum vulgare*), oats (*Avena sativa*, L), sorghum (*Sorghum bicolor*), rice (*Oryza sativa*), *Arabidopsis*, cruciferous vegetables (broccoli, cauliflower, cabbage, parsnips, etc.), melons, carrots, celery, parsley, tomatoes, potatoes, strawberries, peanuts, grapes, grass seed crops, sugar beets, sugar cane, beans, peas, rye, flax, hardwood trees, softwood trees, and forage grasses. Algal species include, but are not limited to, commercially significant hosts such as *Spirulina, Haemotacoccus*, and *Dunalliela*.

Over-expression of preferred carotenoid compounds may be accomplished by first constructing chimeric genes of the present invention in which the coding region(s) are operably linked to promoters capable of directing expression of the gene(s) in the desired tissues at the desired stage of development. For reasons of convenience, the chimeric genes may comprise promoter sequences and translation leader sequences derived from the same genes. 3' Non-coding sequences encoding transcription termination signals must also be provided. The instant chimeric genes may also comprise one or more introns in order to facilitate gene expression.

Any combination of any promoter and any terminator capable of inducing expression of a coding region may be used in the chimeric genetic sequence. Some suitable examples of promoters and terminators include those from nopaline synthase (nos), octopine synthase (ocs) and cauliflower mosaic virus (CaMV) genes. One type of efficient plant promoter that may be used is a high level plant promoter. Such promoters, in operable linkage with the genetic sequences of the present invention, should be capable of promoting expression of the present gene product. High level plant promoters that may be used in this invention include, for example: 1.) the promoter of the small subunit (ss) of the ribulose-1,5-bisphosphate carboxylase from soybean (Berry-Lowe et al., *J. Molecular and App. Gen.*, 1:483–498 (1982)); and 2.) the promoter of the chlorophyll a/b binding protein. These two promoters are known to be light-induced in plant cells (see, for example, *Genetic Engineering of Plants, an Agricultural Perspective*, A. Cashmore, Ed. Plenum: NY (1983), pp 29–38; Coruzzi, G. et al., *J. Biol. I Chem.*, 258:1399 (1983); and Dunsmuir, P. et al., *J. Mol. Appl. Genet.*, 2:285 (1983)).

Plasmid vectors comprising the instant chimeric genes can then be constructed. The choice of plasmid vector depends upon the method that will be used to transform host plants. The skilled artisan is well aware of the genetic elements that must be present on the plasmid vector in order to successfully transform, select and propagate host cells containing the chimeric gene(s). The skilled artisan will also recognize that different independent transformation events will result in different levels and patterns of expression (Jones et al., *EMBO J.* 4:2411–2418 (1985); De Almeida et al., *Mol. Gen. Genetics* 218:78–86 (1989)), and thus multiple events must be screened in order to obtain lines displaying the desired expression level and pattern. Such screening may be accomplished by Southern analysis of DNA blots (Southern, *J. Mol. Biol.* 98:503 (1975)), Northern analysis of mRNA expression (Kroczek, *J. Chromatogr. Biomed. Appl.*, 618 (1–2):133–145 (1993)), Western analysis of protein expression, or phenotypic analysis.

For some applications it will be useful to direct the instant proteins to different cellular compartments. It is thus envisioned that the chimeric genes described above may be further supplemented by altering the coding sequences to encode enzymes with appropriate intracellular targeting sequences added and/or with targeting sequences that are already present removed, such as: 1.) transit sequences (Keegstra, K., *Cell* 56:247–253 (1989)); 2.) signal sequences; or 3.) sequences encoding endoplasmic reticulum localization (Chrispeels, J. J., *Ann. Rev. Plant Phys. Plant Mol. Biol.* 42:21–53 (1991)) or nuclear localization signals (Raikhel, N., *Plant Phys.* 100:1627–1632 (1992)). While the references cited give examples of each of these, the list is not exhaustive and more targeting signals of utility may be discovered in the future that are useful in the invention.

Protein Engineering

It is contemplated that the present crtE, idi, crtY, crtI, crtB, and/or crtZ nucleotides may be used to produce gene products having enhanced or altered activity. Various methods are known for mutating a native gene sequence to produce a gene product with altered or enhanced activity including, but not limited to: 1.) error prone PCR (Melnikov et al., *Nucleic Acids Research*, 27(4):1056–1062 (Feb. 15, 1999)); 2.) site-directed mutagenesis (Coombs et al., *Proteins* (1998), pp 259–311, 1 plate. Angeletti, Ruth Hogue, Ed., Academic: San Diego, Calif.); and 3.) "gene shuffling" (U.S. Pat. No. 5,605,793; U.S. Pat. No. 5,811,238; U.S. Pat. No. 5,830,721; and U.S. Pat. No. 5,837,458, incorporated herein by reference).

The method of gene shuffling is particularly attractive due to its facile implementation, and high rate of mutagenesis and ease of screening. The process of gene shuffling involves the restriction endonuclease cleavage of a gene of interest into fragments of specific size in the presence of additional populations of DNA regions of both similarity to or difference to the gene of interest. This pool of fragments will then be denatured and reannealed to create a mutated gene. The mutated gene is then screened for altered activity.

The instant microbial sequences of the present invention may be mutated and screened for altered or enhanced activity by this method. The sequences should be double-stranded and can be of various lengths ranging from 50 bp to 10 kB. The sequences may be randomly digested into fragments ranging from about 10 bp to 1000 bp, using restriction endonucleases well known in the art (Maniatis, supra). In addition to the instant microbial sequences, populations of fragments that are hybridizable to all or portions of the microbial sequence may be added. Similarly, a population of fragments which are not hybridizable to the instant sequence may also be added. Typically these additional fragment populations are added in about a 10 to 20 fold excess by weight as compared to the total nucleic acid. Generally, if this process is followed, the number of different specific nucleic acid fragments in the mixture will be about 100 to about 1000. The mixed population of random nucleic acid fragments are denatured to form single-stranded nucleic acid fragments and then reannealed. Only those single-stranded nucleic acid fragments having regions of homology with other single-stranded nucleic acid fragments will reanneal. The random nucleic acid fragments may be denatured by heating. One skilled in the art could determine the conditions necessary to completely denature the double-stranded nucleic acid. Preferably the temperature is from about 80° C. to 100° C. The nucleic acid fragments may be reannealed by cooling. Preferably the temperature is from about 20° C. to 75° C. Renaturation can be accelerated by the addition of polyethylene glycol ("PEG") or salt. A suitable salt concentration may range from 0 mM to 200 mM. The annealed nucleic acid fragments are then incubated in the presence of a nucleic acid polymerase and dNTPs (i.e., dATP, dCTP, dGTP and dTTP). The nucleic acid polymerase may be the Klenow fragment, the Taq polymerase or any other DNA polymerase known in the art. The polymerase may be added to the random nucleic acid fragments prior to annealing, simultaneously with annealing or after annealing. The cycle of denaturation, renaturation and incubation in the presence of polymerase is repeated for a desired number of times. Preferably the cycle is repeated from about 2 to 50 times, more preferably the sequence is repeated from 10 to 40 times. The resulting nucleic acid is a larger double-stranded polynucleotide ranging from about 50 bp to about 100 kB and may be screened for expression and altered activity by standard cloning and expression protocols (Manatis, supra).

Furthermore, a hybrid protein can be assembled by fusion of functional domains using the gene shuffling (exon shuffling) method (Nixon et al., *Proc. Natl. Acad. Sci. USA*, 94:1069–1073 (1997)). The functional domain of the instant gene can be combined with the functional domain of other genes to create novel enzymes with desired catalytic function. A hybrid enzyme may be constructed using PCR overlap extension methods and cloned into various expression vectors using the techniques well known to those skilled in art.

EXAMPLES

The present invention is further defined in the following Examples. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions.

General Methods

Standard recombinant DNA and molecular cloning techniques used in the Examples are well known in the art and are described by: Maniatis (supra), Silhavy et al. (supra), and Ausubel et al. (supra).

Materials and methods suitable for the maintenance and growth of bacterial cultures are well known in the art. Techniques suitable for use in the following examples may be found as set out in: *Manual of Methods for General Bacteriology* (Phillipp Gerhardt, R. G. E. Murray, Ralph N. Costilow, Eugene W. Nester, Willis A. Wood, Noel R. Krieg and G. Briggs Phillips, Eds), American Society for Microbiology: Washington, D.C. (1994)); or in Brock et al. (supra). All reagents, restriction enzymes and materials used for the growth and maintenance of bacterial cells were obtained from Aldrich Chemicals (Milwaukee, Wis.), DIFCO Laboratories (Detroit, Mich.), GIBCO/BRL (Gaithersburg, Md.), or Sigma Chemical Company (St. Louis, Mo.) unless otherwise specified.

Sequence data was generated on an ABI Automatic sequencer using dye terminator technology (U.S. Pat. No. 5,366,860; EP 272,007) using a combination of vector and insert-specific primers. Sequence editing and assembly was performed in Sequencher™ version 4.0.5 (Gene Codes Corp., Ann Arbor, Mich.). All sequences represent coverage at least two times in both directions. Manipulations of genetic sequences were accomplished using Vector NTI programs (InforMax, Inc., Bethesda, Md.)., Pairwise comparisons were performed using the default values in Vector NTI. BLAST analysis were performed using the default values set by the National Center for Biotechnological Information (NCBI).

The meaning of abbreviations is as follows: "sec" means second(s), "min" means minute(s), "h" means hour(s), "d" means day(s), "μL" means microliter(s), "mL" means milliliter(s), "L" means liter(s), "μM" means micromolar, "mM" means millimolar, "M" means molar, "mmol" means millimole(s), "μmol" mean micromole(s), "g" means gram (s), "μg" means microgram(s), "ng" means nanogram(s), "U" means unit(s), "bp" means base pair(s), and "kB" means kilobase(s).

Example 1

Isolation of Carotenoid-Producing Strain *Pantoea agglomerans* DC404

The present Example describes the isolation and identification of a yellow-pigmented bacterium *Pantoea agglomerans* strain DC404, which belongs to the family of Enterobacteriaceae. Analysis of the native carotenoids produced in this organism confirmed production of zeaxanthin, in addition to various zeaxanthin precursors and zeaxanthin derivatives.

Strain isolation and typing: To isolate novel carotenoid-producing bacterial strains, pigmented microbes were isolated from a collection of environmental samples. The soil from a residential vegetable garden in Wilmington, Del. was collected and resuspended in Luria-Broth (LB). A 10 μL loopful of resuspension was streaked onto LB plates and the plates were incubated at 30° C. Pigmented bacteria with diverse colony appearances were picked and streaked twice to homogeneity on LB plates and incubated at 30° C. From these colonies, one which formed pale yellow smooth translucent colonies was designated as "strain DC404".

16S rRNA gene sequencing was performed to type strain DC404. Specifically, the 16S rRNA gene of the strain was amplified by PCR using primers HK12 (SEQ ID NO:13) and JCR14 (SEQ ID NO:14). The amplified 16S rRNA genes were purified using a QIAquick PCR Purification Kit according to the manufacturer's instructions (Qiagen) and sequenced on an automated ABI sequencer. The sequencing reactions were initiated with primers HK12, JCR14, and JCR15 (SEQ ID NO:15). The assembled 1324 bp 16S rRNA gene sequence (SEQ ID NO:16) of DC404 was used as the query sequence for a BLASTN search (Altschul, et al., Nucleic Acids Res. 25:3389–3402(1997)) against GenBank®.

BLAST analysis indicated that strain DC404 belonged to the Enterobacteriaceae family. Its 16S rRNA gene sequence showed sequence similarities to several different species within this family, with the top hit (96% identity) to *Salmonella typhimurium*. Other species that shared 96% identity with the 16S rRNA gene sequence of strain DC404, according to the analysis described above, included: *Klebsiella oxytoca, Enterobacter cloacae, Citrobacter amalonaticus, Erwinia amylovora*, and *Pantoea agglomerans*. Consistent with the relative low homology of the hit (only 96% identity), however, biochemical tests using BBL Enterotube™ II (Becton Dickinson, Cockeysville, Md.) indicated that DC404 was not a *Salmonella* species.

DC404 was further characterized according to its fatty acid profile by an external company, Microbial ID., Inc. (Newark, Del.). Fatty acid profiling by gas chromatography indicated that strain DC404 was most closely related to *Pantoea agglomerans* (the similarity index value was 0.557). Similarity index is a numerical value that expresses how closely the fatty acid composition of an unknown sample compares with the mean fatty acid composition of the strains used to create the library entry listed as its match. An exact match of the fatty acid make-up of the unknown sample to the mean of a library entry results in a similarity index of 1.000. A similarity index between 0.400 and 0.600 may be a species match, indicating an atypical strain. Since the 16S rRNA analysis of strain DC404 had also identified *Pantoea agglomerans* as one of the top BLAST hits (sharing 96% identity), strain DC404 was designated as an atypical strain of *Pantoea agglomerans*.

Carotenoid analysis of DC404: The yellow pigment in DC404 was extracted and analyzed by HPLC. The strain was grown in 200 mL LB at 30° C. for 2 days and then cells were harvested by centrifugation at 4000 g for 30 min. The cell pellet was extracted with 10 mL acetone. The solvent was dried under nitrogen and the carotenoids were resuspended in 0.5 mL acetone. The extraction was filtered with an Acrodisc CR25 mm syringe filter (Pall Corporation, Ann Arbor, Mich.) and then concentrated in 0.1 mL 10% acetone+90% acetonitrile for HPLC analysis using an Agilent Series 1100 LC/MSD SI (Agilent, Foster City, Calif.).

Sample (20 µL) was loaded onto a 150 mm×4.6 mm ZORBAX C18 (3.5 µm particles) column (Agilent Technologies, Inc.). The column temperature was kept at 40° C. The flow rate was 1 mL/min, while the solvent running program used was:

0–2 min: 95% buffer A and 5% buffer B;
2–10 min: linear gradient from 95% buffer A and 5% buffer B to 60% buffer A and 40% buffer B;
10–12 min: linear gradient from 60% buffer A and 40% buffer B to 50% buffer A and 50% buffer B;
12–18 min: 50% buffer A and 50% buffer B; and,
18–20 min: 95% buffer A and 5% buffer B.

Buffer A was 95% acetonitrile and 5% $dH_2O$; buffer B was 100% tetradehydrofuran.

HPLC analysis (FIG. 3) indicated that strain DC404 produced zeaxanthin (6.28 min peak), β-cryptoxanthin (10.23 min peak) and β-carotene (13.02 min peak) by comparison with authentic standards. Specifically, zeaxanthin and β-cryptoxanthin standards were purchased from CaroteNature (Lupsingen, Switzerland) and a β-carotene standard was purchased from Sigma (St. Louis, Mo.). MS analysis confirmed that the molecular weight of the zeaxanthin peak was 569, that of the β-cryptoxanthin peak was 553, and that of the β-carotene peak was 537. The peak that eluted at 3.22 min was most likely zeaxanthin monoglucoside, as suggested by its molecular weight of 731.

Example 2

Identification of Pigmented Cosmid Clones of *Pantoea agglomerans* DC404

Example 2 describes the construction of an *E. coli* cosmid clone capable of expressing an ~40 kB fragment of genomic DNA from *Pantoea agglomerans* DC404. This transformant produced predominantly zeaxanthin. No zeaxanthin glucosides were detected in the *E. coli* cosmid clone.

Chromosomal DNA preparation: Strain DC404 was grown in 25 mL LB medium at 30° C. overnight with aeration. Bacterial cells were centrifuged at 4,000 g for 10 min. The cell pellet was gently resuspended in 5 mL of 50 mM Tris-10 mM EDTA (pH 8) and lysozyme was added to a final concentration of 2 mg/mL. The suspension was incubated at 37° C. for 1 h. Sodium dodecyl sulfate was then added to a final concentration of 1% and proteinase K was added at 100 µg/mL. The suspension was incubated at 55° C. for 2 h. The suspension became clear and the clear lysate was extracted twice with an equal volume of phenol:chloroform:isoamyl alcohol (25:24:1) and once with chloroform:isoamyl alcohol (24:1). After centrifuging at 4,000 rpm for 20 min, the aqueous phase was carefully removed and transferred to a new tube. Two volumes of ethanol were added and the DNA was gently spooled with a sealed glass pasteur pipet. The DNA was dipped into a tube containing 70% ethanol. After air drying, the DNA was resuspended in 400 µL of TE (10 mM Tris-1 mM EDTA, pH 8) with RNaseA (100 µg/mL) and stored at 4° C. The concentration and purity of DNA was determined spectrophotometrically by $OD_{260}/OD_{280}$.

Cosmid library construction: A cosmid library of DC404 was constructed using the pWEB cosmid cloning kit from Epicentre Technologies (Madison, Wis.) following the manufacturer's instructions. Genomic DNA was sheared by passing it through a syringe needle. The sheared DNA was end-repaired and size-selected on low-melting-point agarose by comparison with a 40 kB standard. DNA fragments approximately 40 kB in size were purified and ligated into the blunt-ended cloning-ready pWEB cosmid vector. The library was packaged using ultra-high efficiency MaxPlax Lambda Packaging Extracts, and plated on EPI100 *E. coli* cells. Two yellow colonies were identified from the cosmid library clones. Since cosmid DNA from the two clones had similar restriction digestion patterns, further analysis was performed on a single clone.

Carotenoid analysis of the yellow cosmid clone: The carotenoids in *E. coli* EPI100 containing cosmid pWEB-404 were analyzed by LC-MS, as described in EXAMPLE 1. The HPLC result is shown in FIG. 4. The 6.27 min peak was identified as zeaxanthin, based on its UV spectrum, molecular weight and comparison with the authentic standard. Significant amounts of neither β-carotene nor β-cryptoxanthin intermediates accumulated; and, no zeaxanthin glucoside was produced. The predominant zeaxanthin monoglucoside peak observed in DC404 (FIG. 3) was not present in this E. coli cosmid clone. The small peak at 3.56 min was not an isomer of zeaxanthin monoglucoside since its molecular weight does not match that of zeaxanthin monoglucoside (731 Dalton). Absence of zeaxanthin glucosides within E. coli containing cosmid pWEB-404 suggested that the crtX gene encoding zeaxanthin glucosyltransferase may not reside on cosmid pWEB-404.

Example 3

Identification of Carotenoid Biosynthesis Genes

This Example desribes the identification of Pantoea agglomerans DC404 crtE, idi, crtY, crtI, crtB, and crtZ genes in cosmid pWEB-404, and provides a comparison of the relatedness of these genes with respect to other known Panteoa crt genes. In contrast to the genetic organization of the lower carotenoid biosynthetic pathway genes in other Panteoa, the crtX gene was not present as part of the gene cluster on the cosmid described herein from P. agglomerans DC404.

HPLC analysis suggested that cosmid pWEB-404 should contain genes for synthesis of zeaxanthin. To sequence the carotenoid synthesis genes, cosmid DNA pWEB-404 was subjected to in vitro transposition using the EZ::TN<TET-1> kit from Epicentre (Madison, Wis.) following the manufacturer's instructions. Two hundred tetracycline resistant transposon insertions were sequenced from the end of the transposon using the TET-1 FP-1 Forward primer (SEQ ID NO:17). Sequence assembly was performed with the Sequencher program (Gene Codes Corp., Ann Arbor, Mich.). A 8814 bp contig (SEQ ID NO:18) containing 6 genes of the carotenoid biosynthesis pathway from DC404 was assembled (FIG. 5).

Genes encoding crtE, idi, crtY, crtI, crtB, and crtZ were identified by conducting BLAST (Basic Local Alignment Search Tool; Altschul et al., (supra))) searches for similarity to sequences contained in the BLAST "nr" database (comprising all non-redundant GenBank® CDS translations, sequences derived from the 3-dimensional structure Brookhaven Protein Data Bank, the SWISS-PROT protein sequence database, EMBL, and DDBJ databases). Each sequence was analyzed for similarity to all publicly available DNA sequences contained in the "nr" database using the BLASTN algorithm provided by the National Center for Biotechnology Information (NCBI). The DNA sequence was translated in all reading frames and compared for similarity to all publicly available protein sequences contained in the "nr" database using the BLASTX algorithm (Gish, W. and States, D. J., Nature Genetics 3:266–272 (1993)) provided by the NCBI.

All comparisons were done using either the BLASTNnr or BLASTXnr algorithm. The results of the BLAST comparisons are given in Table 2, which summarizes the sequences to which each gene has the most similarity. Table 2 displays data based on the BLASTXnr algorithm with values reported in expect values. The Expect value estimates the statistical significance of the match, specifying the number of matches, with a given score, that are expected in a search of a database of this size absolutely by chance.

The nucleotide and amino acid sequences were also compared with those from other Pantoea strains, using the Vector NTI program, supra). Table 3 summarizes the identity of the pairwise comparisons.

TABLE 2

Top BLAST Hits for the Carotenoid Biosynthesis Genes of Pantoea agglomerans DC404

| ORF Name | Gene Name | Similarity Identified | SEQ ID base | SEQ ID Peptide | % Identity[a] | % Similarity[b] | E-value[c] | Citation |
|---|---|---|---|---|---|---|---|---|
| 1 | crtE | Geranylgeranyl pryophosphate synthetase (or GG synthetase, or farnesyltranstransferase) EC 2.5.1.29 gi\|27228290\|gb\|AAN85596.1crtE [Pantoea stewartii] | 1 | 2 | 65 | 77 | e–97 | deSouza, M. L. et al. (2002), Unpublished |
| 2 | idi | Isopentenyl pyrophosphate isomerase gi\|1723373\|sp\|Q01335\|IDI2_ERWHE [Pantoea agglomerans] | 3 | 4 | 67 | 78 | e–124 | Hundle, B., et al., Mol. Gen. Genet. 245 (4) 406–416 (1994 |
| 3 | crtY | Lycopene cyclase gi\|18143447\|dbj\|BAB79602.1 [Pantoea agglomerans pv. Miletiae] | 5 | 6 | 61 | 74 | e–134 | Kamiunten, H. and Hirata, R. (2001) unpublished |
| 4 | crtI | Phytoene desaturase EC 1.3.—.— gi\|27228293\|gb\|AAN85599.1 [Pantoea stewartii] | 7 | 8 | 82 | 89 | 0.0 | deSouza, M. L. et al. (2002), Unpublished |
| 5 | crtB | Phytoene synthaseEC2.5.1.— gi\|22474503\|2dbj\|BAA14128.2\|crtB [Pantoea ananatis] | 9 | 10 | 67 | 75 | e–115 | Misawa, N., et al., J. Bacterio 172 (12): :6704–6712 (1990) |
| 6 | crtZ | Beta-carotene hydroxylase gi\|117526\|sp\|P21688\|CRTZ_PANAN [Pantoea ananatis] | 11 | 12 | 73 | 82 | 2e–75 | Misawa, N., et al., J. Bacterio 172 (12):: 6704–6712 (1990) |

[a] % Identity is defined as percentage of amino acids that are identical between the two proteins.
[b] % Similarity is defined as percentage of amino acids that are identical or conserved between the two proteins.
[c] Expect value. The Expect value estimates the statistical significance of the match, specifying the number of matches, with a given score, that are expected in a search of a database of this size absolutely by chance.

TABLE 3

Pairwise Comparison of the Carotenoid Biosynthesis Genes from  
*Pantoe aagglomerans* DC404 with those from other *Pantoea* Strains

| Source/gene | *Pantoea ananatis*[a] DNA | Amino acid | *Pantoea agglomerans*[b] DNA | Amino acid | *Pantoea stewartii*[c] DNA | Amino acid |
|---|---|---|---|---|---|---|
| DC404, crtE | 66% | 62% | 61% | 54% | 66% | 63% |
| DC404, idi  | NA[d] | NA | 68% | 66% | NA | NA |
| DC404, crtY | 60% | 57% | 61% | 60% | 60% | 58% |
| DC404, crtI | 71% | 80% | 73% | 77% | 72% | 82% |
| DC404, crtB | 66% | 67% | 68% | 61% | 63% | 66% |
| DC404, crtZ | 66% | 70% | 66% | 65% | 68% | 69% |

[a]*Pantoea ananatis*, GenBank ® Accession Number D90087  
[b]*Pantoea agglomerans* strain EHO-10, GenBank ® Accession Number M87280  
[c]*Pantoea stewartii*, GenBank ® Accession Number AY166713  
[d]NA = Not applicable.

A comparison of the genetic organization of the crt gene cluster in various *Pantoea* species also revealed interesting differences (FIG. 5) concerning the presence of the genes idi and crtX. The gene idi encoding isopentenyl pyrophosphate isomerase is involved in the upstream isoprenoid pathway and is usually not present in the crt gene cluster—, for example, the genetic organization of the crtEXYIBZ cluster in *Pantoea ananatis* (GenBank® Accession No. D90087) and *Pantoea stewartii* (GenBank® Accession No. AY1667131). Occasionally, however, idi is found to be part of the crt gene operon as discovered in *Pantoea agglomerans* EHO-10 (GenBank® Accession No. M87280). According to BLAST analyses conducted by the Applicants' herein, the "hypothetical protein" contained within the carotenogenic cluster of crtE-hypothetical protein-crtX-crtY-crtI-crtB-crtZ of *P. agglomerans* EHO-10 (GenBank® Accession No. M87280) should be considered as comprising crtE-idi-crtX-crtY-crtI-crtB-crtZ. Similarly, idi is also present in the crt gene cluster of *Pantoea agglomerans* DC404, and is downstream of the crtE gene. As shown in Table 3, however, the idi of strain DC404 shares only 68% identity with the idi of EHO-10.

Concerning the crtX gene, strain DC404 is unique as compared to the other *Panteoa* species with respect to the absence of this gene in the carotenogenic gene cluster described herein (FIG. 5). Further, the *E. coli* cosmid clone pWEB-404 containing the crt gene cluster from DC404 does not contain the crtX gene since the cosmid clone produces only zeaxanthin and no zeaxanthin glucosides. Despite the lack of the crtX gene in the gene cluster described herein, DC404 produces predominantly zeaxanthin monoglucoside and thus must have a crtX gene. It is concluded that the crtX gene is located elsewhere in the DC404 chromosome and not linked with the crt gene cluster. The sequence of crtX in strain DC404 has not been identified at this time.

Example 4

Expression of the crtEidiYIB Gene Cluster of *Pantoea agglomerans* DC404 in *Methylomonas* sp. 16a The following Example describes the introduction of the crt gene cluster comprising the crtEidiYIB genes from *Pantoea agglomerans* DC404 (Example 3) into *Methylomonas* 16a (ATCC PTA 2402) to enable the synthesis of desirable 40-carbon carotenoids, such as β-carotene.

First, primers pWEB-404F: 5'-GAATTCACTAGTCGAGACGCCGGGTACCAACCA-T-3' (SEQ ID NO:19) and pWEB-404R: 5'-GAATTCTAGCGCGGGCGCTGCCAGA-3' (SEQ ID NO:20) were used to amplify a fragment from DC404 containing the crtEidiYIB genes by PCR. Cosmid DNA pWEB-404 was used as the template with Pfu Turbo polymerase (Stratagene, La. Jolla, Calif.), and the following thermocycler conditions: 92° C. (5 min); 94° C. (1 min), 60° C. (1 min), 72° C. (9 min) for 25 cycles; and 72° C. (10 min). A single product of approximately 5.6 kB was observed following gel electrophoresis. Taq polymerase (Perkin Elmer) was used in a ten minute 72° C. reaction to add additional 3' adenosine nucleotides to the fragment for TOPO cloning into pTrcHis2-TOPO (Invitrogen). Following transformation to *E. coli* TOP10 cells, several colonies appeared bright yellow in color, indicating that they were producing a carotenoid compound. The gene cluster was then subcloned into the broad host range vector pBHR1 (MoBiTec, LLC, Marco Island, Fla.), and electroporated into *E. coli* 10G cells (Lucigen, Middletown, Wis.). The transformants containing the resulting plasmid, pDCQ330, were selected on LB medium containing 50 μg/mL kanamycin.

Plasmid pDCQ330 was transferred into *Methylomonas* 16a by tri-parental conjugal mating. The *E. coli* helper strain containing pRK2013 (ATCC No. 37159) and the *E. coli* 10G donor strain containing pDCQ330 were growing overnight in LB medium containing kanamycin (50 μg/mL), washed three times in LB, and resuspended in a volume of LB representing approximately a 60-fold concentration of the original culture volume.

The *Methylomonas* 16a strain MWM1000 (Δald/crtN1) contained a single crossover knockout of the ald/crtN1 genes, which disrupted the synthesis of the native $C_{30}$ carotenoids (U.S. Ser. No. 60/527,083). This Δald/crtN1 strain was growing as the recipient using the general conditions described in WO 02/18617. Briefly, *Methylomonas* 16a strain MWM1000 was growing in serum stoppered Wheaton bottles (Wheaton Scientific, Wheaton Ill.) using a gas/liquid ratio of at least 8:1 (i.e., 20 mL of Nitrate liquid "BTZ-3" media in 160 mL total volume) at 30° C. with constant shaking.

Nitrate liquid medium, also referred to herein as "defined medium" or "BTZ-3" medium was comprised of various salts mixed with Solution 1 as indicated below (Tables 4 and 5) or where specified the nitrate was replaced with 15 mM ammonium chloride. Solution 1 provides the composition for 100-fold concentrated stock solution of trace minerals.

TABLE 4

Solution 1*

| | MW | Conc. (mM) | g per L |
|---|---|---|---|
| Nitriloacetic acid | 191.1 | 66.9 | 12.8 |
| $CuCl_2 \times 2H_2O$ | 170.48 | 0.15 | 0.0254 |
| $FeCl_2 \times 4H_2O$ | 198.81 | 1.5 | 0.3 |
| $MnCl_2 \times 4H_2O$ | 197.91 | 0.5 | 0.1 |
| $CoCl_2 \times 6H_2O$ | 237.9 | 1.31 | 0.312 |
| $ZnCl_2$ | 136.29 | 0.73 | 0.1 |
| $H_3BO_3$ | 61.83 | 0.16 | 0.01 |
| $Na_2MoO_4 \times 2H_2O$ | 241.95 | 0.04 | 0.01 |
| $NiCl_2 \times 6H_2O$ | 237.7 | 0.77 | 0.184 |

*Mix the gram amounts designated above in 900 mL of $H_2O$, adjust to pH = 7, and add $H_2O$ to an end volume of 1 L. Keep refrigerated.

TABLE 5

| Nitrate liquid medium (BTZ-3)** | | | |
|---|---|---|---|
| | MW | Conc. (mM) | g per L |
| NaNO$_3$ | 84.99 | 10 | 0.85 |
| KH$_2$PO$_4$ | 136.09 | 3.67 | 0.5 |
| Na$_2$SO$_4$ | 142.04 | 3.52 | 0.5 |
| MgCl$_2$ × 6H$_2$O | 203.3 | 0.98 | 0.2 |
| CaCl$_2$ × 2H$_2$O | 147.02 | 0.68 | 0.1 |
| 1 M HEPES (pH 7) | 238.3 | | 50 mL |
| Solution 1 | | | 10 mL |

**Dissolve in 900 mL H$_2$O. Adjust to pH = 7, and add H$_2$O to give 1 L. For agar plates: Add 15 g of agarose in 1 L of medium, autoclave, let cool down to 50° C., mix, and pour plates.

The standard gas phase for cultivation contains 25% methane in air. The MWM1000 recipient was cultured under these conditions for 48 h in BTZ-3 medium, washed three times in BTZ-3, and resuspended in a volume of BTZ-3 representing a 150-fold concentration of the original culture volume.

The donor, helper, and recipient cell pastes were then combined in ratios of 1:1:2, respectively, on the surface of BTZ-3 agar plates containing 0.5% (w/v) yeast extract. Plates were maintained at 30° C. in 25% methane for 16–72 hours to allow conjugation to occur, after which the cell pastes were collected and resuspended in BTZ-3. Dilutions were plated on BTZ-3 agar containing kanamycin (50 μg/mL) and incubated at 30° C. in 25% methane for up to 1 week. Yellow transconjugants were streaked onto BTZ-3 agar with kanamycin (50 μg/mL).

For analysis of carotenoid composition, transconjugants were cultured in 25 mL BTZ-3 containing kanamycin (50 μg/mL) and incubated at 30° C. in 25% methane as the sole carbon source for 3–4 days. The cells were harvested by centrifugation and frozen at −20° C. After thawing, the pellets were extracted and carotenoid content was analyzed by HPLC, as described in Example 1.

HPLC analysis of extracts from *Methylomonas* 16a MWM1000 containing pDCQ330 showed almost exclusive production of β-carotene (FIG. 6). The retention time, UV spectrum and the molecular weight of the 14 min peak match those of the authentic β-carotene standard (Sigma). This confirmed the synthesis of C$_{40}$ carotenoids in this methanotrophic host using the crtEidiYIB gene cluster from DC404.

SEQUENCE LISTING

<160> NUMBER OF SEQ ID NOS: 20

<210> SEQ ID NO 1
<211> LENGTH: 906
<212> TYPE: DNA
<213> ORGANISM: Pantoea agglomerans strain DC404

<400> SEQUENCE: 1

```
atgacaagac cctttgaaac acatcccggt cacgacgggg aactgcatga gctgcacgct      60
gccctgcaac gtcgcctgga tgaactgctg cccgttggcg atgagcggga tcgggtcagc     120
agcgcaatgc gcgaaggcgt actggcaccg gggaaacgca ttcgcccgct gctcctgatc     180
ctcgccgccc gcgacctcgg ctgcgatcgc gaccacccg gcctgctgga tatggcctgt      240
gcggtggaaa tggtgcacgc ctcgtcgctg atcctcgacg atattccctg catggataac     300
gcggcgctcc ggcgcggtcg ccctaccatt catcgccagt atggtgaaga cgtggcaatt     360
ctcgctgcgg tagcgttgct cagcagcgcc tttggcgtga tggtcgcggc gcagggattg     420
tctcccgagt gccgcagcca ggcggtggcg gagctgtcga tggcggtcgg tacccagggt     480
ctggtgcagg tcagtataaa ggatctgcgt gaaggcaccg ccccgcgcag cgccgaggag     540
atcgccacca ccaacgaact gaaaaccagc gtgctgtttg gtgccacgct gcaaatcgcg     600
gccctggcgg caggcgcctc gccggcgcg cgccagaaaa tgcgctgctt tgcgcaggat      660
ttaggccagg cgttccagct gctggacgat ctggcggacg gccatgccgg gaccggcaaa     720
gacatcaata aggacgcggg taagtccacg ctggtggcga tgctcggcag cgacgcggtg     780
cgcgagcggc tcgacaccca tctgcgccgc gcagacgccc atttttcacg cgcctgcgga     840
aaaaaccagg ccacgcgacg ctttatgcac gcctggtttt caaaacagct ggccgcgttt     900
agctga                                                              906
```

<210> SEQ ID NO 2
<211> LENGTH: 301
<212> TYPE: PRT

<213> ORGANISM: Pantoea agglomerans strain DC404

<400> SEQUENCE: 2

```
Met Thr Arg Pro Phe Glu Thr His Pro Gly His Asp Gly Glu Leu His
1               5                   10                  15
Glu Leu His Ala Ala Leu Gln Arg Arg Leu Asp Glu Leu Leu Pro Val
            20                  25                  30
Gly Asp Glu Arg Asp Arg Val Ser Ser Ala Met Arg Glu Gly Val Leu
        35                  40                  45
Ala Pro Gly Lys Arg Ile Arg Pro Leu Leu Ile Leu Ala Ala Arg
    50                  55                  60
Asp Leu Gly Cys Asp Arg Asp His Pro Gly Leu Leu Asp Met Ala Cys
65                  70                  75                  80
Ala Val Glu Met Val His Ala Ser Ser Leu Ile Leu Asp Asp Ile Pro
                85                  90                  95
Cys Met Asp Asn Ala Ala Leu Arg Arg Gly Arg Pro Thr Ile His Arg
            100                 105                 110
Gln Tyr Gly Glu Asp Val Ala Ile Leu Ala Ala Val Ala Leu Leu Ser
        115                 120                 125
Ser Ala Phe Gly Val Met Val Ala Ala Gln Gly Leu Ser Pro Glu Cys
    130                 135                 140
Arg Ser Gln Ala Val Ala Glu Leu Ser Met Ala Val Gly Thr Gln Gly
145                 150                 155                 160
Leu Val Gln Gly Gln Tyr Lys Asp Leu Arg Glu Gly Thr Ala Pro Arg
                165                 170                 175
Ser Ala Glu Glu Ile Ala Thr Thr Asn Glu Leu Lys Thr Ser Val Leu
            180                 185                 190
Phe Gly Ala Thr Leu Gln Ile Ala Ala Leu Ala Ala Gly Ala Ser Pro
        195                 200                 205
Ala Ala Arg Gln Lys Met Arg Cys Phe Ala Gln Asp Leu Gly Gln Ala
    210                 215                 220
Phe Gln Leu Leu Asp Asp Leu Ala Asp Gly His Ala Gly Thr Gly Lys
225                 230                 235                 240
Asp Ile Asn Lys Asp Ala Gly Lys Ser Thr Leu Val Ala Met Leu Gly
                245                 250                 255
Ser Asp Ala Val Arg Glu Arg Leu Asp Thr His Leu Arg Arg Ala Asp
            260                 265                 270
Ala His Phe Ser Arg Ala Cys Gly Lys Asn Gln Ala Thr Arg Arg Phe
        275                 280                 285
Met His Ala Trp Phe Ser Lys Gln Leu Ala Ala Phe Ser
    290                 295                 300
```

<210> SEQ ID NO 3
<211> LENGTH: 1050
<212> TYPE: DNA
<213> ORGANISM: Pantoea agglomerans strain DC404

<400> SEQUENCE: 3

```
atgaaggacg cgcatctggt tcagcgtaaa aatgaccacc tggatatcgt gctgcaccct      60
gaccgggcga tgagtaccat cgcaccgga tttgacgcct ggcgttttga acactgcgcc      120
ctcccggagc tggatctcga cggtatcgat ctctccacca ccctgttttc ccgcccgctg     180
aaagccccgg tgctgatcag ctccatgacc ggcggcgcgg cgcgcgccag agacattaac     240
cgtcatctgg cccaggcggc gcaaaccctt gggctggcga tgggcgtcgg ttcccagcgc     300
```

-continued

```
gtggcgctgg aggacggcgc gcagcacggg ctggatgccc agctacgcca tatcgccccg      360
gacgtgccgc tgctggctaa ccttggcgcg gcgcagatcc gcggtgcgca ggggctggac      420
tacgcccggc gcgcggtgga catgatcgac gccgacgcgt taattgtgca tctgaacccg      480
ctgcaggagg cgctccaggg cggcggcgat cgcgactggc gcggcatcct caacgccatt      540
gcgcagctgg tgcgcgacct gccggtaccg gtggtggtta agaggtgggc gccgggatc       600 tccccggacg ttgcctgccg actggcggac gtcggcgtgg cgatgatcga cattgccggc      660
gcgggcggaa ccagctgggc ggcggtggaa gctgaacgcg ccccgacccc cgaggcgcga      720
aatgtggcga tggcctttgc cgactggggc attcctactg ccgatgcgct gcgtcgcgtc      780
catcttgcgc tgcctgatat cccgcttatc gcctccggcg gcatcgccaa cggcattgac      840
gcagcaaaag ccatcgcgct gggtgcagat ctggtgggcc aggccgcggc ggtgctggcg      900
catgccaacg cctccggcga gcggcaatt gcccatttcc gcaccctgat tacgcagctg       960
cggatcgcct gtttctgtac cggcagtgca aacctgcagg cgttgcgaca cgccacgctg     1020
cttccggtca acggcggcgc atccctgtga                                      1050
```

<210> SEQ ID NO 4
<211> LENGTH: 349
<212> TYPE: PRT
<213> ORGANISM: Pantoea agglomerans strain DC404

<400> SEQUENCE: 4

```
Met Lys Asp Ala His Leu Val Gln Arg Lys Asn Asp His Leu Asp Ile
  1               5                  10                  15

Val Leu His Pro Asp Arg Ala Met Ser Thr Ile Arg Thr Gly Phe Asp
             20                  25                  30

Ala Trp Arg Phe Glu His Cys Ala Leu Pro Glu Leu Asp Leu Asp Gly
         35                  40                  45

Ile Asp Leu Ser Thr Thr Leu Phe Ser Arg Pro Leu Lys Ala Pro Val
     50                  55                  60

Leu Ile Ser Ser Met Thr Gly Gly Ala Ala Arg Ala Arg Asp Ile Asn
 65                  70                  75                  80

Arg His Leu Ala Gln Ala Ala Gln Thr Leu Gly Leu Ala Met Gly Val
                 85                  90                  95

Gly Ser Gln Arg Val Ala Leu Glu Asp Gly Ala Gln His Gly Leu Asp
            100                 105                 110

Ala Gln Leu Arg His Ile Ala Pro Asp Val Pro Leu Leu Ala Asn Leu
        115                 120                 125

Gly Ala Ala Gln Ile Arg Gly Ala Gln Gly Leu Asp Tyr Ala Arg Arg
    130                 135                 140

Ala Val Asp Met Ile Asp Ala Asp Ala Leu Ile Val His Leu Asn Pro
145                 150                 155                 160

Leu Gln Glu Ala Leu Gln Gly Gly Gly Asp Arg Asp Trp Arg Gly Ile
                165                 170                 175

Leu Asn Ala Ile Ala Gln Leu Val Arg Asp Leu Pro Val Pro Val Val
            180                 185                 190

Val Lys Glu Val Gly Ala Gly Ile Ser Pro Asp Val Ala Cys Arg Leu
        195                 200                 205

Ala Asp Val Gly Val Ala Met Ile Asp Ile Ala Gly Ala Gly Gly Thr
    210                 215                 220

Ser Trp Ala Ala Val Glu Ala Glu Arg Ala Pro Thr Pro Glu Ala Arg
225                 230                 235                 240
```

-continued

```
Asn Val Ala Met Ala Phe Ala Asp Trp Gly Ile Pro Thr Ala Asp Ala
            245                 250                 255

Leu Arg Arg Val His Leu Ala Leu Pro Asp Ile Pro Leu Ile Ala Ser
        260                 265                 270

Gly Gly Ile Ala Asn Gly Ile Asp Ala Ala Lys Ala Ile Ala Leu Gly
                275                 280                 285

Ala Asp Leu Val Gly Gln Ala Ala Val Leu Ala His Ala Asn Ala
        290                 295                 300

Ser Gly Asp Ala Ala Ile Ala His Phe Arg Thr Leu Ile Thr Gln Leu
305                 310                 315                 320

Arg Ile Ala Cys Phe Cys Thr Gly Ser Ala Asn Leu Gln Ala Leu Arg
                325                 330                 335

His Ala Thr Leu Leu Pro Val Asn Gly Gly Ala Ser Leu
            340                 345
```

<210> SEQ ID NO 5
<211> LENGTH: 1170
<212> TYPE: DNA
<213> ORGANISM: Pantoea agglomerans strain DC404

<400> SEQUENCE: 5

```
atgaaaaaat gggatctgat tctggtcggc gcggggctgg ccaacgggct tatcgcctgg      60
cgactaaagc agcgtcatcc gacgcttgct gtattaatgc tggagtgcgg cgacgcgccc     120
ggcggaaacc acacctggtc ctttcaccaa cacgatatca cgccagccca gcacgcctgg     180
ctggcgccgc tggtggccca tcgctgggac gggtacgacg tccactttcc gaacgtgtcg     240
cgcaccctgc atgacggcta cctgaccatc acctccacgc gttttgccca agcgatgcgc     300
gggctgatga agagaatttt gctgacaaac gtgaccgtgt cacgggtgag cgggcaggaa     360
gtaaccctca gcgacggacg acgctttacc gccggggcgg tgattgatgg ccgcggctat     420
cagccctcgc gcaccctcag cattggctat caggcgttca tcggccagga gtggcaactg     480
accgcgcccc acgggttaac gcgcccgatc ctgatggatg cccgcgtcgc ccagggcaac     540
ggctaccgct ttgtctatac cctgccgctc agcgccgaca ccctgcttat cgaagacacg     600
cactacattg acggcccgac gctcgacgcc gattcagccc gcgcgcggat tgccgattac     660
gcccgccagc agggctggca gcttgcgcgg ctggtgcgtg aggaacaggg ggcgctgccg     720
atcaccctgt ccggcgatcc ggccgccttc tggcaccagt ccatcatca gccggtcagc     780
ggcctgcgcg ccggtctgtt ccatgccacc accggctatt cgctgccgct ggcggttcgg     840
ctggcggacc gcattgccaa cgcgccggga ctgcatcagg gcgcgctcta tcagctgatc     900
gccgatttcg cggcgcgcca ctggcagaca caacgctttt tccgcctgct taaccgcatg     960
cttttcctgg ccggcacacc cgaccagcgc tggcgcgtga tgcagcggtt ttaccagctt    1020
gacgagcagc tgatcgcccg ttttatgcc ggccagcttc gctccgccga ccgcgcgcgc    1080
ctgctgcttg gcaaaccgcc ggtgccgatt gtcggggcga tcaaagccct gctccacact    1140
cattcttctc tgcgagccca tcataaatga                                     1170
```

<210> SEQ ID NO 6
<211> LENGTH: 389
<212> TYPE: PRT
<213> ORGANISM: Pantoea agglomerans strain DC404

<400> SEQUENCE: 6

```
Met Lys Lys Trp Asp Leu Ile Leu Val Gly Ala Gly Leu Ala Asn Gly
1               5                   10                  15
```

```
Leu Ile Ala Trp Arg Leu Lys Gln Arg His Pro Thr Leu Ala Val Leu
                20                  25                  30

Met Leu Glu Cys Gly Asp Ala Pro Gly Gly Asn His Thr Trp Ser Phe
            35                  40                  45

His Gln His Asp Ile Thr Pro Ala Gln His Ala Trp Leu Ala Pro Leu
        50                  55                  60

Val Ala His Arg Trp Asp Gly Tyr Asp Val His Phe Pro Asn Val Ser
 65                  70                  75                  80

Arg Thr Leu His Asp Gly Tyr Leu Thr Ile Thr Ser Thr Arg Phe Ala
                85                  90                  95

Gln Ala Met Arg Gly Leu Met Lys Glu Asn Leu Leu Thr Asn Val Thr
            100                 105                 110

Val Ser Arg Val Ser Gly Gln Glu Val Thr Leu Ser Asp Gly Arg Arg
        115                 120                 125

Phe Thr Ala Gly Ala Val Ile Asp Gly Arg Gly Tyr Gln Pro Ser Pro
130                 135                 140

His Leu Ser Ile Gly Tyr Gln Ala Phe Ile Gly Gln Glu Trp Gln Leu
145                 150                 155                 160

Thr Ala Pro His Gly Leu Thr Arg Pro Ile Leu Met Asp Ala Arg Val
                165                 170                 175

Ala Gln Gly Asn Gly Tyr Arg Phe Val Tyr Thr Leu Pro Leu Ser Ala
            180                 185                 190

Asp Thr Leu Leu Ile Glu Asp Thr His Tyr Ile Asp Gly Pro Thr Leu
        195                 200                 205

Asp Ala Asp Ser Ala Arg Ala Arg Ile Ala Asp Tyr Ala Arg Gln Gln
210                 215                 220

Gly Trp Gln Leu Ala Arg Leu Val Arg Glu Glu Gln Gly Ala Leu Pro
225                 230                 235                 240

Ile Thr Leu Ser Gly Asp Pro Ala Ala Phe Trp His Gln Phe His His
                245                 250                 255

Gln Pro Val Ser Gly Leu Arg Ala Gly Leu Phe His Ala Thr Thr Gly
            260                 265                 270

Tyr Ser Leu Pro Leu Ala Val Arg Leu Ala Asp Arg Ile Ala Asn Ala
        275                 280                 285

Pro Gly Leu His Gln Gly Ala Leu Tyr Gln Leu Ile Ala Asp Phe Ala
290                 295                 300

Ala Arg His Trp Gln Thr Gln Arg Phe Phe Arg Leu Leu Asn Arg Met
305                 310                 315                 320

Leu Phe Leu Ala Gly Thr Pro Asp Gln Arg Trp Arg Val Met Gln Arg
                325                 330                 335

Phe Tyr Gln Leu Asp Glu Gln Leu Ile Ala Arg Phe Tyr Ala Gly Gln
            340                 345                 350

Leu Arg Ser Ala Asp Arg Ala Arg Leu Leu Gly Lys Pro Pro Val
        355                 360                 365

Pro Ile Val Gly Ala Ile Lys Ala Leu Leu His Thr His Ser Ser Leu
370                 375                 380

Arg Ala His His Lys
385

<210> SEQ ID NO 7
<211> LENGTH: 1479
<212> TYPE: DNA
<213> ORGANISM: Pantoea agglomerans strain DC404
```

<400> SEQUENCE: 7

```
atgaaacaaa ccattgtaat tggcgccggg ttcggcggac tggcgctggc gattcgcctc       60
caggcggcgg gcattcctac cacgctgctg gagagccgcg acaaaccggg cggccgcgcc      120
tatgtctacg aagatcgcgg ctttaccttt gatgcgggtc ccaccgtcat caccgatccc      180
tccgccattg aggagctgtt caccctcgcc ggaaaacggc tgaaggacta cgttgagctg      240
atgccggtga cgccgttcta cgcctgtgc tgggaagacg gcaaggtttt cgactacgcc       300
aacgatcagg cggcgcttga gtcgcagatc gccgcgttta acccgaacga cgtggcgggc      360
tatcaccgct cctcgacta ctcccgggcg gtgtttgccg aaggctatct gaagctcggc       420
gcggtgccgt ttctctcgtt tcgcgacatg ctgcgcgccg tcctcaact ggcgcggctg       480
caggcatggc gcagcgtgta cgacaaagtg tcggcctacg tggaagacga gcacctgcgg      540
caggcatttt cgtttcactc gctgctggtg ggcggcaacc cgttctccac gtcttctatt      600
tacacctga tccacgccct ggagcgggaa tggggcgtct ggttcccgcg cggcggcacc       660
ggtgcgctgg ttcagggcat ggtgaagctg tttcaggatc ttgcggcac cctcaccctt       720
aacgctcagg ttgagcggct ggagacggtg gacaatcagg tgaaggccgt gcatctggtt      780
aacgggcagc ggctggaggc tgcggcggtg gcctcgaacg cggacgtggt aaatacctat      840
gcccgactgc tcgccatca cccgcacggc gcgctacgg ccaaaaagct gaaacgcaag       900
cgcatgagca actcgctgtt cgtgctctat tttggcctgg atcaccatca cacccagctg      960
gcgcaccata ccgtctgctt tggcccgcgt tataaagcgc taatcgatga aattttcagc     1020
gccgacaccc tgtcggaaga ttttcgctc tatctgcatg cgccctgcgt aaccgacccg      1080
tcgctggccc cgccggggtg cggcagctac tatgtgctcg cgccggtgcc gcacctcggt     1140
aacgccccgc tcgactggag cgtggaaggg ccgcgtctgc gggatcgcat ttttgattat     1200
ctcgaagcgc gctatatgcc ggggctgcgc tcccagctgg tgacgccg catgttcacg       1260
ccggaagatt ttcgcgatac gctcgatgcc tggcagggt cagcgttttc actggagccg      1320
atcctcaccc agagcgcctg gttccggccg cacaaccgcg acagcgtggt tgataacctc     1380
tacctggtcg cgccggaac gcatcccggc gctggcgtgc cgggcgtgat cggatccgcc     1440
aaggcaacgg cccagttaat gttaaaggat ttagcgtaa                           1479
```

<210> SEQ ID NO 8
<211> LENGTH: 492
<212> TYPE: PRT
<213> ORGANISM: Pantoea agglomerans strain DC404

<400> SEQUENCE: 8

```
Met Lys Gln Thr Ile Val Ile Gly Ala Gly Phe Gly Gly Leu Ala Leu
1               5                   10                  15

Ala Ile Arg Leu Gln Ala Ala Gly Ile Pro Thr Thr Leu Leu Glu Ser
            20                  25                  30

Arg Asp Lys Pro Gly Gly Arg Ala Tyr Val Tyr Glu Asp Arg Gly Phe
        35                  40                  45

Thr Phe Asp Ala Gly Pro Thr Val Ile Thr Asp Pro Ser Ala Ile Glu
    50                  55                  60

Glu Leu Phe Thr Leu Ala Gly Lys Arg Leu Lys Asp Tyr Val Glu Leu
65                  70                  75                  80

Met Pro Val Thr Pro Phe Tyr Arg Leu Cys Trp Glu Asp Gly Lys Val
                85                  90                  95

Phe Asp Tyr Ala Asn Asp Gln Ala Ala Leu Glu Ser Gln Ile Ala Ala
```

-continued

```
                100                 105                 110
        Phe Asn Pro Asn Asp Val Ala Gly Tyr His Arg Phe Leu Asp Tyr Ser
                    115                 120                 125

Arg Ala Val Phe Ala Glu Gly Tyr Leu Lys Leu Gly Ala Val Pro Phe
        130                 135                 140

Leu Ser Phe Arg Asp Met Leu Arg Ala Gly Pro Gln Leu Ala Arg Leu
        145                 150                 155                 160

Gln Ala Trp Arg Ser Val Tyr Asp Lys Val Ser Ala Tyr Val Glu Asp
                        165                 170                 175

Glu His Leu Arg Gln Ala Phe Ser Phe His Ser Leu Leu Val Gly Gly
                    180                 185                 190

Asn Pro Phe Ser Thr Ser Ser Ile Tyr Thr Leu Ile His Ala Leu Glu
                    195                 200                 205

Arg Glu Trp Gly Val Trp Phe Pro Arg Gly Gly Thr Gly Ala Leu Val
                    210                 215                 220

Gln Gly Met Val Lys Leu Phe Gln Asp Leu Gly Gly Thr Leu Thr Leu
        225                 230                 235                 240

Asn Ala Gln Val Glu Arg Leu Glu Thr Val Asp Asn Gln Val Lys Ala
                        245                 250                 255

Val His Leu Val Asn Gly Gln Arg Leu Glu Ala Ala Val Ala Ser
                    260                 265                 270

Asn Ala Asp Val Val Asn Thr Tyr Ala Arg Leu Leu Gly His His Pro
                    275                 280                 285

His Gly Ala Ala Thr Ala Lys Lys Leu Lys Arg Lys Arg Met Ser Asn
                    290                 295                 300

Ser Leu Phe Val Leu Tyr Phe Gly Leu Asp His His Thr Gln Leu
        305                 310                 315                 320

Ala His His Thr Val Cys Phe Gly Pro Arg Tyr Lys Ala Leu Ile Asp
                        325                 330                 335

Glu Ile Phe Ser Ala Asp Thr Leu Ser Glu Asp Phe Ser Leu Tyr Leu
                    340                 345                 350

His Ala Pro Cys Val Thr Asp Pro Ser Leu Ala Pro Pro Gly Cys Gly
                    355                 360                 365

Ser Tyr Tyr Val Leu Ala Pro Val Pro His Leu Gly Asn Ala Pro Leu
        370                 375                 380

Asp Trp Ser Val Glu Gly Pro Arg Leu Arg Asp Arg Ile Phe Asp Tyr
        385                 390                 395                 400

Leu Glu Ala Arg Tyr Met Pro Gly Leu Arg Ser Gln Leu Val Thr His
                        405                 410                 415

Arg Met Phe Thr Pro Glu Asp Phe Arg Asp Thr Leu Asp Ala Trp Gln
                    420                 425                 430

Gly Ser Ala Phe Ser Leu Glu Pro Ile Leu Thr Gln Ser Ala Trp Phe
                    435                 440                 445

Arg Pro His Asn Arg Asp Ser Val Val Asp Asn Leu Tyr Leu Val Gly
                    450                 455                 460

Ala Gly Thr His Pro Gly Ala Gly Val Pro Gly Val Ile Gly Ser Ala
        465                 470                 475                 480

Lys Ala Thr Ala Gln Leu Met Leu Lys Asp Leu Ala
                        485                 490
```

<210> SEQ ID NO 9
<211> LENGTH: 927
<212> TYPE: DNA
<213> ORGANISM: Pantoea agglomerans strain DC404

-continued

```
<400> SEQUENCE: 9
atgtcccagc cgcttctcga acacgccagc gccaccatga ccgccggttc taaaagtttc      60
gccaccgcct caaagctgtt tgacaaacgc acccggcgca gcgcgctgat gctctatacc     120
tggtgccgct actgcgacga tgttatcgac ggacaggtgg tgggttttgc tgccccgacc     180
gagcagagcg acacgcccga ggcgcgcctg aacggctgc gtaagatgac gcgccgcgcc      240
tacgacgggg aaaccatgca agagccgccg ttcgccgcct tcaggaggt tgccctcgcc      300
catgccattc cgcctactca ggccttcgac cacctggaag ctatgcgat ggacgtgcgc      360
aacgagcgct attacagcct cgatgatacg ctccgctact gttatcacgt ggcgggcgtg     420
gtcggcctga tgatggccag ggtgatggga gtgcgggacg aagccacgct ggatcgcgcc     480
tgcgatctgg gcattgcctt tcagctcacc aatatcgcca gggatatcgt tgacgatgcg     540
caggtgggac gctgctacct gccgcagcag tggctggcgg aagtcggact caatgaacag     600
acctgcaccg tgcgggccaa ccgtccggcg ctggcgcgtc tggcagcgcg gctggtgacc     660
gaggctgagc cctattatca gtcagcgctt gccgggctgg gggatctgcc cctgcgctcc     720
gcctgggcga ttgccaccgc gcacggggtg tatcgtgaga tcgggtgaa ggtgctgatg      780
gcgggtgaaa aagcatggga tacccgccag ggcacgacgc gcgcggagaa gctggcgctg     840
gttatttccg gcgcgaagca ggcgatggct tcccggaagg cgagctggcc gccgcgcgat     900
ccgcacctct ggcagcgccc gcgctag                                         927

<210> SEQ ID NO 10
<211> LENGTH: 308
<212> TYPE: PRT
<213> ORGANISM: Pantoea agglomerans strain DC404

<400> SEQUENCE: 10

Met Ser Gln Pro Leu Leu Glu His Ala Ser Ala Thr Met Thr Ala Gly
1               5                   10                  15

Ser Lys Ser Phe Ala Thr Ala Ser Lys Leu Phe Asp Lys Arg Thr Arg
            20                  25                  30

Arg Ser Ala Leu Met Leu Tyr Thr Trp Cys Arg Tyr Cys Asp Asp Val
        35                  40                  45

Ile Asp Gly Gln Val Val Gly Phe Ala Ala Pro Thr Glu Gln Ser Asp
    50                  55                  60

Thr Pro Glu Ala Arg Leu Gln Arg Leu Arg Lys Met Thr Arg Arg Ala
65                  70                  75                  80

Tyr Asp Gly Glu Thr Met Gln Glu Pro Pro Phe Ala Ala Phe Gln Glu
                85                  90                  95

Val Ala Leu Ala His Ala Ile Pro Pro Thr Gln Ala Phe Asp His Leu
            100                 105                 110

Glu Gly Tyr Ala Met Asp Val Arg Asn Glu Arg Tyr Tyr Ser Leu Asp
        115                 120                 125

Asp Thr Leu Arg Tyr Cys Tyr His Val Ala Gly Val Val Gly Leu Met
    130                 135                 140

Met Ala Arg Val Met Gly Val Arg Asp Glu Ala Thr Leu Asp Arg Ala
145                 150                 155                 160

Cys Asp Leu Gly Ile Ala Phe Gln Leu Thr Asn Ile Ala Arg Asp Ile
                165                 170                 175

Val Asp Asp Ala Gln Val Gly Arg Cys Tyr Leu Pro Gln Gln Trp Leu
            180                 185                 190
```

```
Ala Glu Val Gly Leu Asn Glu Gln Thr Cys Thr Val Arg Ala Asn Arg
            195                 200                 205

Pro Ala Leu Ala Arg Leu Ala Arg Leu Val Thr Glu Ala Glu Pro
    210                 215                 220

Tyr Tyr Gln Ser Ala Leu Ala Gly Leu Gly Asp Leu Pro Leu Arg Ser
225                 230                 235                 240

Ala Trp Ala Ile Ala Thr Ala His Gly Val Tyr Arg Glu Ile Gly Val
                245                 250                 255

Lys Val Leu Met Ala Gly Glu Lys Ala Trp Asp Thr Arg Gln Gly Thr
            260                 265                 270

Thr Arg Ala Glu Lys Leu Ala Leu Val Ile Ser Gly Ala Lys Gln Ala
            275                 280                 285

Met Ala Ser Arg Lys Ala Ser Trp Pro Pro Arg Asp Pro His Leu Trp
            290                 295                 300

Gln Arg Pro Arg
305

<210> SEQ ID NO 11
<211> LENGTH: 558
<212> TYPE: DNA
<213> ORGANISM: Pantoea agglomerans strain DC404

<400> SEQUENCE: 11
atgcttgcgt tgtggaatac cgggatcgtg ctactgacta tcatcatcat ggaaggggtg      60
gcaacgttcg cacacaagta catcatgcac ggctggggat ggggctggca tcattcgcac     120
cataccccgc gcaaaggggc gtttgagcgt aacgatctct atgcggtggt gtttgcgcta     180
ctggccattg cgctgattta cgcgggcagc gaagggtact ggccgcttca gtggattggc     240
gcgggaatga ccggctacgg cgtgatctac tttatcgttc acgatggttt agtccaccag     300
cgctggccgt tccgttacgt gccgcgccgc ggctatctgc gccgcctcta catggcacac     360
cggctgcatc acgcggtgcg ggggcgcgaa gggtgcgtct ccttcgggtt tatctacgcc     420
ccaccggtgg acaagctgca ggcggtgctg cgcgaacgta acggcagacc cgctagcgcg     480
ggcgctgcca gaggtgcgga tcgcgcggcg gccagctcgc cttccgggaa gccatcgcct     540
gcttcgcgcc ggaaataa                                                   558

<210> SEQ ID NO 12
<211> LENGTH: 185
<212> TYPE: PRT
<213> ORGANISM: Pantoea agglomerans strain DC404

<400> SEQUENCE: 12

Met Leu Ala Leu Trp Asn Thr Gly Ile Val Leu Leu Thr Ile Ile Ile
1               5                   10                  15

Met Glu Gly Val Ala Thr Phe Ala His Lys Tyr Ile Met His Gly Trp
            20                  25                  30

Gly Trp Gly Trp His His Ser His His Thr Pro Arg Lys Gly Ala Phe
        35                  40                  45

Glu Arg Asn Asp Leu Tyr Ala Val Val Phe Ala Leu Ala Ile Ala
    50                  55                  60

Leu Ile Tyr Ala Gly Ser Glu Gly Tyr Trp Pro Leu Gln Trp Ile Gly
65                  70                  75                  80

Ala Gly Met Thr Gly Tyr Gly Val Ile Tyr Phe Ile Val His Asp Gly
                85                  90                  95

Leu Val His Gln Arg Trp Pro Phe Arg Tyr Val Pro Arg Arg Gly Tyr
```

-continued

```
            100                 105                 110
Leu Arg Arg Leu Tyr Met Ala His Arg Leu His Ala Val Arg Gly
        115                 120                 125

Arg Glu Gly Cys Val Ser Phe Gly Phe Ile Tyr Ala Pro Pro Val Asp
    130                 135                 140

Lys Leu Gln Ala Val Leu Arg Glu Arg Asn Gly Arg Pro Ala Ser Ala
145                 150                 155                 160

Gly Ala Ala Arg Gly Ala Asp Arg Ala Ala Ser Ser Pro Ser Gly
                165                 170                 175

Lys Pro Ser Pro Ala Ser Arg Arg Lys
        180                 185
```

<210> SEQ ID NO 13
<211> LENGTH: 19
<212> TYPE: DNA
<213> ORGANISM: Artificial Sequence
<220> FEATURE:
<223> OTHER INFORMATION: Primer HK12

<400> SEQUENCE: 13
gagtttgatc ctggctcag                                              19

<210> SEQ ID NO 14
<211> LENGTH: 15
<212> TYPE: DNA
<213> ORGANISM: Artificial Sequence
<220> FEATURE:
<223> OTHER INFORMATION: Primer JCR14

<400> SEQUENCE: 14
acgggcggtg tgtac                                                  15

<210> SEQ ID NO 15
<211> LENGTH: 16
<212> TYPE: DNA
<213> ORGANISM: Artificial Sequence
<220> FEATURE:
<223> OTHER INFORMATION: Primer JCR15

<400> SEQUENCE: 15
gccagcagcc gcggta                                                 16

<210> SEQ ID NO 16
<211> LENGTH: 1324
<212> TYPE: DNA
<213> ORGANISM: Pantoea agglomerans strain DC404

<400> SEQUENCE: 16
atgacgctgg cggcaggcct aacacatgca agtcgaacgg taacaggaag cagcttgctg     60
cttcgctgac gagtggcgga cggtgagta atgtctgggg atctgcctga tggaggggga    120
taactactgg aaacggtagc taataccgca taacgtcgca agaccaaaga gggggacctt    180
cgggcctctt gccatcagat gaacccagat gggattagct agtaggtggg gtaacggctc    240
acctaggcga cgatccctag ctggtctgag aggatgacca gccacactgg aactgagaca    300
cggtccagac tcctacggga ggcagcagtg gggaatattg cacaatgggc gcaagcctga    360
tgcagccatg ccgcgtgtat gaagaaggcc ttcggttgt aaagtacttt cagcgaggag    420
gaaggtggta aggttaataa ccttatcaat tgacgttact cgcagaagaa gcaccggcta    480
actccgtgcc agcagccgcg gtaatacgga gggtgcaagc gttaatcgga attactgggc    540
```

```
gtaaagcgca cgcaggcggt ctgtcaagtc ggatgtgaaa tccccgggct caacctggga    600
actgcattcg aaactggcag gctagagtct tgtagagggg ggtagaattc caggtgtagc    660
ggtgaaatgc gtagagatct ggaggaatac cggtggcgaa ggcggccccc tggacaaaga    720
ctgacgctca ggtgcgaaag cgtggggagc aaacaggatt agataccctg gtagtccacg    780
ccgtaaacga tgtcgacttg gaggttgttc ccttgaggag tggcttccgg agctaacgcg    840
ttaagtcgac cgcctgggga gtacggccgc aaggttaaaa ctcaaatgaa ttgacggggg    900
cccgcacaag cggtggagca tgtggtttaa ttcgatgcaa cgcgaagaac cttacctggc    960
cttgacatcc acggaattcg gcagagatgc cttagtgcct tcgggaaccg tgagacaggt   1020
gctgcatggc tgtcgtcagc tcgtgttgtg aaatgttggg ttaagtcccg caacgagcgc   1080
aacccttatc ctttgttgcc agcgattcgg tcgggaactc aaaggagact gccggtgata   1140
aaccggagga aggtgggggga tgacgtcaag tcatcatggc ccttacggcc agggctacac   1200
acgtgctaca atggcgtata caaagagaag cgaactcgcg agagcaagcg gacctcataa   1260
agtacgtcgt agtccggatc ggagtctgca actcgactcc gtgaagtcgg aatcgctagt   1320
aatc                                                                1324

<210> SEQ ID NO 17
<211> LENGTH: 23
<212> TYPE: DNA
<213> ORGANISM: Artificial Sequence
<220> FEATURE:
<223> OTHER INFORMATION: Primer TET-1FP-1

<400> SEQUENCE: 17
gggtgcgcat gatcctctag agt                                             23

<210> SEQ ID NO 18
<211> LENGTH: 8814
<212> TYPE: DNA
<213> ORGANISM: Pantoea agglomerans strain DC404

<400> SEQUENCE: 18
accgcgaaga cagcaacgtg ctggagaccc gctttgagac ggaaccgggt cggtgctgat     60
caccgagtcg ctgaacagca cgcttgctgg ccggctgccg tggagcgaac tggcccgccg    120
catcgacggt attgagggcc acgtgacgct gaacgtcagc ctgcgtttcg gtaccgctgc    180
cgagacgcgc tccccgtgga gggcgaacac ctttaagggc gatgtgtttc acattgccga    240
tctgatggcg atgctgcgca ccagcgaaga cattgagatt acccactgcg acgatgaaaa    300
aattaccgcc cagctgatga cctcaccggg gtcgcgctcg ctggtcgccc tgctggtcac    360
cgagaaagag ccgctggcgg tgccggatct ctccgccatc gatgaccgca tcgaaaccag    420
ccaccttgcc tggtgcgact ggacccgcag cctcagctac cgcggtctct acgacaagca    480
cgtcaaacga tccgcgctgg cgctgaagtt tctctggtac tccccgaccg gcgcgctggc    540
ggcggcggcc accacctcgc tgccggaagg cattggcggg gagaaaaact acgactaccg    600
ctatgcctgg gtgcgcgatg cctgtctgat catcaaagcg ttcgtgttcc tcggtgcgct    660
ggaggactgc aaagccgcct tctcctggct gtcgaaaacc attattcgcc acgggcctga    720
gctgcgcgcc tgctatacgc tcgaaggtga cgaggtgccg gccgagtact atccgccgct    780
gcgcggatat cgggattccc gcccggtgcg ggtgggcaac aacgcccgca accagatcca    840
gctcagcatg tacggcgaca tgctcgccac cgcgcagctg tttatcgagg cgggacacgt    900
actggatctc gccacctcgc gcctgcttgg cgaactggcg aactgctgcg ccgacagctg    960
```

-continued

```
gcggcagaag gactccggca tctgggagtt accggacgag cagcactata cccactcgaa    1020
gatggcctgc tggctggcac tggatcgcgc cgtggcgatg gcagaacaga agcacatcga    1080
accgacctgg gtcgggcgct ggcagcgcga gcgcgatcgg atccgcgact ggatcgaaac    1140
ccactgctgg tcggagaaaa agcaggccta cgtgttttac gtcggggacg acgagcggct    1200
ggatgccgcg ctggcgctgg tgcacgacta cggcaacagc gtaaacccgc agcgtatgct    1260
ggccacctat cgcgccatca agcggagct gggacacgac acgcccatgc tctaccgcta    1320
cagcgaggtg aaaaggaag aaagcacctt tgtcgcctgc tcgttctggc tggtggaagc    1380
cctcgccgcg atgggtgaaa ccgacgaggc ccaggcggcc atgaccggca tcctcgagag    1440
gctctgcgac cggggcaatg ttgaaacttt taacgagatg tttgatgtgc gtaccgacga    1500
gtggcgcggc aaccttcctc aggggctgag ccatctggcg ctgatctgcg ccgcgcaggc    1560
gctttcggaa aaatgccgca acacgcgcga ctgacgcacg cgtagctaag gagaagacga    1620
tgaccatcag aggtatcgaa catattggta ttaccgtcgc cgacctcacc ggggcggagc    1680 ggttttcat cgaggcgctg gatgccagcg tgctctaccg catcgtgccg cccgcgcgg    1740 cggacaatgc catcagcggc gaccagatga cgcggctcaa tggctttccc ccggagatgc    1800
gggttaccgg cctggccatg ctgcgtctcg gcaacggctg caatattgag ctgtttgaga    1860
tcgatcccgg cgtggcagac gcgccggaa atatcagcca ggcgggcctg aaccacctgt    1920
cggtttacgt ggacgacatt cagcaggccg cgcacgggt aaaagcacag ggcgccacgc    1980
tgtttgacgg gccgagcgac tgctttgctc aggaagaggg ccgcggcaac cagacctggt    2040
tctgccgcac gccttttggc ctgctgattg aactcatctc ccttccctcg ccgcttcgct    2100
acgatgcgca ggcgcagcaa acccgctgga tcccccagcg ctgacaggcc tctctcacgc    2160
gggcatcgcc cgcgttgtca taccctcgtc accgtcctga caaaaattaa caataaattt    2220 tcattttca gccagacttt aagcacatag cgtcgccatg acatttattt tcatctaaac    2280
ctatacaaga aaacattga tgtataactt tgcataccgc tgcacacagg ctcagactgc    2340
gacacccgtt gcgggtcagc gctatttcca tttcatctgc gagacgccgg gtaccaacca    2400
tgacaagacc ctttgaaaca catcccggtc acgacgggga actgcatgag ctgcacgctg    2460
ccctgcaacg tcgcctggat gaactgctgc ccgttggcga tgagcgggat cgggtcagca    2520
gcgcaatgcg cgaaggcgta ctggcaccgg ggaaacgcat tcgcccgctg ctcctgatcc    2580
tcgccgcccg cgacctcggc tgcgatcgcg accaccccgg cctgctggat atggcctgtg    2640
cggtggaaat ggtgcacgcc tcgtcgctga tcctcgacga tattccctgc atggataacg    2700
cggcgctccg cgcgggtcgc cctaccattc atcgccagta tggtgaagac gtggcaattc    2760
tcgctgcggt agcgttgctc agcagcgcct ttggcgtgat ggtcgcggcg cagggattgt    2820
ctcccgagtg ccgcagccag gcggtggcgg agctgtcgat ggcggtcggt acccagggtc    2880
tggtgcaggg tcagtataag gatctgcgtg aaggcaccgc cccgcgcagc gccgaggaga    2940
tcgccaccac caacgaactg aaaaccagcg tgctgtttgg tgccacgctg caaatcgcgg    3000
ccctggcggc aggcgcctcg ccggcggcgc gccagaaaat gcgctgcttt gcgcaggatt    3060
taggccaggg gttccagctg ctggacgatc tggcggacgg ccatgccggg accggcaaag    3120
acatcaataa ggacgcgggt aagtccacgc tggtggcgat gctcggcagc gacgcggtgc    3180
gcgagcggct cgacacccat ctgcgccgcg cagacgccca ttttcacgc gcctgcggaa    3240 aaaaccaggc cacgcgacgc tttatgcacg cctggttttc aaaacagctg gccgcgttta    3300
```

```
gctgagcaac ggatacaccc cggtaatatt tgtgggagatc acatgaagga cgcgcatctg   3360
gttcagcgta aaaatgacca cctggatatc gtgctgcacc ctgaccgggc gatgagtacc   3420
attcgcaccg gatttgacgc ctggcgtttt gaacactgcg ccctcccgga gctggatctc   3480
gacggtatcg atctctccac caccctgttt tcccgcccgc tgaaagcccc ggtgctgatc   3540
agctccatga ccggcggcgc ggcgcgcgcc agagacatta accgtcatct ggcccaggcg   3600
gcgcaaaccc ttgggctggc gatgggcgtc ggttcccagc gcgtggcgct ggaggacggc   3660
gcgcagcacg ggctggatgc ccagctacgc catatcgccc cggacgtgcc gctgctggct   3720
aaccttggcg cggcgcagat ccgcggtgcg caggggctgg actacgcccg cgcgcgggtg   3780
gacatgatcg acgccgacgc gttaattgtg catctgaacc cgctgcagga ggcgctccag   3840
ggcggcggcg atcgcgactg gcgcggcatc ctcaacgcca ttgcgcagct ggtgcgcgac   3900
ctgccggtac cggtggtggt taaagaggtg ggcgccggga tctccccgga cgttgcctgc   3960
cgactggcgg acgtcggcgt ggcgatgatc gacattgccg gcgcgggcgg aaccagctgg   4020
gcggcggtgg aagctgaacg cgccccgacc cccgaggcgc gaaatgtggc gatggccttt   4080
gccgactggg gcattcctac tgccgatgcg ctgcgtcgcg tccatcttgc gctgcctgat   4140
atcccgctta tcgcctccgg cggcatcgcc aacggcattg acgcagcaaa agccatcgcg   4200
ctgggtgcag atctggtggg ccaggccgcg gcggtgctgg cgcatgccaa cgcctccggc   4260
gacgcggcaa ttgcccattt ccgcaccctg attacgcagc tgcggatcgc ctgtttctgt   4320
accggcagtg caaacctgca ggcgttgcga cacgccacgc tgcttccggt caacggcggc   4380
gcatccctgt gacgcagtac ggtgccttat accggggagc ggtatgaaaa aatgggatct   4440
gattctggtc ggcgcggggc tggccaacgg gcttatcgcc tggcgactaa agcagcgtca   4500
tccgacgctt gctgtattaa tgctggagtg cggcgacgcg cccggcggaa accacacctg   4560
gtcctttcac caacacgata tcacgccagc ccagcacgcc tggctggcgc cgctggtggc   4620
ccatcgctgg gacgggtacg acgtccactt tccgaacgtg tcgcgcaccc tgcatgacgg   4680
ctacctgacc atcaccctcc agcgttttgc ccaagcgatg cgcgggctga tgaaagagaa   4740
tttgctgaca aacgtgaccg tgtcacgggt gagcgggcag gaagtaaccc tcagcgacgg   4800
acgacgcttt accgccgggg cggtgattga tggccgcggc tatcagccct cgccgcacct   4860
cagcattggc tatcaggcgt tcatcggcca ggagtggcaa ctgaccgcgc cccacgggtt   4920
aacgcgcccg atcctgatgg atgcccgcgt cgcccaggcc aacggctacc gctttgtcta   4980
taccctgccg ctcagcgccg acaccctgct tatcgaagac acgcactaca ttgacggccc   5040
gacgctcgac gccgattcag cccgcgcgcg gattgccgat tacgcccgcc agcagggctg   5100
gcagcttgcg cggctggtgc gtgaggaaca ggggcgctg ccgatcaccc tgtccggcga   5160
tccggccgcc ttctggcacc agttccatca tcagccggtc agcggcctgc gcgccggtct   5220
gttccatgcc accaccggct attcgctgcc gctggcggtt cggctggcgg accgcattgc   5280
caacgcgccg ggactgcatc agggcgcgct ctatcagctg atcgccgatt cgcggcgcg   5340 ccactggcag acacaacgct ttttccgcct gcttaaccgc atgctttttcc tggccggcac   5400 acccgaccag cgctggcgcg tgatgcagcg gttttaccag cttgacgagc agctgatcgc   5460 ccgttttat gccggccagc ttcgctccgc cgaccgcgcg cgcctgctgc ttggcaaacc   5520
gccggtgccg attgtcgggg cgatcaaagc cctgctccac actcattctt ctctgcgagc   5580
ccatcataaa tgaaacaaac cattgtaatt ggcgccgggt tcggcggact ggcgctggcg   5640
attcgcctcc aggcggcggg cattcctacc acgctgctgg agagccgcga caaacccggc   5700
```

```
ggccgcgcct atgtctacga agatcgcggc tttacctttg atgcgggtcc caccgtcatc    5760
accgatccct ccgccattga ggagctgttc accctcgccg gaaaacggct gaaggactac    5820
gttgagctga tgccggtgac gccgttctat cgcctgtgct gggaagacgg caaggttttc    5880
gactacgcca acgatcaggc ggcgcttgag tcgcagatcg ccgcgtttaa cccgaacgac    5940
gtggcgggct atcaccgctt cctcgactac tcccgggcgg tgtttgccga aggctatctg    6000
aagctcggcg cggtgccgtt tctctcgttt cgcgacatgc tgcgcgccgg tcctcaactg    6060
gcgcggctgc aggcatggcg cagcgtgtac gacaaagtgt cggcctacgt ggaagacgag    6120
cacctgcggc aggcattttc gtttcactcg ctgctggtgg gcggcaaccc gttctccacg    6180
tcttctattt acaccctgat ccacgccctg gagcgggaat ggggcgtctg gttcccgcgc    6240
ggcggcaccg gtgcgctggt tcagggcatg gtgaagctgt tcaggatct tggcggcacc     6300 ctcaccctta acgctcaggt tgagcggctg gagacggtgg acaatcaggt gaaggccgtg    6360
catctggtta acgggcagcg gctggaggct gcggcggtgg cctcgaacgc ggacgtggta    6420 aataccctatg cccgactgct cggccatcac ccgcacggcg ccgctacggc caaaaagctg   6480
aaacgcaagc gcatgagcaa ctcgctgttc gtgctctatt ttggcctgga tcaccatcac    6540
acccagctgg cgcaccatac cgtctgcttt ggcccgcgtt ataaagcgct aatcgatgaa    6600
attttcagcg ccgacaccct gtcggaagat ttttcgctct atctgcatgc gccctgcgta    6660
accgacccgt cgctggcccc gccggggtgc ggcagctact atgtgctcgc gccggtgccg    6720
cacctcggta acgcccgct cgactggagc gtggaagggc cgcgtctgcg ggatcgcatt     6780
tttgattatc tcgaagcgcg ctatatgccg gggctgcgct cccagctggt gacgcaccgc    6840
atgttcacgc cggaagattt tcgcgatacg ctcgatgcct ggcagggtc agcgttttca     6900 ctggagccga tcctcaccca gagcgcctgg ttccggccgc acaaccgcga cagcgtggtt    6960
gataacctct acctggtcgg cgccggaacg catcccggcg ctggcgtgcc gggcgtgatc    7020
ggatccgcca aggcaacggc ccagttaatg ttaaaggatt tagcgtaatg tcccagccgc    7080
ttctcgaaca cgccagcgcc accatgaccc ccggttctaa aagtttcgcc accgcctcaa    7140
agctgtttga caaacgcacc cggcgcagcg cgctgatgct ctatacctgg tgccgctact    7200
gcgacgatgt tatcgacgga caggtggtgg gttttgctgc cccgaccgag cagagcgaca    7260
cgcccgaggc gcgcctgcaa cggctgcgta agatgacgcg ccgcgcctac gacggggaaa    7320
ccatgcaaga gccgccgttc gccgcctttc aggaggttgc cctcgcccat gccattccgc    7380
ctactcaggc cttcgaccac ctggaaggct atgcgatgga cgtgcgcaac gagcgctatt    7440
acagcctcga tgatacgctc cgctactgtt atcacgtggc gggcgtggtc ggcctgatga    7500
tggccagggt gatgggagtg cgggacgaag ccacgctgga tcgcgcctgc gatctgggca    7560
ttgcctttca gctcaccaat atcgccaggg atatcgttga cgatgcgcag gtgggacgct    7620
gctacctgcc gcagcagtgg ctggcggaag tcggactcaa tgaacagacc tgcaccgtgc    7680
gggccaaccg tccggcgctg gcgcgtctgg cagcgcggct ggtgaccgag ctgagcccct    7740
attatcagtc agcgcttgcc gggctggggg atctgccct gcgctccgcc tgggcgattg     7800
ccaccgcgca cggggtgtat cgtgagatcg gggtgaaggt gctgatggcg ggtgaaaaag    7860
catgggatac ccgccagggc acgacgcgcg cggagaagct ggcgctggtt atttccggcg    7920
cgaagcaggc gatggcttcc cggaaggcga gctggccgcc gcgcgatccg cacctctggc    7980
agcgcccgcg ctagcgggtc tgccgttacg ttcgcgcagc accgcctgca gcttgtccac    8040
```

-continued

```
cggtggggcg tagataaacc cgaaggagac gcacccttcg cgcccccgca ccgcgtgatg    8100
cagccggtgt gccatgtaga ggcggcgcag atagccgcgg cgcggcacgt aacggaacgg    8160
ccagcgctgg tggactaaac catcgtgaac gataaagtag atcacgccgt agccggtcat    8220
tcccgcgcca atccactgaa gcggccagta cccttcgctg cccgcgtaaa tcagcgcaat    8280
ggccagtagc gcaaacacca ccgcatagag atcgttacgc tcaaacgccc ctttgcgcgg    8340
ggtatggtgc gaatgatgcc agcccatcc ccagccgtgc atgatgtact tgtgtgcgaa     8400
cgttgccacc ccttccatga tgatgatagt cagtagcacg atcccggtat tccacaacgc    8460
aagcataggt ttttcctgta gttgacagcc cctaaagcgt agcctggaat gccaggaaac    8520
ataagcgtaa cctcgcggat aatgcgcttt tcaggcgtaa aagcatttat gacaattatt    8580
catcgcgcca cgttcacgcc gtgacgccct gctcaccgcg cggcagcagc cgcatcggct    8640
gataaacgcg cccggtttct gcgcgtcatc gcccggtgtg cgcggcgtca acgcaataaa    8700
acttactttc aaaaggcggc ccgaaaaggc taccctttt tattcttgtc atatactcga    8760
tctaacctga attatcgccg taacgtaccg cttcttttga ggtaatcccg gagc          8814
```

<210> SEQ ID NO 19
<211> LENGTH: 34
<212> TYPE: DNA
<213> ORGANISM: artificial sequence
<220> FEATURE:
<223> OTHER INFORMATION: Primer

<400> SEQUENCE: 19
gaattcacta gtcgagacgc cgggtaccaa ccat    34

<210> SEQ ID NO 20
<211> LENGTH: 25
<212> TYPE: DNA
<213> ORGANISM: artificial sequence
<220> FEATURE:
<223> OTHER INFORMATION: Primer

<400> SEQUENCE: 20
gaattctagc gcgggcgctg ccaga    25

What is claimed is:

1. An isolated nucleic acid molecule of SEQ ID NO: 18, encoding carotenoid biosynthetic pathway enzymes, comprising a polynucleotide wherein the genetic organization of the polynucleotides is: crtE-idi-crtY-crtI-crtB-crtZ, wherein the crtE-idi-crtY-crtI-crtB-crtZ genes are clustered in the order stated and wherein the transcription of the crtZ occurs in opposite orientation to that of criE-idi-crtY-crtI-crtB.

2. The isolated nucleic acid molecule of claim 1 consisting of the sequence as set forth in SEQ ID NO: 18.

3. An isolated nucleic acid molecule as set forth in SEQ ID NO: 18, wherein said nucleic acid molecule encodes crtE, idi, crtY, crtI, crtB and crtZ or an isolated nucleic acid molecule having at least 95% identity to SEQ ID NO: 18, wherein said isolated nucleic acid molecule encodes the following enzymes: Geranylgeranyl pyrophosphate synthase (crtE), isopentenyl pyrophosphate (idi), lycopene cyclase (crtY), phytoene desaturase (crtI), phytoene synthase (crtB) and beta-carotene hydroxylase (crtZ).

4. The isolated nucleic acid molecule of claim 1 isolated from *Pantoea agglomerans* strain DC404.

5. A vector comprising the isolated nucleic acid molecule of claim 3.

6. A transformed host comprising the isolated nucleic acid molecule of claim 3.

7. The transformed host cell of claim 6 wherein the host cell is selected from the group-consisting of bacteria, yeast, filamentous fungi, algae, and green plants.

8. The transformed host cell of claim 6 wherein the host cell is selected from the group consisting of *Aspergillus, Trichoderma, Saccharomyces, Pichia, Candida, Hansenula, Yarrowia, Rhodosporidium, Lipomyces, Salmonella, Bacillus, Acinetobacter, Zymomonas, Agrobacterium, Flavobacterium, Rhodobacter, Rhodococcus, Streptomyces, Brevibacterium, Corynebacteria, Mycobacterium, Escherichia, Pantoea, Pseudomonas, Methylomonas, Methylobacter, Methylococcus, Methylosinus, Methylomicrobium, Methylocystis, Alcaligenes, Synechocystis, Synechococcus, Anabaena, Thiobacillus, Methanobacterium, Klebsiella, Methylophilus, Methylobacillus, Methylobacterium, Hyphomicrobium, Xanthobacter, Paracoccus, Nocardia, Arthrobacter, Rhodopseudomonas, Torulopsis, Rhodotorula*, and *Phaffia*.

9. A method for the production of carotenoid compounds comprising:

(a) providing a transformed host cell comprising:

(i) suitable levels of farnesyl pyrophosphate; and
(ii) a the isolated nucleic acid molecule of claim 6 under the control of suitable regulatory sequences;

(b) contacting the host cell of step (a) under suitable growth conditions with an effective amount of a fermentable carbon substrate whereby a carotenoid compound is produced.

10. A method according to any claim 9 wherein the transformed host cell is selected from the group consisting of C1 metabolizing hosts, bacteria, yeast, filamentous fungi, algae, and green plants.

11. A method according to claim 10 wherein the C1 metabolizing host is a methanotroph and the fermentable carbon substrate is selected from the group consisting of methane, methanol, formaldehyde, formic acid, methylated amines, methylated thiols, and carbon dioxide.

* * * * *